(12) United States Patent  
Luecking et al.

(10) Patent No.: US 7,338,958 B2
(45) Date of Patent: Mar. 4, 2008

(54) SULFOXIMINE-SUBSTITUTED PYRIMIDINES AS CDK-AND/OR VEGF INHIBITORS, THEIR PRODUCTION AND USE AS PHARMACEUTICAL AGENTS

(75) Inventors: Ulrich Luecking, Berlin (DE); Gerhard Siemeister, Berlin (DE); Martin Krueger, Berlin (DE); Rolf Jautelat, Berlin (DE)

(73) Assignee: Schering AG, Berlin (DE)

( * ) Notice: Subject to any disclaimer, the term of this patent is extended or adjusted under 35 U.S.C. 154(b) by 417 days.

(21) Appl. No.: 10/966,098

(22) Filed: Oct. 18, 2004

(65) Prior Publication Data

US 2005/0176743 A1    Aug. 11, 2005

Related U.S. Application Data

(60) Provisional application No. 60/512,921, filed on Oct. 22, 2003.

(30) Foreign Application Priority Data

Oct. 16, 2003    (DE) ................. 103 49 423

(51) Int. Cl.
| | |
|---|---|
| *A61K 31/506* | (2006.01) |
| *C07D 239/34* | (2006.01) |
| *C07D 239/38* | (2006.01) |
| *C07D 239/48* | (2006.01) |
| *A61P 35/00* | (2006.01) |
| *C07D 239/30* | (2006.01) |
| *C07D 239/56* | (2006.01) |
| *C07C 315/04* | (2006.01) |
| *C07C 317/14* | (2006.01) |
| *C07C 307/02* | (2006.01) |
| *C07C 311/07* | (2006.01) |

(52) U.S. Cl. ............ 514/269; 514/272; 544/323; 544/332; 544/297; 544/334; 544/319; 568/30; 568/36; 560/13; 564/95; 564/440

(58) Field of Classification Search ........... 514/269, 514/272; 544/323, 332
See application file for complete search history.

(56) References Cited

U.S. PATENT DOCUMENTS

2004/0063737 A1    4/2004 Luecking et al.

2004/0224966 A1    11/2004 Brumby et al.

FOREIGN PATENT DOCUMENTS

| WO | WO 98/41512 | 9/1998 |
|---|---|---|
| WO | WO 00/53595 | 9/2000 |
| WO | WO 01/64654 | 9/2001 |
| WO | WO 02/096887 | 12/2002 |
| WO | WO 02/096888 | 12/2002 |
| WO | WO 03/076437 | 9/2003 |

OTHER PUBLICATIONS

Blain, et al., J Biolog. Chem., vol. 272, No. 41, 1997, pp. 25863-25872.*
Rane, et al., Nature America, vol. 22, pp. 44-52, May 1999.*
Leclerc, et al., J. Biolog. Chem., 276, No. 1, Jan. 2, 2001, pp. 251-260.*
BBC News/Health, Jan. 21, 2006, 3 pages.*
Wikipedia (Isomer) , Jan. 2007.*
Wikipedia (Salt) , Jan. 2007.*

* cited by examiner

*Primary Examiner*—Mark L. Berch
*Assistant Examiner*—Cecilia M Jaisle
(74) *Attorney, Agent, or Firm*—Millen, White, Zelano & Branigan, P.C.

(57) ABSTRACT

This invention relates to pyrimidine derivatives of general formula I

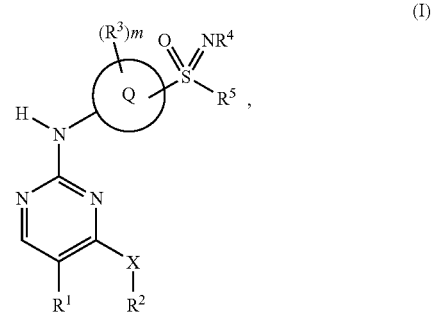

in which Q, $R^1$, $R^2$, $R^3$, $R^4$, $R^5$, X, and m have the meanings that are contained in the description, as inhibitors of cyclin-dependent kinases and VEGF-receptor tyrosine kinases, their production as well as their use as medications for treatment of various diseases.

13 Claims, 1 Drawing Sheet

SULFOXIMINE-SUBSTITUTED PYRIMIDINES AS CDK-AND/OR VEGF INHIBITORS, THEIR PRODUCTION AND USE AS PHARMACEUTICAL AGENTS

This application claims the benefit of the filing date of U.S. Provisional Application Ser. No. 60/512,921 filed Oct. 22, 2003 which is incorporated by reference herein.

This invention relates to sulfoximine-substituted pyrimidine derivatives, their process for production as well as their use as medications for treating various diseases.

The cyclin-dependent kinases (cyclin-dependent kinase, CDK) are an enzyme family that plays an important role in the regulation of the cell cycle and thus represents an especially advantageous target for the development of small inhibitory molecules. Selective inhibitors of the CDKs can be used for the treatment of cancer or other diseases that are caused by disorders of cell proliferation.

Receptor tyrosine kinases and their ligands, which specifically regulate the function of endothelial cells, are involved decisively in physiological as well as pathogenic angiogenesis. The Vascular Endothelial Growth Factor (VEGF)/VEGF-receptor system is of special importance here. In pathological situations, which are accompanied by increased neovascularization, such as, e.g., tumor diseases, an increased expression of angiogenic growth factors and their receptors was found. Inhibitors of the VEGF/VEGF receptor system can inhibit the build-up of a blood vessel system in the tumor, thus separate the tumor from the oxygen and nutrient supply and thus inhibit tumor growth.

Pyrimidines and analogs are already described as active ingredients, such as, for example, the 2-anilino-pyrimidines as fungicides (DE 4029650) or substituted pyrimidine derivatives for treatment of neurological or neurodegenerative diseases (WO 99/19305). As CDK inhibitors, the most varied pyrimidine derivatives are described, for example, bis(anilino)-pyrimidine derivatives (WO 00/12486), 2-amino-4-substituted pyrimidines (WO 01/14375), purines (WO 99/02162), 5-cyano-pyrimidines (WO 02/04429), anilinopyrimidines (WO 00/12486) and 2-hydroxy-3-N,N-dimethylaminopropoxy-pyrimidines (WO 00/39101).

In particular, pyrimidine derivatives that exhibit inhibitory actions relative to CDKs were disclosed in WO 02/096888 and WO 03/7076437. Compounds that contain a phenylsulfonamide group are known as inhibitors of the human carboanhydrases (especially carboanhydrase-2) and are used as diuretics, i.a., for treating glaucoma. The nitrogen atom and the oxygen atoms of the sulfonamide bind via hydrogen bridges to the zinc$^{2+}$ ion and the amino acid Thr 199 in the active center of carboanhydrase-2 and thus block their enzymatic function (A. Casini, F. Abbate, A. Scozzafava, C. T. Supuran, *Bioorganic. Med. Chem L.* 2003, 1, 2759.3). The clinical use of CDK inhibitors, which contain a phenylsulfonamide group, could be limited by the possibility of the inhibition of carboanhydrases and a side-effect spectrum that results therefrom.

Sulfoximines, such as, for example, sulfonimidoyl-modified triazoles as fungicides (H. Kawanishi, H. Morimoto, T. Nakano, T. Watanabe, K. Oda, K. Tsujihara, *Heterocycles* 1998, 49, 181) or arylalkylsulfoximines as herbicides and pesticides (Shell International Research, Ger. P. 2 129 678) are described as active ingredients.

The object of this invention is to provide compounds that exhibit better pharmaceutical properties, especially a reduction of carboanhydrase-2 inhibition, than the already known CDK inhibitors.

It was now found that compounds of general formula (I)

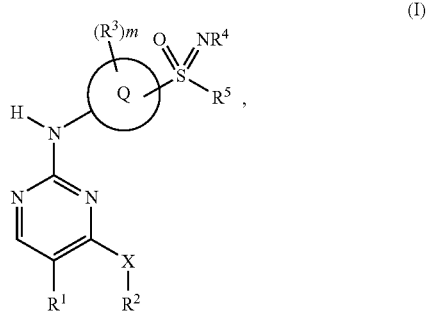

in which
Q stands for phenyl,
$R^1$ stands for hydrogen or halogen,
$R^2$ stands for $C_1$-$C_{10}$-alkyl, $C_2$-$C_{10}$-alkinyl, or aryl that is optionally substituted in one or more places, in the same way or differently, with hydroxy, halogen, $C_1$-$C_6$-alkyl, $C_1$-$C_6$-alkoxy, $C_2$-$C_6$-alkinyl, or with the group —$COR^6$,
X stands for oxygen, sulfur, or for the group —NH—,
$R^3$ stands for halogen, or for $C_1$-$C_6$-alkyl, or $C_1$-$C_6$-alkoxy that is optionally substituted in one or more places with halogen,
m stands for 0-4,
$R^4$ stands for the group $NO_2$, —CO—$R^6$, —$SO_2R^7$ or for $C_1$-$C_{10}$-alkyl,
$R^5$ stands for $C_1$-$C_{10}$-alkyl or $C_3$-$C_{10}$-cycloalkyl that is optionally substituted in one or more places, in the same way or differently, with hydroxy or $C_3$-$C_{10}$-cycloalkyl,
$R^6$ stands for hydrogen, $C_1$-$C_6$-alkyl, $C_1$-C6-alkoxy or $C_3$-$C_6$-cycloalkyl, which optionally can be substituted in one or more places, in the same way or differently, with $C_1$-$C_6$-alkyl,
$R^7$ stands for $C_1$-$C_{10}$-alkyl that is optionally substituted in one or more places, in the same way or differently, with the group trimethylsilanyl (TMS), as well as their isomers, diastereomers, enantiomers and/or salts, are no longer able to inhibit carboanhydrases, whereby they simultaneously inhibit cyclin-dependent kinases and VEGF receptor tyrosine kinases already in the nanomolar range and thus can inhibit the proliferation of tumor cells and/or tumor angiogenesis.

Alkyl is defined in each case as a straight-chain or branched alkyl radical, such as, for example, methyl, ethyl, propyl, isopropyl, butyl, isobutyl, sec-butyl, tert-butyl, pentyl, isopentyl, hexyl, heptyl, octyl, nonyl and decyl.

Alkoxy is defined in each case as a straight-chain or branched alkoxy radical, such as, for example, methyloxy, ethyloxy, propyloxy, isopropyloxy, butyloxy, isobutyloxy, sec-butyloxy, pentyloxy, isopentyloxy, hexyloxy, heptyloxy, octyloxy, nonyloxy, decyloxy, undecyloxy or dodecyloxy.

Cycloalkyl is defined in each case as cyclopropyl, cyclobutyl, cyclopentyl, cyclohexyl and cycloheptyl.

Heterocycloalkyl stands for an alkyl ring that comprises 3-12 carbon atoms, which instead of carbon contains one or more of the same or different heteroatoms, such as, e.g., oxygen, sulfur or nitrogen.

As heterocycloalkyls, there can be mentioned, e.g.: oxiranyl, oxethanyl, aziridinyl, azetidinyl, tetrahydrofuranyl, pyrrolidinyl, dioxolanyl, imidazolidinyl, pyrazolidinyl, dioxanyl, piperidinyl, morpholinyl, dithianyl, thiomorpholinyl, piperazinyl, trithianyl, quinuclidinyl, etc.

The ring systems, in which optionally one or more possible double bonds can be contained in the ring, are defined as, for example, cycloalkenyls, such as cyclopropenyl, cyclobutenyl, cyclopentenyl, cyclohexenyl, or cycloheptenyl, whereby the linkage can be carried out both to the double bond and to the single bonds.

Halogen is defined in each case as fluorine, chlorine, bromine or iodine.

The alkenyl substituents are in each case straight-chain or branched, whereby, for example, the following radicals are meant: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, ethinyl, prop-1-in-1-yl, but-1-in-1-yl, but-2-in-1-yl, but-3-en-1-yl, and allyl.

The aryl radical in each case has 6-12 carbon atoms, such as, for example, naphthyl, biphenyl, and especially phenyl.

Heteroaryl is defined as a heteroaryl radical, which in each case can also be benzocondensed. For example, thiophene, furan, oxazole, thiazole, imidazole, pyrazole, triazole, thia-4H-pyrazole, and benzo derivatives thereof can be mentioned as 5-ring heteroaromatic compounds, and pyridine, pyrimidine, triazine, quinoline, isoquinoline and their benzocondensed derivatives can be mentioned as 6-ring heteroaromatic compounds.

Isomers are defined as chemical compounds of the same summation formula but different chemical structure. In general, constitutional isomers and stereoisomers are distinguished.

Constitutional isomers have the same summation formula but are distinguished by the way in which their atoms or groups of atoms are linked. These include functional isomers, positional isomers, tautomers or valence isomers.

In principle, stereoisomers have the same structure (constitution)—and thus also the same summation formula—but are distinguished by the spatial arrangement of the atoms.

In general, configurational isomers and conformational isomers are distinguished. Configurational isomers are stereoisomers that can be converted into one another only by bond breaking. These include enantiomers, diastereomers and E/Z (cis/trans) isomers.

Enantiomers are stereoisomers that behave toward one another like image and mirror image and do not have any symmetry plane. All stereoisomers that are not enantiomers are referred to as diastereomers. E/Z (cis/trans) isomers of double bonds are a special case.

Conformational isomers are stereoisomers that can be converted into one another by the turning of single bonds.

To differentiate the types of isomerism from one another, see also the IUPAC rules, Section E (Pure Appl. Chem. 45, 11-30, 1976).

If an acid group is included, the physiologically compatible salts of organic and inorganic bases, such as, for example, the readily soluble alkali salts and earth-alkaline salts, as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropanediol, Sovak base, and 1-amino-2,3,4-butanetriol, are suitable as salts.

If a basic group is included, the physiologically compatible salts of organic and inorganic acids, such as hydrochloric acid, sulfuric acid, phosphoric acid, citric acid, or tartaric acid, i.a., are suitable.

Those compounds of general formula (I), in which
Q stands for phenyl,
$R^1$ stands for hydrogen or halogen,
$R^2$ stands for $C_1$-$C_{10}$-alkyl, $C_2$-$C_{10}$-alkinyl or aryl that is optionally substituted in one or more places, in the same way or differently, with hydroxy, halogen, $C_1$-$C_6$-alkyl, $C_1$-$C_6$-alkoxy, $C_2$-$C_6$-alkinyl or with the group —$COR^6$,
X stands for oxygen, sulfur or for the group —NH—,
$R^3$ stands for halogen or for $C_1$-$C_6$-alkyl or $C_1$-$C_6$-alkoxy that is optionally substituted in one or more places with halogen,
m stands for 0-2,
$R^4$ stands for hydrogen or for the group $NO_2$, —CO—$R^6$, —$SO_2R^7$ or for $C_1$-$C_{10}$-alkyl,
$R^5$ stands for $C_1$-$C_{10}$-alkyl or $C_3$-$C_{10}$-cycloalkyl that is optionally substituted in one or more places, in the same way or differently, with hydroxy or $C_3$-$C_{10}$-cycloalkyl,
$R^6$ stands for hydrogen, $C_1$-$C_6$-alkyl, $C_1$-$C_6$-alkoxy or $C_3$-$C_6$-cycloalkyl, which optionally can be substituted in one or more places, in the same way or differently, with $C_1$-$C_6$-alkyl,
$R^7$ stands for $C_1$-$C_{10}$-alkyl that is optionally substituted in one or more places, in the same way or differently, with the group trimethylsilanyl (TMS), as well as their isomers, diastereomers, enantiomers and/or salts, are especially effective.

In addition, specially selected compounds of general formula (I) are those in which
Q stands for phenyl,
$R^1$ stands for hydrogen or halogen,
$R^2$ stands for methyl, ethyl, propyl, isopropyl, butyl, isobutyl, pentyl, isopentyl, isohexyl, propargyl or phenyl that is optionally substituted in one or more places, in the same way or differently, with hydroxy, halogen, methyl, methoxy, ethinyl or with the group —COH or —$COCH_3$,
X stands for oxygen, sulfur or for the group —NH—,
$R^3$ stands for halogen, methyl, methoxy or —$CF_3$,
m stands for 0-1,
$R^4$ stands for hydrogen, methyl, or for the group $NO_2$, —$COOC_2H_5$ or —$SO_2$—$C_2H_4$—$Si(CH_3)_3$,
$R^5$ stands for methyl, ethyl, cyclopropyl, cyclopentyl, —($CH_2$)-cyclopropyl or hydroxyethyl, as well as their isomers, diastereomers, enantiomers and/or salts.

The compounds according to the invention essentially inhibit cyclin-dependent kinases, upon which their action is based, for example, against cancer, such as solid tumors and leukemia; auto-immune diseases, such as psoriasis, alopecia and multiple sclerosis; chemotherapy agent-induced alopecia and mucositis; cardiovascular diseases, such as stenoses, arterioscleroses and restenoses; infectious diseases, such as, e.g., those caused by unicellular parasites, such as trypanosoma, toxoplasma or plasmodium, or those caused by fungi; nephrological diseases, such as, e.g., glomerulonephritis; chronic neurodegenerative diseases, such as Huntington's disease, amyotrophic lateral sclerosis, Parkinson's disease, AIDS dementia and Alzheimer's disease; acute neurodegenerative diseases, such as ischemias of the brain and neurotraumas; and viral infections, such as, e.g., cytomegalic infections, herpes, hepatitis B and C, and HIV diseases.

The eukaryotic cell division cycle ensures the duplication of the genome and its distribution to the daughter cells by passing through a coordinated and regulated sequence of events. The cell cycle is divided into four successive phases: the G1 phase represents the time before the DNA replication, in which the cell grows and is sensitive to external stimuli. In the S phase, the cell replicates its DNA, and in the G2 phase, preparations are made for entry into mitosis. In mitosis (M phase), the replicated DNA separates, and cell division is complete.

The cyclin-dependent kinases (CDKs), a family of serine/threonine kinases, whose members require the binding of a cyclin (Cyc) as a regulatory subunit in order for them to activate, drive the cell through the cell cycle. Different CDK/Cyc pairs are active in the various phases of the cell cycle. CDK/Cyc pairs that are important to the basic function of the cell cycle are, for example, CDK4(6)/CycD, CDK2/CycE, CDK2/CycA, CDK1/CycA and CDK1/CycB. Some members of the CDK enzyme family have a regulatory function by influencing the activity of the abovementioned cell cycle CDKs, while no specific function could be associated with other members of the CDK enzyme family. One of the latter, CDK5, is distinguished in that it has an atypical regulatory subunit (p35) that deviates from the cyclins, and its activity is highest in the brain.

The entry into the cell cycle and the passage through the "restriction points," which marks the independence of a cell from further growth signals for the completion of the cell division that has begun, are controlled by the activity of the CDK4(6)/CycD and CDK2/CycE complexes. The essential substrate of these CDK complexes is the retinoblastoma protein (Rb), the product of the retinoblastoma tumor suppressor gene. Rb is a transcriptional co-repressor protein. In addition to other, still largely little understood mechanisms, Rb binds and inactivates transcription factors of the E2F type and forms transcriptional repressor complexes with histone-deacetylases (HDAC) (Zhang, H. S. et al. (2000). Exit from G1 and S Phase of the Cell Cycle is Regulated by Repressor Complexes Containing HDAC-Rb-hSWI/SNF and Rb-hSWI/SNF. *Cell* 101, 79-89). By the phosphorylation of Rb by CDKs, bonded E2F transcription factors are released and result in transcriptional activation of genes, whose products are required for the DNA synthesis and the progression through the S-phase. In addition, the Rb-phosphorylation brings about the breakdown of the Rb-HDAC complexes, by which additional genes are activated. The phosphorylation of Rb by CDKs is to be treated as equivalent to exceeding the "restriction points." For the progression through the S-phase and its completion, the activity of the CDK2/CycE and CDK2/CycA complexes is necessary, e.g., the activity of the transcription factors of the E2F type is turned off by means of phosphorylation by CDK2/CycA as soon as the cells are entered into the S-phase. After replication of DNA is complete, the CDK1 in the complex with CycA or CycB controls the entry into and the passage through phases G2 and M (FIG. 1).

According to the extraordinary importance of the cell-division cycle, the passage through the cycle is strictly regulated and controlled. The enzymes that are necessary for the progression through the cycle must be activated at the correct time and are also turned off again as soon as the corresponding phase is passed. Corresponding control points ("checkpoints") stop the progression through the cell cycle if DNA damage is detected, or the DNA replication or the creation of the spindle device is not yet completed.

The activity of the CDKs is controlled directly by various mechanisms, such as synthesis and degradation of cyclins, complexing of the CDKs with the corresponding cyclins, phosphorylation and dephosphorylation of regulatory threonine and tyrosine radicals, and the binding of natural inhibitory proteins. While the amount of protein of the CDKs in a proliferating cell is relatively constant, the amount of the individual cyclins oscillates with the passage through the cycle. Thus, for example, the expression of CycD during the early G1 phase is stimulated by growth factors, and the expression of CycE is induced after the "restriction points" are exceeded by the activation of the transcription factors of the E2F type. The cyclins themselves are degraded by the ubiquitin-mediated proteolysis. Activating and inactivating phosphorylations regulate the activities of the CDKs, for example phosphorylate CDK-activating kinases (CAKs) Thr160/161 of the CDK1, while, by contrast, the families of Wee1/Myt1 inactivate kinases CDK1 by phosphorylation of Thr14 and Tyr15. These inactivating phosphorylations can be destroyed in turn by cdc25 phosphatases. The regulation of the activity of the CDK/Cyc complexes by two families of natural CDK inhibitor proteins (CKIs), the protein products of the p21 gene family (p21, p27, p57) and the p16 gene family (p15, p16, p18, p19) is very significant. Members of the p21 family bind to cyclin complexes of CDKs 1, 2, 4, 6, but inhibit only the complexes that contain CDK1 or CDK2. Members of the p16 family are specific inhibitors of the CDK4- and CDK6 complexes.

The plane of control point regulation lies above this complex direct regulation of the activity of the CDKs. Control points allow the cell to track the orderly sequence of the individual phases during the cell cycle. The most important control points lie at the transition from G1 to S and from G2 to M. The G1 control point ensures that the cell does not initiate any DNA synthesis unless it has proper nutrition, interacts correctly with other cells or the substrate, and its DNA is intact. The G2/M control point ensures the complete replication of DNA and the creation of the mitotic spindle before the cell enters into mitosis. The G1 control point is activated by the gene product of the p53 tumor suppressor gene. p53 is activated after detection of changes in metabolism or the genomic integrity of the cell and can trigger either a stopping of the cell cycle progression or apoptosis. In this case, the transcriptional activation of the expression of the CDK inhibitor protein p21 by p53 plays a decisive role. A second branch of the G1 control point comprises the activation of the ATM and Chk1 kinases after DNA damage by UV light or ionizing radiation and finally the phosphorylation and the subsequent proteolytic degradation of the cdc25A phosphatase (Mailand, N. et al. (2000). Rapid Destruction of Human cdc25A in Response to DNA Damage. *Science* 288, 1425-1429). A shutdown of the cell cycle results from this, since the inhibitory phosphorylation of the CDKs is not removed. After the G2/M control point is activated by damage of the DNA, both mechanisms are involved in a similar way in stopping the progression through the cell cycle.

The loss of the regulation of the cell cycle and the loss of function of the control points are characteristics of tumor cells. The CDK-Rb signal path is affected by mutations in over 90% of human tumor cells. These mutations, which finally result in inactivating phosphorylation of the RB, include the over-expression of D- and E-cyclins by gene amplification or chromosomal translocations, inactivating mutations or deletions of CDK inhibitors of the p16 type, as well as increased (p27) or reduced (CycD) protein degradation. The second group of genes, which are affected by mutations in tumor cells, codes for components of the control points. Thus p53, which is essential for the G1 and G2/M control points, is the most frequently mutated gene in human tumors (about 50%). In tumor cells that express p53 without mutation, it is often inactivated because of a greatly increased protein degradation. In a similar way, the genes of other proteins that are necessary for the function of the control points are affected by mutations, for example ATM (inactivating mutations) or cdc25 phosphatases (over-expression).

Convincing experimental data indicate that CDK2/Cyc complexes occupy a decisive position during the cell cycle progression: (1) Both dominant-negative forms of CDK2, such as the transcriptional repression of the CDK2 expression by anti-sense oligonucleotides, produce a stopping of the cell cycle progression. (2) The inactivation of the CycA gene in mice is lethal. (3) The disruption of the function of the CDK2/CycA complex in cells by means of cell-permeable peptides resulted in tumor cell-selective apoptosis (Chen, Y. N. P. et al. (1999). Selective Killing of Transformed Cells by Cyclin/Cyclin-Dependent Kinase 2 Antagonists. *Proc. Natl. Acad. Sci. USA* 96, 4325-4329).

Changes of the cell cycle control play a role not only in carcinoses. The cell cycle is activated by a number of viruses, both by transforming viruses as well as by non-transforming viruses, to make possible the reproduction of viruses in the host cell. The false entry into the cell cycle of normally post-mitotic cells is associated with various neurodegenerative diseases.

The mechanisms of the cell cycle regulation, their changes in diseases and a number of approaches to develop inhibitors of the cell cycle progression and especially the CDKs were already described in a detailed summary in several publications (Sielecki, T. M. et al. (2000). Cyclin-Dependent Kinase Inhibitors: Useful Targets in Cell Cycle Regulation. *J. Med. Chem.* 43, 1-18; Fry, D. W. & Garrett, M. D. (2000). Inhibitors of Cyclin-Dependent Kinases as Therapeutic Agents for the Treatment of Cancer. *Curr. Opin. Oncol. Endo. Metab. Invest. Drugs* 2, 40-59; Rosiania, G. R. & Chang, Y. T. (2000). Targeting Hyperproliferative Disorders with Cyclin-Dependent Kinase Inhibitors. *Exp. Opin. Ther. Patents* 10, 215-230; Meijer, L. et al. (1999). Properties and Potential Applications of Chemical Inhibitors of Cyclin-Dependent Kinases. *Pharmacol. Ther.* 82, 279-284; Senderowicz, A. M. & Sausville, E. A. (2000). Preclinical and Clinical Development of Cyclin-Dependent Kinase Modulators. *J. Natl. Cancer Inst.* 92, 376-387).

To use the compounds according to the invention as pharmaceutical agents, the latter are brought into the form of a pharmaceutical preparation, which in addition to the active ingredient for enteral or parenteral administration contains suitable pharmaceutical, organic or inorganic inert support media, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, or capsules, or in liquid form, for example as solutions, suspensions, or emulsions. Moreover, they optionally contain adjuvants, such as preservatives, stabilizers, wetting agents or emulsifiers; salts for changing the osmotic pressure, or buffers. These pharmaceutical preparations are also subjects of this invention.

For parenteral administration, especially injection solutions or suspensions, especially aqueous solutions of active compounds in polyhydroxyethoxylated castor oil, are suitable.

As carrier systems, surface-active adjuvants such as salts of bile acids or animal or plant phospholipids, but also mixtures thereof as well as liposomes or their components, can also be used.

For oral administration, especially tablets, coated tablets or capsules with talc and/or hydrocarbon vehicles or binders, such as, for example, lactose, corn or potato starch, are suitable. The administration can also be carried out in liquid form, such as, for example, as a juice, to which optionally a sweetener is added.

Enteral, parenteral and oral administrations are also subjects of this invention.

The dosage of the active ingredients can vary depending on the method of administration, age and weight of the patient, type and severity of the disease to be treated and similar factors. The daily dose is 0.5-1000 mg, preferably 50-200 mg, whereby the dose can be given as a single dose to be administered once or divided into two or more daily doses.

In contrast, compounds of general formula I according to the invention can also inhibit receptor tyrosine kinases and their ligands that specifically regulate the function of endothelial cells. Receptor tyrosine kinases and their ligands that specifically regulate the function of endothelial cells are involved decisively in physiological as well as pathogenic angiogenesis. The VEGF/VEGF-receptor system is of special importance here. In pathological situations, which are accompanied by increased neovascularization, an increased expression of angiogenic growth factors and their receptors was found. Most solid tumors thus express large amounts of VEGF, and the expression of the VEGF receptors is preferably considerably increased in the endothelial cells that lie near the tumors or run through the latter (Plate et al., Cancer Res. 53, 5822-5827, 1993). The inactivation of the VEGF/VEGF receptor system by VEGF-neutralizing antibodies (Kim et al., Nature 362, 841-844, 1993), retroviral expression of dominant-negative VEGF-receptor variants (Millauer et al., Nature 367, 576-579, 1994), recombinant VEGF-neutralizing receptor variants (Goldman et al., Proc. Natl. Acad. Sci. USA 95, 8795-8800, 1998), or low-molecular inhibitors of the VEGF-receptor tyrosine kinase (Fong et al., Cancer Res. 59, 99-106, 1999; Wedge et al., Cancer Res. 60, 970-975, 2000; Wood et al., Cancer Res. 60, 2178-2189, 2000) resulted in a reduced tumor growth and a reduced tumor vascularization. Thus, the inhibition of the angiogenesis is a possible treatment method for tumor diseases.

Compounds according to the invention can consequently inhibit either cyclin-dependent kinases, such as CDK1, CDK2, CDK3, CDK4, CDK5, CDK6, CDK7, CDK8 and CDK9, as well as the glycogen-synthase-kinase (GSK-3β) and VEGF-receptor tyrosine kinases or cyclin-dependent kinases or VEGF-receptor tyrosine kinases. These actions contribute to the fact that the compounds according to the invention can be used in the treatment of cancer, angiofibroma, arthritis, eye diseases, auto-immune diseases, chemotherapy agent-induced alopecia and mucositis, Crohn's disease, endometriosis, fibrotic diseases, hemangioma, cardiovascular diseases, infectious diseases, nephrological diseases, chronic and acute neurodegenerative diseases, as well as injuries to the nerve tissue, viral infections, for inhibiting the reocclusion of vessels after balloon catheter treatment, in vascular prosthetics or after mechanical devices are used to keep vessels open, such as, e.g., stents, as immunosuppressive agents, for supporting scar-free healing, in senile keratosis and in contact dermatitis, whereby cancer is defined as solid tumors, tumor or metastastic growth, Kaposi's sarcoma, Hodgkin's disease, and leukemia;

arthritis is defined as rheumatoid arthritis;
eye diseases are defined as diabetic retinopathy, and neovascular glaucoma;
auto-immune diseases are defined as psoriasis, alopecia and multiple sclerosis;

fibrotic diseases are defined as cirrhosis of the liver, mesangial cell proliferative diseases, and arteriosclerosis;

infectious diseases are defined as diseases that are caused by unicellular parasites;

cardiovascular diseases are defined as stenoses, such as, e.g., stent-induced restenoses, arterioscleroses and restenoses;

nephrological diseases are defined as glomerulonephritis, diabetic nephropathy, malignant nephrosclerosis, thrombic microangiopathic syndrome, transplant rejections and glomerulopathy;

chronic neurodegenerative diseases are defined as Huntington's disease, amyotrophic lateral sclerosis, Parkinson's disease, AIDS dementia and Alzheimer's disease;

acute neurodegenerative diseases are defined as ischemias of the brain and neurotraumas;

and viral infections are defined as cytomegalic infections, herpes, hepatitis B or C, and HIV diseases.

Subjects of this invention are also pharmaceutical agents for treating the above-cited diseases, which contain at least one compound according to general formula (I), as well as pharmaceutical agents with suitable formulation substances and vehicles.

The compounds of general formula I according to the invention are, i.a., excellent inhibitors of the cyclin-dependent kinases, such as CDK1, CDK2, CDK3, CDK4, CDK5, CDK6, CDK7, CDK8 and CDK9, as well as the glycogen-synthase-kinase (GSK-3β).

The intermediate products of general formula (IIa) or (IIb), preferably used for the production of the compounds of general formula I according to the invention,

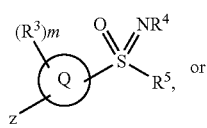
(IIa)

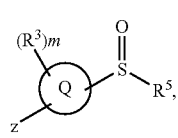
(IIb)

in which Z stands for —NH$_2$ or NO$_2$ and m, R$^3$, R$^4$ and R$^5$ have the meanings that are indicated in general formula (I), as well as their isomers, diastereomers, enantiomers and salts as intermediate products, are also subjects of this invention.

The intermediate products of general formula (IIIa), (IIIb) or (IIIc), also preferably used for the production of the compounds of general formula I according to the invention,

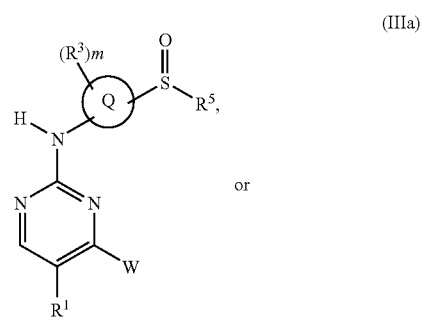
(IIIa)

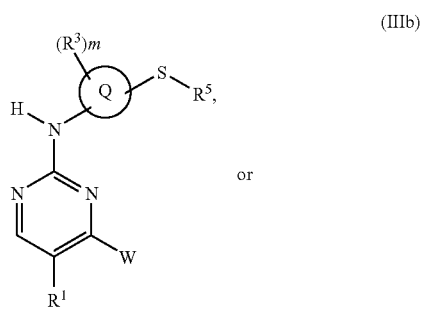
(IIIb)

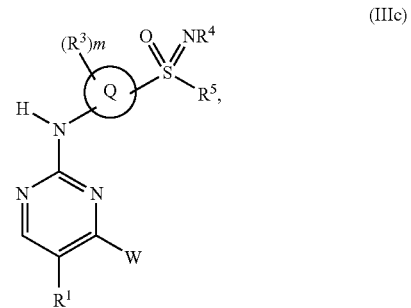
(IIIc)

in which W stands for halogen, hydroxy or X—R$^2$, and R$^1$, R$^2$, R$^3$, R$^5$, m and X have the meanings that are indicated in general formula (I), as well as their isomers, diastereomers, enantiomers, and salts as intermediate products for the production of the compound of general formula (I).

Intermediate products of general formula (IV), preferably used for the production of the compounds of general formula (I) according to the invention,

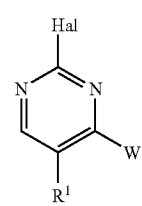
(IV)

in which

Hal stands for halogen, W stands for halogen, hydroxy, or X—R², and R¹, R², and X have the meanings that are indicated in general formula (I), as well as their isomers, diastereomers, enantiomers and salts, are also subjects of this invention.

If the production of the starting compounds is not described, the latter are known or can be produced in a way that is similar to known compounds or to processes that are described here. It is also possible to perform all reactions that are described here in parallel reactors or by means of combinatory operating procedures.

The isomer mixtures can be separated into enantiomers or E/Z isomers according to commonly used methods, such as, for example, crystallization, chromatography or salt formation.

The production of salts is carried out in the usual way by a solution of the compound of formula I being mixed with the equivalent amount of or an excess of a base or acid, which optionally is in solution, and the precipitate being separated or the solution being worked up in the usual way.

Production of the Compounds According to the Invention

One of the most important methods for the production of sulfoximines is the reaction of a sulfoxide with hydrazoic acid, which is produced in situ, e.g., from the reaction of sodium azide and concentrated sulfuric acid (M. Reggelin, C. Zur, *Synthesis* 2000, 1, 1). The reaction can be performed in an organic solvent, such as chloroform. Other methods for the synthesis of sulfoximines are, e.g., the reactions of sulfoxides with a) TsN₃ ((a) R. Tanaka, K. Yamabe, *J. Chem. Soc. Chem. Commun.* 1983, 329; (b) H. Kwart, A. A. Kahn, *J. Am. Chem. Soc.* 1967, 89, 1959)).

b) N-Tosylimino Phenyl Iodinane and Cat. Amounts of Cu(I)triflate (J. F. K. Müller, P. Vogt, *Tetrahedron Lett.* 1998, 39, 4805)

c) Boc-azide and Cat. Amounts of Iron(II) Chloride (T. Bach, C. Korber, *Tetrahedron Lett.* 1998, 39, 5015) or d) o-Mesitylenesulfonylhydroxylamine (MSH) (C. R. Johnson, R. A. Kirchhoff, H. G. Corkins, *J. Org. Chem.* 1974, 39, 2458).

e) [N-(2-(Trimethylsilyl)ethanesulfonyl)imino]phenyliodinane (PhI=NSes) (S. Cren, T. C. Kinahan, C. L. Skinner and H. Tye, *Tetrahedron Lett.* 2002, 43, 2749).

In terms of structure and configuration, sulfoximines generally have a high stability (C. Bolm, J. P. Hildebrand, *J. Org. Chem.* 2000, 65, 169). These properties of the functional group often also allow drastic reaction conditions and make possible the simple derivatization of the sulfoximines in the imine-nitrogen and α-carbon. Enantiomer-pure sulfoximines are also used as auxiliaries in the diastereoselective synthesis ((a) S. G. Pyne, *Sulfur Reports* 1992, 12, 57; (b) C. R. Johnson, *Aldrichchimica Acta* 1985, 18, 3). The production of enantiomer-pure sulfoximines is described, e.g., via the racemate cleavage with enantiomer-pure camphor-10-sulfonic acid ((a) C. R. Johnson, C. W. Schroeck, *J. Am. Chem. Soc.* 1973, 95, 7418; (b) C. S. Shiner, A. H. Berks, *J. Org. Chem.* 1988, 53, 5543). Another method for producing optically active sulfoximines consists in the stereoselective imination of optically active sulfoxides with use of MSH ((a) C. Bolm, P. Müller, K. Harms, *Acta Chem. Scand.* 1996, 50, 305; (b) Y. Tamura, J. Minamikawa, K. Sumoto, S. Fujii, M. Ikeda, *J. Org. Chem.* 1973, 38, 1239).

The following examples explain the production of the compounds according to the invention without limiting the scope of the claimed compounds to these examples.

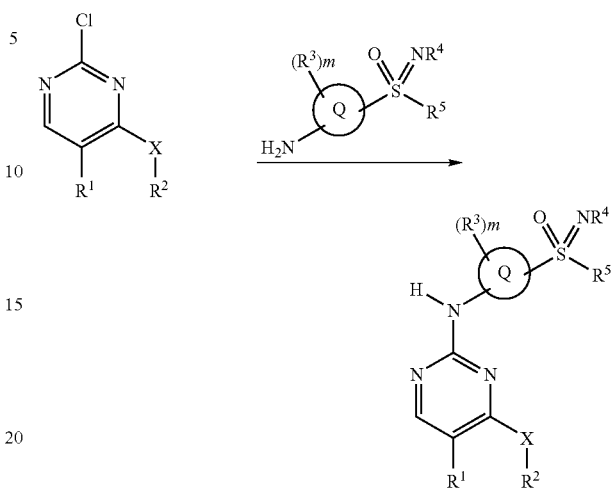

The substituents Q, R¹, R², R³, R⁴, R⁵ and m have the meaning that is indicated in general formula (I).

EXAMPLE 1.0

Production of (RS)-S-[4-({5-Bromo-4-[(R)-(2-hydroxy-1-methylethyl)amino]pyridimin-2-yl}amino)phenyl]-S-methyl sulfoximide

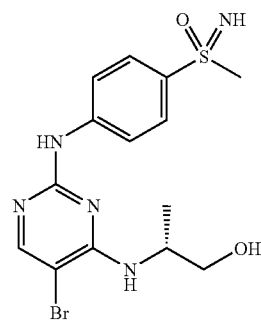

Method A 40 mg (0.23 mmol) of (RS)-S-(4-aminophenyl)-S-methyl sulfoximide and 62 mg (0.23 mmol) of (R)-2-[(5-bromo-2-chloropyrimidin-4-yl)amino]propan-1-ol are mixed under argon with 0.5 ml of 1-butyl-3-methyl-imidazolium tetrafluoroborate (survey article on ionic liquids: a) T. Welton, *Chem. Rev.* 1999, 99, 2071 b) H. Zhao, *Aldrichimica Acta* 2002, 35, 75 c) M. J. Earle, K. R. Seddon, *ACS Symposium Series* 2002, 819, 10) and stirred for 10 minutes at room temperature. The reaction mixture is heated to 60° C. and stirred for another 3 hours at this temperature. It is mixed with 0.08 ml of a 4 molar solution of hydrochloric acid in dioxane and stirred for 60 hours at 60° C. After cooling, the reaction mixture is mixed with 10 ml of ethyl acetate and stirred for 10 minutes. The organic solvent is decanted, and the residue is dissolved in 10 ml of methanol. It is mixed with 200 ml of ethyl acetate and then washed with 50 ml of a saturated NaCl solution. The organic phase is dried (Na₂SO₄), filtered and concentrated by evaporation. The remaining residue is purified by chromatography (DCM/ethanol, 8:2). 23 mg (0.06 mmol, corresponding to 26% of theory) of the product is obtained.

Method B

A solution of 267 mg (1.0 mmol) of (R)-2-[(5-bromo-2-chloropyrimidin-4-yl)amino]propan-1-ol in 2 ml of acetonitrile is added at room temperature to 171 mg (1.0 mmol) of (RS)-S-(4-aminophenyl)-S-methyl sulfoximide in 1 ml of acetonitrile. The batch is mixed with 0.25 ml of a 4 molar solution of hydrochloric acid in dioxane and stirred under reflux overnight. The solvent is drawn off, and the remaining residue is purified by chromatography (DCM/EtOH 8:2). The crude product that is obtained is finally purified by HPLC:

| Column: | Luna C18(2) 5μ |
| Length × ID: | 150 × 21.2 mm |
| Eluants: | A = H₂O, B = ACN, A/0.5 g of NH₄Ac/l |
| Flow: | 10.0 ml/min |
| Gradient: | 5 → 100% B(5') – 5 → 100% B(30') + 100% B(5') |
| Detector: | PDA 214 nm |
| Temperature: | 21° C. |
| RT in min: | 20.3 |

53 mg (0.13 mmol, corresponding to 13% of theory) of the product is obtained.

¹H-NMR (DMSO): 9.71 (s, 1H), 8.11 (s, 1H), 7.91 (d, 2H), 7.78 (d, 2H), 6.41 (d, 1H), 4.89 (t, 1H), 4.25 (m, 1H), 3.96 (br, 1H), 3.53 (m, 2H), 3.03 (s, 3 H), 1.21 (d, 3H). MS: 400 (ES).

EXAMPLE 1.1

Production of (RS)-S-[3-({5-bromo-4-[(R)-(2-hydroxy-1-methylethyl)amino]pyrimidin-2-yl}amino)phenyl]-S-methyl-N-nitrosulfoximide

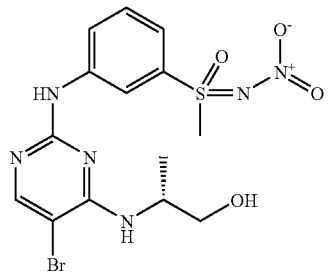

A solution of 37 mg (0.17 mmol) of (RS)-S-(3-aminophenyl)-S-methyl-N-nitrosulfoximide in 3 ml of acetonitrile is mixed with 91 mg (0.34 mmol) of (R)-2-[(5-bromo-2-chloropyrimidin-4-yl)amino]propan-1-ol and 0.06 ml of a 4 molar solution of hydrochloric acid in dioxane, and it is stirred under reflux overnight. Another 0.05 ml of the 4 molar solution of hydrochloric acid in dioxane is added, and it is refluxed for another 6 hours. After TLC monitoring, it is mixed again with 92 mg (0.34 mmol) of (R)-2-[(5-bromo-2-chloropyrimidin-4-yl)amino]propan-1-ol and refluxed overnight. After cooling, the batch is made basic with saturated NaHCO₃ solution and extracted from ethyl acetate. The combined organic phases are dried (Na₂SO₄), filtered and concentrated by evaporation. The residue that is obtained is purified by chromatography (DCM/EtOH 95:5).

24 mg (0.05 mmol, corresponding to 32% of theory) of the product is obtained (diastereomers A/B 1:1).

¹H-NMR (DMSO): 9.85 (s, 2H, A+B), 8.73 (m, 1H, A), 8.69 (m, 1H, B), 8.11 (s, 1H, A), 8.10 (s, 1H, B), 7.92 (m, 2H, A+B), 7.58 (m, 4H, A+B), 6.40 (m, 2H, A+B), 4.86 (t, 2H, A+B), 4.32 (m, 2H, A+B), 3.68 (s, 3H, A), 3.66 (s, 3H, B), 3.55 (m, 4H, A+B), 1.23 (d, 3H, A), 1.21 (d, 3H, B). MS: 445 (ES).

Produced in a way similar to the above-described process variants are also the compounds below:

EXAMPLE 1.2

Production of (RS)-S-[4-({5-bromo-4-[(1R,2R)-(2-hydroxy-1-methylpropyl)amino]pyridimin-2-yl}amino)phenyl]-S-methyl sulfoximide

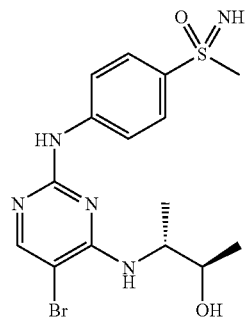

¹H-NMR (DMSO): 9.73 (s, 1H), 8.12 (s, 1H), 7.91 (d, 2H), 7.86 (d, 2H), 6.14 (d, 1H), 5.02 (br, 1H), 4.09 (m, 1H), 3.97 (s, 1H), 3.78 (m, 1H), 3.02 (s, 3 H), 1.25 (d, 3H), 1.09 (d, 3H). MS: 414 (ES).

EXAMPLE 1.3

Production of (RS)-S-[4-({5-bromo-4-[(R)-(2-hydroxy-1,2-dimethylpropyl)amino]pyrimidin-2-yl}amino)phenyl]-S-methyl sulfoximide

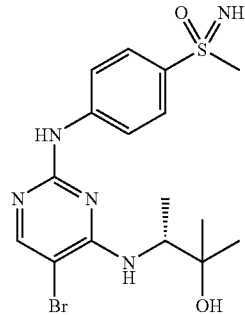

¹H-NMR (DMSO): 9.72 (s, 1H), 8.11 (s, 1H), 7.90 (d, 2H), 7.78 (d, 2H), 6.10 (d, 1H), 4.87 (s, 1H), 4.07 (m, 1H), 3.98 (s, 1H), 3.01 (s, 3H), 1.19 (m, 9H). MS: 428 (ES).

EXAMPLE 1.4

Production of (RS)-S-[4-({5-bromo-4-[(1R,2R)-2-hydroxy-1-methylpropoxy]pyrimidin-2-yl}amino)phenyl]-S-methyl sulfoximide

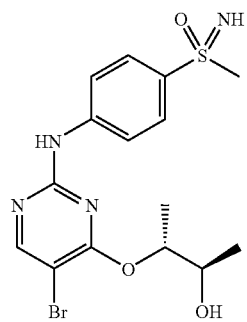

¹H-NMR (DMSO): 10.12 (s, 1H), 8.45 (s, 1H), 7.92 (d, 2H), 7.84 (d, 2H), 5.21 (m, 1H), 4.91 (d, 1H), 4.04 (s, 1H), 3.87 (m, 1H), 3.03 (s, 3H), 1.28 (d, 3 H), 1.13 (d, 3H). MS: 415 (ES).

EXAMPLE 1.5

Production of (RS)-S-[4-({5-bromo-4-[(R)-(2-hydroxy-1,2-dimethylpropyl)amino]pyrimidin-2-yl}amino)phenyl]-S-cyclopropyl-N-[2-(trimethylsilyl)ethylsulfonyl]sulfoximide

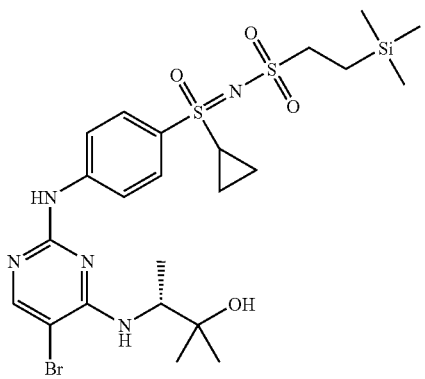

95 mg (0.32 mmol) of (R)-3-[(5-bromo-2-chloropyrimidin-4-yl)amino]-2-methyl-butan-2-ol is dissolved in 2 ml of acetonitrile and mixed with 116 mg (0.32 mmol) of (RS)-S-(4-aminophenyl)-S-cyclopropyl-N-[2-(trimethylsilyl)ethylsulfonyl]sulfoximide. After 0.08 ml of an approximately 4N solution of HCl in dioxane and 0.08 ml of water are added, the mixture is heated in a sealed vessel for 16 hours to 75° C. The suspension is filtered, and the filtrate is separated by flash chromatography (dichloromethane-dichloromethane/ethanol 95:5, 15 ml/min). The fractions, 43-51 min, contain 50 mg (25% of theory) of the desired product.

¹H-NMR (DMSO): 9.91 (s, 1H), 8.16 (s, 1H), 8.01 (d, 2H), 7.83 (d, 2H), 6.14 (d, 1H), 4.87 (s, 1H), 4.10 (m, 1H), 3.18 (m, 1H), 2.92 (m, 2H), 1.37-1.00 (m, 4H), 1.21 (s, 3H), 1.20 (d, 3H), 1.14 (s, 3H), 0.93 (m, 2H), 0.01 (s, 9H). MS: 618/620 (100%, ES).

EXAMPLE 1.6

Production of (RS)-S-[4-({5-bromo-4-[(R)-(2-hydroxy-1,2-dimethylpropyl)amino]pyrimidin-2-yl}amino)phenyl]-S-cyclopropylsulfoximide Method C

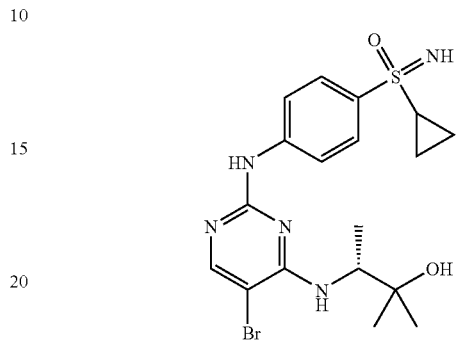

50 mg of (RS)-S-[4-({5-bromo-4-[(R)-(2-hydroxy-1,2-dimethylpropyl)amino]-pyrimidin-2-yl}amino)phenyl]-S-cyclopropyl-N-[2-(trimethylsilyl)ethylsulfonyl]-sulfoximide is dissolved in 1 ml of tetrahydrofuran and mixed with 0.3 ml of a 1 M solution of tetrabutylammonium fluoride in tetrahydrofuran. The mixture is stirred for 3 days at 50° C. and purified by flash chromatography (dichloromethane-dichloromethane/ethanol 9:1). 10 mg (28% of theory) of the product is obtained.

¹H-NMR (DMSO): 9.72 (s, 1H), 8.13 (s, 1H), 7.90 (d, 2H), 7.74 (d, 2H), 6.10 (d, 1H), 4.86 (s, 1H), 4.10 (m, 1H), 3.95 (s, 1H), 3.16 (m, 1H), 1.40-1.00 (m, 4H), 1.20 (s, 3H), 1.19 (d, 3H), 1.15 (s, 3H). MS: 454/456 (20%, ES).

Produced in a way similar to the above-described process variants are also the compounds below.

EXAMPLE 1.7

Production of (RS)-S-[4-({5-bromo-4-[(R)-(2-hydroxy-1-methylethyl)amino]pyrimidin-2-yl}amino)phenyl]-S-(cyclopropylmethyl)-N-[2-(trimethylsilyl)ethylsulfonyl]sulfoximide

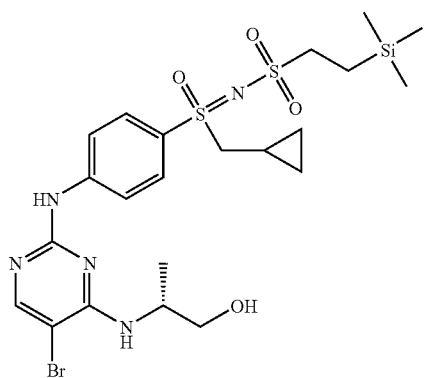

¹H-NMR (DMSO): 10.33 (s, 1H), 8.23 (s, 1H), 8.01 (d, 2H), 7.88 (d, 2H), 7.02 (d, 1H), 5.58 (s br, 1H), 4.28 (m, 1H), 3.67 (d, 2H), 3.55 (m, 2H), 2.98 (m, 2 H), 1.21 (d, 3H), 0.97 (m, 2H), 0.86 (m, 1H), 0.44 (m, 2H), 0.12 (m, 2H), 0.01 (s, 9H) MS: 604/606 (100%, ES). Melting point: 195° C. (dec.).

EXAMPLE 1.8

Production of (RS)-S-[4-({5-bromo-4-[(R)-(2-hydroxy-1,2-dimethylpropyl)amino]pyrimidin-2-yl}amino)phenyl]-S-(cyclopropylmethyl)-N-[2-(trimethylsilyl)ethylsulfonyl]sulfoximide

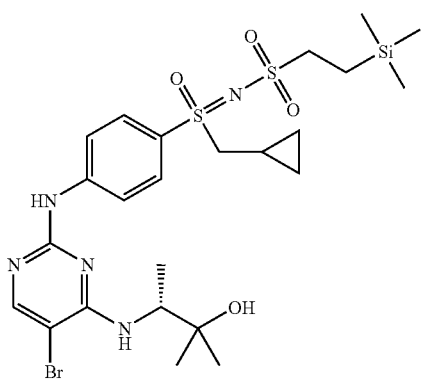

¹H-NMR (DMSO): 9.93 (s, 1H), 8.16 (s, 1H), 8.02 (d, 2H), 7.83 (d, 2H), 6.14 (d, 1H), 4.87 (s, 1H), 4.10 (m, 1H), 3.64 (d, 2H), 2.96 (m, 2H), 1.21 (s, 3H), 1.20 (d, 3H), 1.15 (s, 3H), 0.98 (m, 2H), 0.87 (m, 1H), 0.46 (m, 2H), 0.13 (m, 2H), 0.02 (s, 9H). MS: 632/634 (40%, ES).

EXAMPLE 1.9

Production of (RS)-S-[4-({5-bromo-4-[(R)-(2-hydroxy-1,2-dimethylpropyl)amino]pyrimidin-2-yl}amino)phenyl]-S-(cyclopropylmethyl)sulfoximide

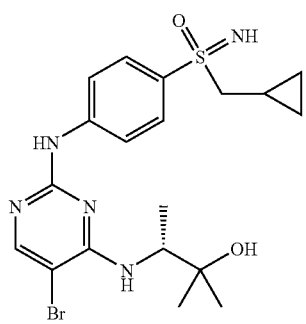

¹H-NMR (DMSO): 9.73 (s, 1H), 8.13 (s, 1H), 7.92 (d, 2H), 7.75 (d, 2H), 6.10 (d, 1H), 4.85 (s, 1H), 4.10 (m, 1H), 3.92 (s, 1H), 3.02 (m, 2H), 1.20 (s, 3H), 1.19 (d, 3H), 1.14 (s, 3H), 0.87 (m, 1H), 0.37 (m, 2H), 0.00 (m, 2H).

EXAMPLE 1.10

Production of (RS)-S-[4-({5-bromo-4-[(R)-(2-hydroxy-1,2-dimethylpropyl)amino]pyrimidin-2-yl}amino)phenyl]-S-cyclopentyl-N-[2-(trimethylsilyl)ethylsulfonyl]sulfoximide

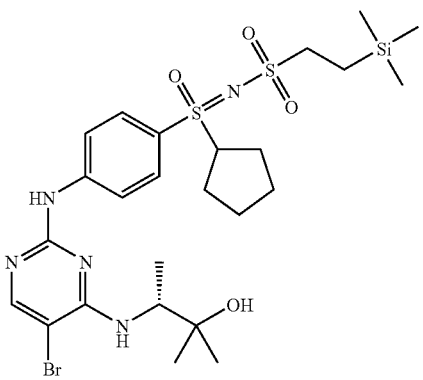

Melting point: 200-201° C.

EXAMPLE 1.11

Production of (RS)-S-[4-({5-bromo-4-[(R)-(2-hydroxy-1,2-dimethylpropyl)amino]pyrimidin-2-yl}amino)phenyl]-S-cyclopentylsulfoximide

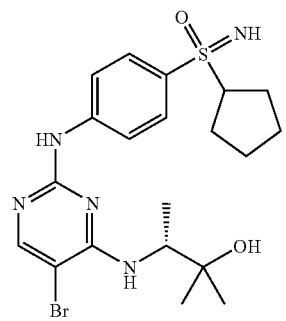

Melting point: 194-196° C.

1.12) Production of (RS)-S-[4-({5-bromo-4-[(R)-(2-hydroxy-1,2-dimethylpropyl)amino]pyrimidin-2-yl}amino)phenyl]-S-(2-hydroxyethyl)-N-[2-(trimethylsilyl)ethylsulfonyl]sulfoximide

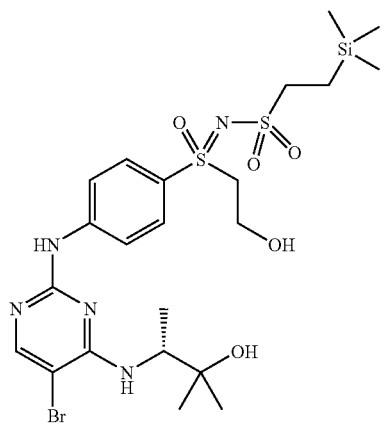

A solution of 200 mg (0.55 mmol) of (RS)-S-(4-aminophenyl)-S-(2-hydroxyethyl)-N-[2-(trimethylsilyl)ethylsulfonyl]sulfoximide in 2 ml of acetonitrile and 0.5 ml of water is mixed with 0.17 ml of a 4N solution of HCl in dioxane. 198 mg (0.67 mmol) of (R)-3-[(5-bromo-2-chloropyrimidin-4-yl)amino]-2-methyl-butan-2-ol in 1.5 ml of acetonitrile is added, and the batch is stirred for 20 hours at 80° C. The solvent is removed, and the remaining residue is purified by chromatography (DCM/EtOH 9: 1). 148 mg (0.24 mmol, corresponding to 44% of theory) of the product is obtained.

¹H-NMR (DMSO): 10.21 (s, 1H), 8.21 (s, 1H), 7.97 (m, 2H), 7.85 (m, 2H), 6.42 (d, 1H), 4.10 (m, 1H), 3.80 (m, 2H), 3.70 (m, 2H), 2.95 (m, 2H), 1.20 (m, 9 H), 0.96 (m, 2H), 0.03 (s, 9H).

EXAMPLE 1.13

Production of (RS)-S-[4-({5-bromo-4-[(R)-(2-hydroxy-1,2-dimethylpropyl)amino]pyrimidin-2-yl}amino)phenyl]-S-(2-hydroxyethyl)sulfoximide

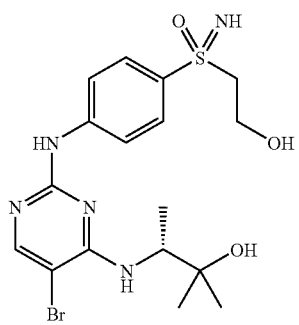

¹H-NMR (DMSO): 9.75 (s, 1H), 8.13 (s, 1H), 7.91 (m, 2H), 7.75 (m, 2H), 6.12 (d, 1H), 4.85 (m, 2H), 4.11 (m, 2H), 3.65 (m, 2H), 3.23 (m, 2H), 1.17 (m, 9H).

The diastereomer mixture that is obtained is cleaved into pure diastereomers by means of preparatory HPLC.

| Column: | Chiralpak AD 20µ |
|---|---|
| Length × ID: | 250 × 60 mm |
| Eluants: | Hexane/ethanol 70:30 |
| Flow: | 80 ml/min |
| Detector: | UV 300 nm |
| Temperature: | Room temperature |
| RT in min: | 23.41; Diastereomer 1 (Example 1.14) |
| | 54.16; Diastereomer 2 (Example 1.15) |

1.16) Production of (RS)-S-[4-({5-Bromo-4-[(1R,2R)-(2-hydroxy-1-methyl-propyl)amino]pyrimidin-2-yl}amino)phenyl]-S-(2-hydroxyethyl)-N-[2-(trimethylsilyl)ethylsulfonyl]sulfoximide

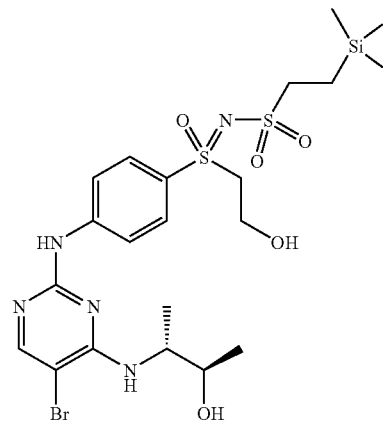

¹H-NMR (DMSO): 10.53 (s, 1H), 8.28 (s, 1H), 7.95 (m, 2H), 7.88 (m, 2H), 6.86 (d, 1H), 4.13 (m, 1H), 3.76 (m, 5H), 2.90 (m, 2H), 1.25 (d, 3H), 1.11 (d, 3 H), 0.93 (m, 2H), 0.03 (s, 9H).

1.17) Production of (RS)-S-[4-({5-bromo-4-[(1R,2R)-(2-hydroxy-1-methyl-propyl)amino]pyrimidin-2-yl}amino)phenyl]-S-(2-hydroxyethyl)sulfoximide

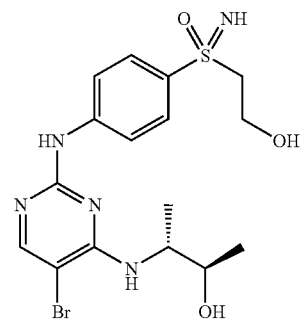

¹H-NMR (DMSO): 9.75 (s, 1H), 8.11 (s, 1H), 7.92 (m, 2H), 7.72 (m, 2H), 6.14 (d, 1H), 5.02 (d, 1H), 4.85 (tr, 1H), 4.10 (m, 2H), 3.78 (m, 1H), 3.62 (m, 2 H), 3.22 (m, 2H), 1.23 (d, 3H), 1.08 (d, 3H). MS: 444 (ES).

The diastereomer mixture that is obtained is cleaved into the pure diastereomers by means of preparatory HPLC:

| Column: | Chiralpak AD-H 5μ |
| --- | --- |
| Length × ID: | 250 × 20 mm |
| Eluants: | A: Hexane, C: Ethanol |
| Flow: | 10 ml/min |
| Gradient: | Isocratic 50% C |
| Detector: | UV 300 nm |
| Temperature: | Room temperature |
| RT in min: | 13.1; Diastereomer 1 (Example 1.18) |
| | 18.9; Diastereomer 2 (Example 1.19) |

1.20) Production of (RS)-S-[4-({5-bromo-4-[(1R, 2R)-2-hydroxy-1-methyl-propoxy]pyrimidin-2-yl}amino)phenyl]-S-(2-hydroxyethyl)-N-[2-(trimethylsilyl)ethylsulfonyl]sulfoximide

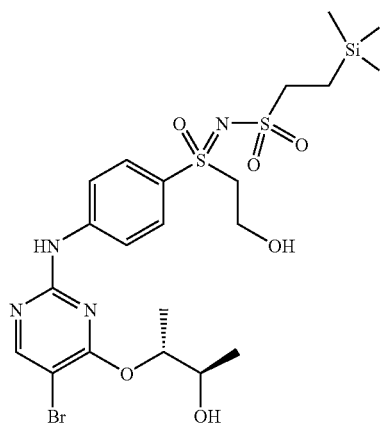

A solution of 205 mg (0.56 mmol) of (RS)-S-(4-aminophenyl)-S-(2-hydroxyethyl)-N-[2-(trimethylsilyl)ethylsulfonyl]sulfoximide in 2 ml of acetonitrile is mixed with 0.15 ml of a 4N solution of HCl in dioxane. 175 mg (0.62 mmol) of (2R,3R)-3-[(5-bromo-2-chloropyrimidin-4-yl)oxy]-butan-2-ol in 2 ml of acetonitrile is added, and the batch is stirred for 24 hours at 70° C. Then, it is stirred for another 24 hours at 85° C. The solvent is removed, and the remaining residue is purified by chromatography (DCM/EtOH 9:1). 110 mg (0.18 mmol, corresponding to 32% of theory) of the product is obtained.

¹H-NMR (DMSO): 10.31 (s, 1H), 8.45 (s, 1H), 7.99 (m, 2H), 7.83 (m, 2H), 5.25 (m, 1H), 4.93 (m, 2H), 3.75 (m, 5H), 2.90 (m, 2H), 1.32 (d, 3H), 1.13 (d, 3 H), 0.93 (m, 2H), 0.05 (s, 9H). MS: 609 (ES).

1.21) Production of (RS)-S-[4-({5-bromo-4-[(1R, 2R)-2-hydroxy-1-methyl-propoxy]pyrimidin-2-yl}amino)phenyl]-S-(2-hydroxyethyl)sulfoximide

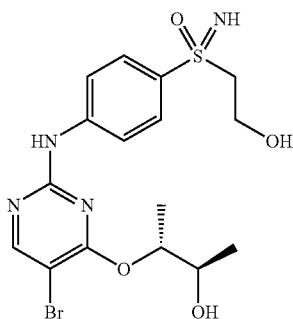

| Column: | Kromasil C8 5μ |
| --- | --- |
| Length × ID: | 125 × 20 mm |
| Eluants: | A: H₂O + 0.1% NH₃, B: ACN |
| Flow: | 15 ml/min |
| Gradient: | 24 –> 38% B(10') –> 95(1') |
| Detector: | UV 300 nm |
| Temperature: | Room temperature |
| RT in min: | 10.9 |

¹H-NMR (DMSO): 10.10 (s, 1H), 8.42 (s, 1H), 7.88 (m, 2H), 7.77 (m, 2H), 5.23 (m, 1H), 4.88 (d, 1H), 4.85 (tr, 1H), 4.18 (s, 1H), 3.84 (m, 1H), 3.63 (m, 2H), 3.22 (m, 2H), 1.28 (d, 3H), 1.14 (d, 3H). MS: 445 (ES).

EXAMPLE 1.22

Production of (RS)-S-[3-({5-bromo-4-[(R)-(2-hydroxy-1,2-dimethylpropyl)amino]pyrimidin-2-yl}amino)phenyl]-S-methyl sulfoximide 127 mg (0.43 mmol) of (R)-3-[(5-bromo-2-chloropyrimidin-4-yl)amino]-2-methyl-butan-2-ol in 1 ml of acetonitrile is added to 74 mg (0.43 mmol) of (RS)-S-(3-aminophenyl)-S-methyl sulfoximide in 0.5 ml of acetonitrile. It is mixed with 0.1 ml of a 4N solution of HCl in dioxane, and the batch is refluxed overnight. The solvent is drawn off, and the remaining residue is purified by chromatography (DCM/EtOH 9: 1). 37 mg (0.09 mmol, corresponding to 20% of theory) of the product is obtained.

¹H-NMR (DMSO): 9.65 (s, 1H), 8.75 (m, 1H), 8.08 (s, 1H), 7.64 (m, 1H), 7.42 (m, 2H), 6.04 (m, 1H), 4.82 (br, 1H), 4.20 (m, 1H), 4.06 (m, 1H), 3.03 (s, 3H), 1.18 (m, 9H). MS: 428 (ES).

EXAMPLE 1.23

Production of (RS)-S-[4-({5-bromo-4-[(R)-(2-hydroxy-1,2-dimethylpropyl)amino]pyrimidin-2-yl}amino)-2-methoxyphenyl]-S-methyl sulfoximide

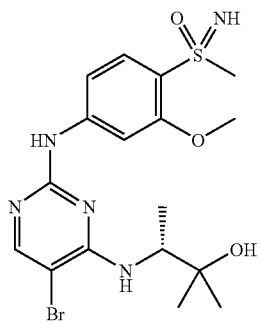

¹H-NMR (DMSO): 9.32 (s, 1H), 8.49 (m, 1H), 8.02 (s, 1H), 7.64 (m, 1H), 7.15 (m, 1H), 5.97 (d, 1H), 4.81 (s, 1H), 4.19 (m, 1H), 4.06 (m, 1H), 3.87 (s, 3 H), 3.15 (s, 3H), 1.15 (m, 9H). MS: 458 (ES).

EXAMPLE 1.24

Production of (RS)-S-[4-({5-bromo-4-[(1R,2R)-2-hydroxy-1-methylpropoxy]pyrimidin-2-yl}amino)-2-methoxyphenyl]-S-methyl sulfoximide

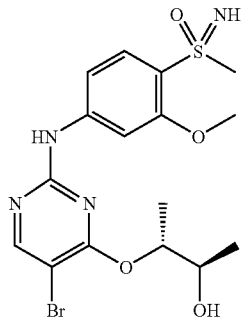

220 mg (1.1 mmol) of (RS)-S-(4-amino-2-methoxyphenyl)-S-methyl sulfoximide and 280 mg (1.0 mmol) of (2R, 3R)-3-[(5-bromo-2-chloropyrimidin-4-yl)oxy]-butan-2-ol in 10 ml of acetonitrile are mixed with 0.28 ml of a 4N solution of HCl in dioxane and stirred under reflux overnight. It is mixed with 1 ml of a solution of n-butanol/methanol (9:1) and stirred under reflux for another 5 days. The batch is concentrated by evaporation, and the residue is purified by chromatography (DCM/ethanol 8:2). 36 mg (0.1 mmol, corresponding to 8% of theory) of the product is obtained.

¹H-NMR (DMSO): 9.81 (s, 1H), 8.32 (m, 2H), 7.71 (m, 1H), 7.18 (m, 1H), 5.25 (m, 1H), 4.95 (br, 1H), 4.18 (m, 1H), 3.91 (s, 3H), 3.83 (m, 1H), 3.15 (s, 3H), 1.25 (m, 3H), 1.10 (m, 3H). MS: 445 (ES).

EXAMPLE 1.25

Production of (RS)-S-[4-({5-bromo-4-[(1R,2R)-(2-hydroxy-1-methylpropyl)amino]pyrimidin-2-yl}amino)-2-methoxyphenyl]-S-methyl sulfoximide

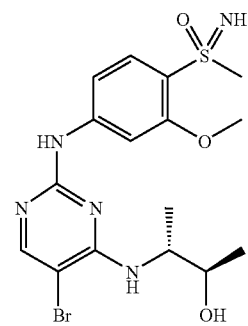

¹H-NMR (DMSO): 9.37 (s, 1H), 8.43 (m, 1H), 8.02 (s, 1H), 7.70 (m, 1H), 7.14 (m, 1H), 5.98 (d, 1H), 5.01 (d, 1H), 4.20 (m, 1H), 4.07 (s, 1H), 3.87 (s, 3 H), 3.75 (m, 1H), 3.14 (s, 3H), 1.15 (d, 3H), 1.07 (d, 3H). MS: 444 (ES).

The diastereomer mixture that is obtained is cleaved into pure diastereomers by means of preparatory HPLC:

| | |
|---|---|
| Column: | Chiralpak AD 20μ |
| Length × ID: | 250 × 60 mm |
| Eluants: | A = Hexane, B = ethanol |
| Flow: | 80 ml/min |
| Gradient: | Isocratic 50% B |
| Detector: | UV 280 nm |
| Temperature: | Room temperature |
| RT in min: | 20.3; Diastereomer 1 (Example 1.26) |
| | 34.8; Diastereomer 2 (Example 1.27) |

EXAMPLE 1.28

Production of (RS)-S-[4-({5-bromo-4-[(1R,2R)-(2-hydroxy-1-methylpropyl)amino]pyrimidin-2-yl}amino)phenyl]-N,S-dimethyl-sulfoximide

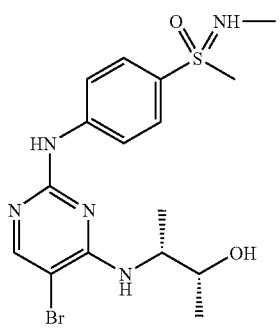

¹H-NMR (DMSO): 9.73 (s, 1H), 8.11 (s, 1H), 7.96 (m, 2H), 7.65 (m, 2H), 6.14 (d, 1H), 5.01 (d, 1H), 4.10 (m, 1H), 3.79 (m, 1H), 3.05 (s, 3H), 2.46 (s, 3H), 1.25 (d, 3H), 1.12 (d, 3H). MS: 428 (ES)

The diastereomer mixture that is obtained is cleaved into the pure diastereomers by means of preparatory HPLC:

| | |
|---|---|
| Column: | Chiralpak AD-H 5μ |
| Length × ID: | 250 × 4.6 mm |
| Eluants: | A = Hexane, B = Ethanol A/0.1% DEA |
| Flow: | 15 ml/min |
| Gradient: | Isocratic 15% B |
| Detector: | UV 300 nm |
| Temperature: | Room temperature |
| RT in min: | 25.45; Diastereomer 1 (Example 1.29) |
| | 29.32; Diastereomer 2 (Example 1.30) |

EXAMPLE 1.31

Production of (RS)-S-[4-({5-bromo-4-[(R)-(2-hydroxy-1,2-dimethylpropyl)amino]pyrimidin-2-yl}amino)phenyl]-N-(ethoxycarbonyl)-S-methyl sulfoximide

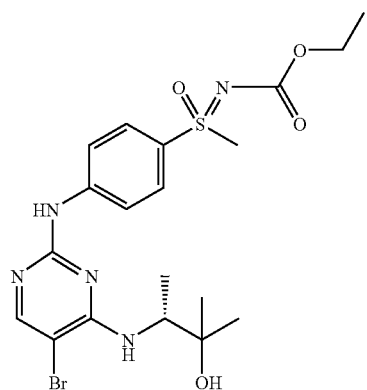

600 mg (2.48 mmol) of (RS)-S-(4-aminophenyl)-N-(ethoxycarbonyl)-S-methyl sulfoximide and 610 mg (2.07 mmol) of (R)-3-[(5-bromo-2-chloropyrimidin-4-yl)amino]-2-methyl-butan-2-ol in 8 ml of acetonitrile are mixed with 0.52 ml of water and 0.52 ml of a 4N solution of HCl in dioxane. The batch is stirred for 24 hours at 60° C. and then concentrated by evaporation. The remaining residue is purified by chromatography (DCM/EtOH 8:2). 649 mg (1.30 mmol, corresponding to 53% of theory) of the product is obtained.

$^1$H-NMR (DMSO): 10.10 (s, 1H), 8.20 (s, 1H), 7.97 (m, 2H), 7.85 (m, 2H), 6.39 (d, 1H), 4.10 (m, 1H), 3.91 (m, 2H), 3.30 (s, 3H), 1.10 (m, 12H).

EXAMPLE 1.32

Production of (RS)-S-[4-({5-bromo-4-[(1R,2R)-(2-hydroxy-1-methylpropyl)amino]pyrimidin-2-yl}amino)phenyl]-N-(ethoxycarbonyl)-S-methyl sulfoximide

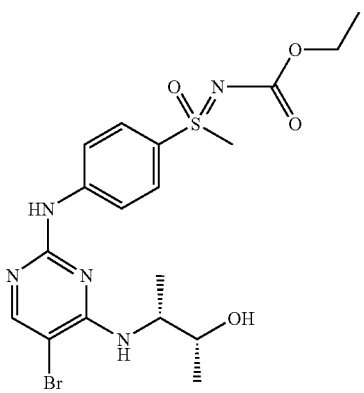

$^1$H-NMR (DMSO): 9.88 (s, 1H), 8.13 (s, 1H), 7.98 (m, 2H), 7.79 (m, 2H), 6.18 (d, 1H), 5.01 (d, 1H), 4.10 (m, 1H), 3.90 (q, 2H), 3.78 (m, 1H), 3.41 (s, 3H), 1.21 (d, 3H), 1.08 (m, 6H).

EXAMPLE 1.33

Production of (RS)-S-{4-[(5-bromo-4-{[(1R,2R)-2-hydroxy-1-(methoxymethyl)propyl]amino}pyrimidin-2-yl)amino]phenyl}-N-(ethoxycarbonyl)-S-ethyl sulfoximide

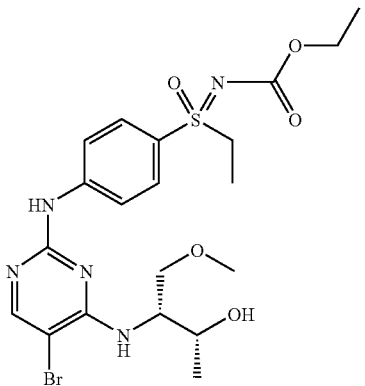

$^1$H-NMR (DMSO): 9.92 (s, 1H), 8.17 (s, 1H), 7.99 (m, 2H), 7.70 (m, 2H), 6.08 (d, 1H), 5.12 (m, 1H), 4.20 (m, 1H), 4.00 (m, 1H), 3.89 (m, 2H), 3.50 (m, 4H), 3.28 (s, 3H), 1.08 (m, 9H).

EXAMPLE 1.34

Production of (RS)-S-{4-[(5-bromo-4-{[(1R,2R)-2-hydroxy-1-(methoxymethyl)propyl]amino}pyrimidin-2-yl)amino]phenyl}-N-(ethoxycarbonyl)-S-methyl sulfoximide

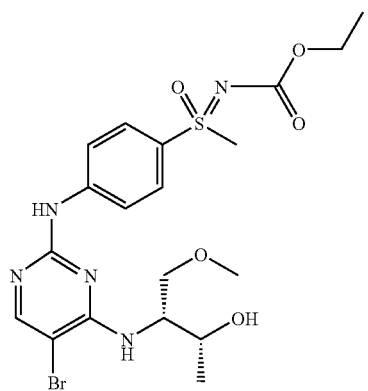

$^1$H-NMR (DMSO): 9.91 (s, 1H), 7.95 (s, 1H), 7.95 (m, 2H), 7.78 (m, 2H), 6.08 (d, 1H), 5.13 (m, 1H), 4.20 (m, 1H), 3.95 (m, 3H), 3.48 (m, 2H), 3.40 (s, 3H), 3.27 (s, 3H), 1.10 (m, 6H).

EXAMPLE 1.35

Production of (RS)-S-[4-({5-bromo-4-[(R)-(2-hydroxy-1,2-dimethylpropyl)amino]pyrimidin-2-yl}amino)phenyl]-N-(ethoxycarbonyl)-S-ethyl sulfoximide

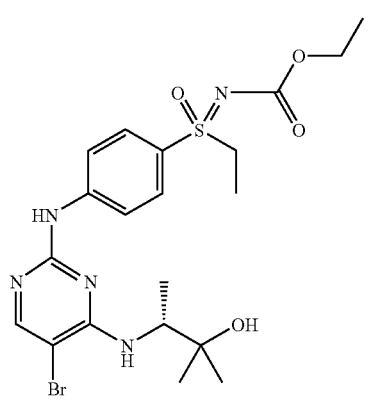

$^1$H-NMR (DMSO): 9.89 (s, 1H), 8.14 (s, 1H), 7.99 (m, 2H), 7.72 (m, 2H), 6.13 (d, 1H), 4.84 (s, 1H), 4.09 (m, 1H), 3.90 (m, 2H), 3.54 (q, 2H), 1.15 (m, 15H).

EXAMPLE 1.36

Production of (RS)-S-[4-({5-bromo-4-[(1R,2R)-(2-hydroxy-1-methylpropyl)amino]pyrimidin-2-yl}amino)phenyl]-N-(ethoxycarbonyl)-S-ethyl sulfoximide

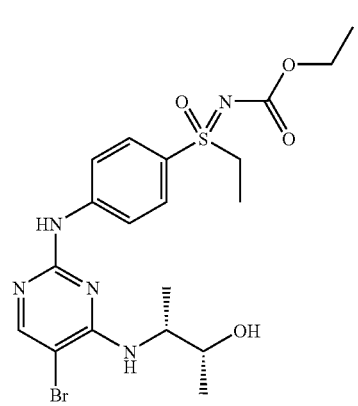

$^1$H-NMR (DMSO): 9.92 (s, 1H), 8.13 (s, 1H), 7.97 (m, 2H), 7.72 (m, 2H), 6.27 (d, 1H), 4.10 (m, 1H), 9.92 (m, 2H), 3.80 (m, 1H), 3.55 (q, 2H), 1.23 (d; 3H), 1.10 (m, 9H).

EXAMPLE 1.37

Production of (RS)-S-[4-({5-bromo-4-[(R)-(2-hydroxy-1,2-dimethylpropyl)amino]pyrimidin-2-yl}amino)-2-methylphenyl]-N-(ethoxycarbonyl)-S-methyl sulfoximide

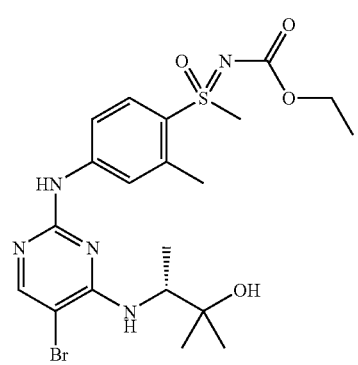

$^1$H-NMR (DMSO): 9.98 (s, 1H), 7.75 (m, 3H), 6.22 (d, 1H), 4.05 (m, 1H), 3.88 (q, 2H), 3.39 (s, 3H), 2.57 (s, 3H), 1.15 (m, 12H). MS: 514 (ES).

EXAMPLE 1.38

Production of (RS)-S-[4-({5-bromo-4-[(1R,2R)-(2-hydroxy-1-methylpropyl)amino]pyrimidin-2-yl}amino)-2-methylphenyl]-N-(ethoxycarbonyl)-S-methyl sulfoximide

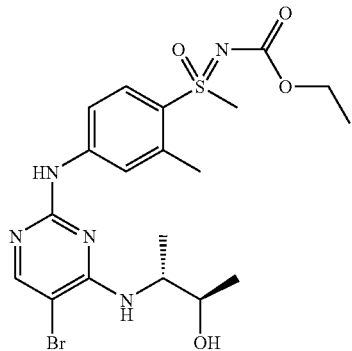

$^1$H-NMR (DMSO): 9.88 (s, 1H), 8.13 (s, 1H), 7.79 (m, 3H), 6.33 (d, 1H), 4.04 (m, 1H), 3.90 (q, 2H), 3.82 (m, 1H), 3.30 (s, 3H), 2.62 (s, 3H), 1.22 (d, 3H), 1.08 (m, 6H).

EXAMPLE 1.39

Production of (RS)-S-[4-({5-bromo-4-[(1R,2R)-2-hydroxy-1-methylpropoxy]pyrimidin-2-yl}amino)phenyl]-N-(ethoxycarbonyl)-S-ethyl sulfoximide

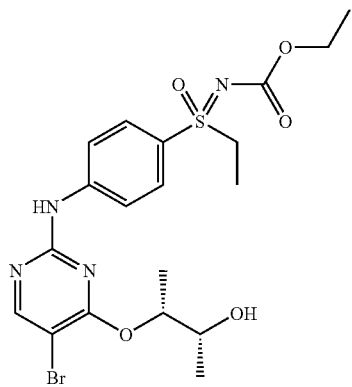

128 mg (0.51 mmol) of (RS)-S-(4-aminophenyl)-N-(ethoxycarbonyl)-S-ethyl sulfoximide and 150 mg (0.53 mmol) of (2R,3R)-3-[(5-bromo-2-chloropyrimidin-4-yl)oxy]-butan-2-ol in 2 ml of acetonitrile are mixed with 0.12 ml of a 4N solution of HCl in dioxane. The batch is stirred for 2 days at 60° C. The solvent is removed, and the residue is purified by chromatography (DCM/EtOH 95:5). 43 mg (0.09 mmol, corresponding to 17% of theory) of the product is obtained.

$^1$H-NMR (DMSO): 10.28 (s, 1H), 8.45 (s, 1H), 7.99 (m, 2H), 7.78 (m, 2H), 5.22 (m, 1H), 4.91 (d, 1H), 3.88 (m, 3H), 3.53 (q, 2H), 1.30 (d, 3H), 1.10 (m, 9 H).

EXAMPLE 1.40

Production of (RS)-S-[4-({5-bromo-4-[(1R,2R)-2-hydroxy-1-methylpropoxy]pyrimidin-2-yl}amino)phenyl]-N-(ethoxycarbonyl)-S-methyl sulfoximide

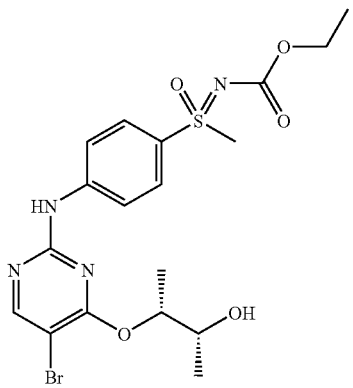

$^1$H-NMR (DMSO): 10.24 (s, 1H), 8.45 (s, 1H), 7.97 (m, 2H), 7.85 (m, 2H), 5.22 (m, 1H), 4.91 (d, 1H), 3.90 (m, 3H), 3.43 (s, 3H), 1.30 (d, 3H), 1.11 (m, 6 H).

Method D

EXAMPLES 1.41/1.42

Production and Separation into the Diastereomers of (RS)-S-[4-({5-bromo-4-[(R)-(2-hydroxy-1,2-dimethylpropyl)amino]pyrimidin-2-yl}amino)phenyl]-S-methyl sulfoximide (Example 1.3)

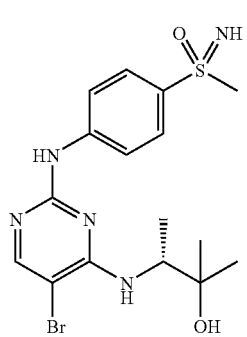

1.65 g (3.30 mmol) of (RS)-S-[4-({5-bromo-4-[(R)-(2-hydroxy-1,2-dimethylpropyl)amino]pyrimidin-2-yl}amino)phenyl]-N-(ethoxycarbonyl)-S-methyl sulfoximide in 6.5 ml of ethanol is mixed with 19.1 ml (6.69 mmol) of a 0.35 molar solution of NaOEt in ethanol and stirred under reflux for 5 hours. The batch is stirred overnight at room temperature and then added to a saturated NaCl solution. It is extracted with ethyl acetate, and the combined organic phases are dried (Na$_2$SO$_4$), filtered and concentrated by evaporation. The remaining residue is purified by chromatography (DCM/EtOH 9:1). 0.95 g (2.22 mmol, corresponding to 67% of theory) of the product is obtained.

The analytical data are similar to those of Example 1.3 from Process Variant 1, Method A.

The diastereomer mixture is cleaved into the diastereomers by means of preparatory HPLC:

| | |
|---|---|
| Column: | Chiralpak OJ 20μ |
| Length × ID: | 290 × 50.8 mm |
| Eluants: | A = Hexane + 0.1% DEA, B = ethanol |
| Flow: | 80 ml/min |
| Gradient: | Isocratic 15% B |
| Detector: | UV 300 nm |
| Temperature: | Room temperature |
| RT in min: | 29.4; Diastereomer 1 (Example 1.41) |
| | 37.1; Diastereomer 2 (Example 1.42) |

Similarly produced are:

EXAMPLES 1.43/1.44

Production and Separation into the Diastereomers of (RS)-S-[4-({5-bromo-4-[(1R,2R)-(2-hydroxy-1-methylpropyl)amino]pyrimidin-2-yl}amino)phenyl]-S-methyl sulfoximide (Example 1.2)

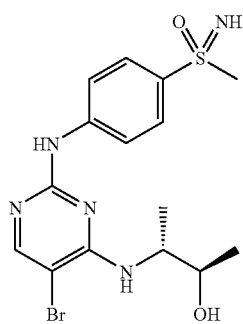

The analytical data are similar to those of Example 1.2 from Process Variant 1, Method A.

The diastereomer mixture is cleaved into the diastereomers by means of preparatory HPLC:

| | |
|---|---|
| Column: | Chiralpak OJ 20μ |
| Length × ID: | 290 × 50.8 mm |
| Eluants: | A = Hexane + 0.1% DEA, B = ethanol |
| Flow: | 80 ml/min |
| Gradient: | Isocratic 15% B |
| Detector: | UV 280 nm |
| Temperature: | Room temperature |
| RT in min: | 44.6; Diastereomer 1 (Example 1.43) |
| | 57.3; Diastereomer 2 (Example 1.44) |

EXAMPLE 1.45

Production of (RS)-S-{4-[(5-bromo-4-{[(1R,2R)-2-hydroxy-1-(methoxymethyl)-propyl]amino}pyrimidin-2-yl)amino]phenyl}-S-methyl sulfoximide

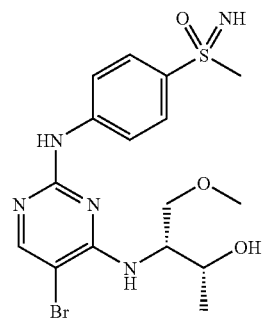

$^1$H-NMR (DMSO): 9.77 (s, 1H), 8.14 (s, 1H), 7.91 (m, 2H), 7.76 (m, 2H), 6.05 (d, 1H), 5.12 (br, 1H), 4.20 (m, 1H), 3.98 (m, 2H), 3.49 (m, 2H), 3.29 (s, 3 H), 3.02 (s, 3H), 1.19 (d, 3H).

The diastereomer mixture is cleaved into the diastereomers by means of preparatory HPLC:

| | |
|---|---|
| Column: | Chiralcel OJ 20μ |
| Length × ID: | 290 × 50.8 mm |
| Eluants: | Hexane/ethanol 80:20 |
| Flow: | 80.0 ml/min |
| Detector: | UV 300 nm |
| Temperature: | Room temperature |
| RT in min: | 47.55: Diastereomer 1 (Example 1.46) |
| | 61.02: Diastereomer 2 (Example 1.47) |

EXAMPLE 1.48

Production of (RS)-S-{4-[(5-bromo-4-{[(1R,2R)-2-hydroxy-1-(methoxymethyl)-propyl]amino}pyrimidin-2-yl)amino]phenyl}-S-ethyl sulfoximide

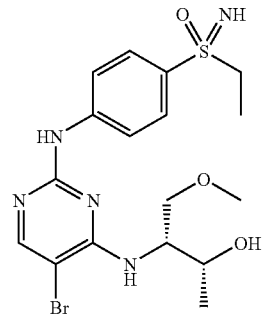

$^1$H-NMR (DMSO): 9.78 (s, 1H), 8.14 (s, 1H), 7.94 (m, 2H), 7.70 (m, 2H), 6.05 (d, 1H), 5.11 (d, 1H), 4.19 (m, 1H), 3.97 (m, 2H), 3.50 (m, 2H), 3.30 (s, 3H), 3.05 (q, 2H), 1.07 (m, 6H).

The diastereomer mixture is cleaved into the diastereomers by means of preparatory HPLC:

| Column: | Chiralcel OJ 20µ |
|---|---|
| Length × ID: | 290 × 50.8 mm |
| Eluants: | Hexane:ethanol 80:20 |
| Flow: | 80 ml/min |
| Detector: | UV 300 nm |
| Temperature: | Room temperature |
| RT in min: | 45.5: Diastereomer 1 (Example 1.49) |
| | 53.1: Diastereomer 2 (Example 1.50) |

EXAMPLE 1.51

Production of (RS)-S-[4-({5-bromo-4-[(1R,2R)-(2-hydroxy-1-methylpropyl)amino]pyrimidin-2-yl}amino)phenyl]-S-ethyl sulfoximide

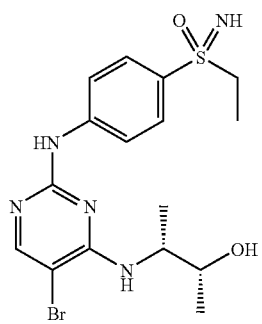

$^1$H-NMR (DMSO): 9.71 (s, 1H), 8.11 (s, 1H), 7.90 (m, 2H), 7.71 (m, 2H), 6.13 (d, 1H), 5.01 (d, 1H), 4.08 (m, 1H), 3.93 (s, 1H), 3.78 (m, 1H), 3.03 (q, 2H), 1.22 (d, 3H), 1.10 (m, 6H).

The diastereomer mixture is cleaved into the diastereomers by means of preparatory HPLC:

| Column: | Chiracel OJ 20µ |
|---|---|
| Length × ID: | 250 × 50.8 mm |
| Eluants: | A: Hexane + 0.1% DEA; B: Ethanol |
| Flow: | 80 ml/min |
| Gradient: | Isocratic 15% B |
| Detector: | UV 300 nm |
| Temperature: | Room temperature |
| RT in min: | 34.0: Diastereomer 1 (Example 1.52) |
| | 43.7: Diastereomer 2 (Example 1.53) |

EXAMPLE 1.54

Production of (RS)-S-[4-({5-bromo-4-[(R)-(2-hydroxy-1,2-dimethylpropyl)amino]pyrimidin-2-yl}amino)phenyl]-S-ethyl sulfoximide

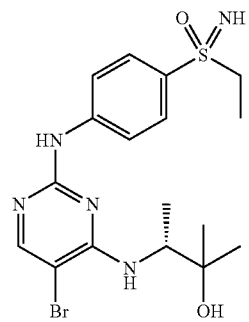

$^1$H-NMR (DMSO): 9.74 (s, 1H), 8.13 (s, 1H), 7.92 (m, 2H), 7.71 (m, 2H), 6.09 (d, 1H), 4.84 (s, 1H), 4.08 (m, 1H), 3.92 (s, 1H), 3.06 (q, 2H), 1.15 (m, 12H).

The diastereomer mixture is cleaved into the diastereomers by means of preparatory HPLC:

| Column: | Chiralpak AD 20µ |
|---|---|
| Length × ID: | 250 × 60 mm |
| Eluants: | Hexane/2-Propanol 80:20 |
| Flow: | 80/100 ml/min |
| Detector: | UV 280 nm |
| Temperature: | Room temperature |
| RT in min: | 222.2: Diastereomer 1 (Example 1.55) |
| | 249.8: Diastereomer 2 (Example 1.56) |

EXAMPLE 1.57

Production of (RS)-S-[4-({5-bromo-4-[(R)-(2-hydroxy-1,2-dimethylpropyl)amino]pyrimidin-2-yl}amino)-2-methylphenyl]-S-methyl sulfoximide

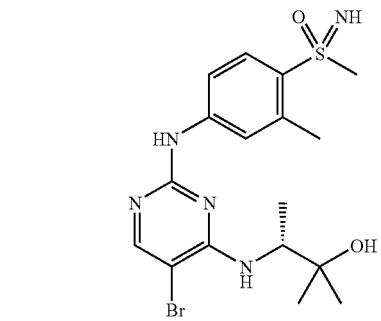

$^1$H-NMR (DMSO): 9.63 (s, 1H), 8.11 (s, 1H), 7.81 (m, 2H), 7.63 (m, 1H), 6.08 (d, 1H), 4.88 (s, 1H), 4.06 (m, 2H), 3.03 (s, 3H), 2.67 (s, 3H), 1.2 (m, 9H). MS: 442 (ES).

The diastereomer mixture is cleaved into the diastereomers by means of preparatory HPLC:

| | |
|---|---|
| Column: | Chiralpak AS 20μ |
| Length × ID: | 250 × 50.8 mm |
| Eluants: | A = Hexane, B = Ethanol |
| Flow: | 80 ml/min |
| Gradient: | Isocratic 15% B |
| Detector: | UV 300 nm |
| Temperature: | Room temperature |
| RT in min: | 18.96; Diastereomer 1 (Example 1.58) |
| | 21.56; Diastereomer 2 (Example 1.59) |

EXAMPLE 1.60

Production of (RS)-S-[4-({5-bromo-4-[(1R,2R)-(2-hydroxy-1-methylpropyl)amino]pyrimidin-2-yl}amino)-2-methylphenyl]-S-methyl sulfoximide

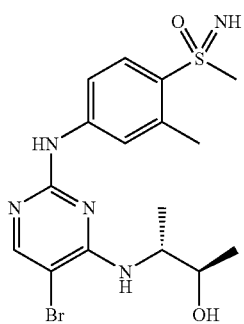

$^1$H-NMR (DMSO): 9.62 (s, 1H), 8.11 (s, 1H), 7.82 (m, 2H), 7.66 (m, 1H), 6.14 (d, 1H), 5.02 (d, 1H), 4.04 (m, 2H), 3.80 (m, 1H), 3.03 (s, 3H), 2.65 (s, 3H), 1.22 (d, 3H), 1.10 (d, 3H).

The diastereomer mixture is cleaved into the diastereomers by means of preparative HPLC:

| | |
|---|---|
| Column: | Chiralpak AD 20μ |
| Length × ID: | 250 × 50.8 mm |
| Eluants: | A: Hexane + 0.1% DEA, B: Ethanol |
| Flow: | 80 ml/min |
| Gradient: | Isocratic 25% B |
| Detector: | UV 280 nm |
| Temperature: | Room temperature |
| RT in min: | 104, Diastereomer 1 (Example 1.61) |
| | 124, Diastereomer 2 (Example 1.62) |

EXAMPLE 1.63

Production of (RS)-S-{4-[(5-bromo-4-ethoxypyrimidin-2-yl)amino]phenyl}-S-ethyl sulfoximide

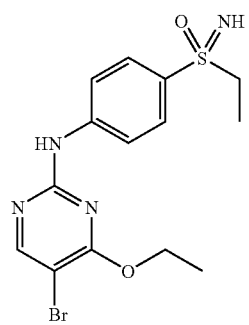

28 mg (0.056 mmol) of (RS)-S-[4-({5-bromo-4-[(1R,2R)-2-hydroxy-1-methylpropoxy]pyrimidin-2-yl}amino)phenyl]-N-(ethoxycarbonyl)-S-methyl sulfoximide in 0.11 ml of ethanol is mixed with 0.32 ml (0.113 mmol) of a 0.35 molar solution of NaOEt in ethanol and stirred under reflux for 6 hours. The batch is stirred overnight at room temperature, and then added to a saturated NaCl solution. It is extracted with ethyl acetate, and the combined organic phases are dried (Na$_2$SO$_4$), filtered and concentrated by evaporation. The remaining residue is purified by chromatography (DCM/EtOH 85:15). 9 mg (0.023 mmol, corresponding to 42% of theory) of the product is obtained.

$^1$H-NMR (DMSO): 10.17 (s, 1H), 8.45 (s, 1H), 7.94 (m, 2H), 7.78 (m, 2H), 4.49 (q, 2H), 3.98 (s, 1H), 3.07 (q, 2H), 1.40 (tr, 3H), 1.04 (tr, 3H). MS: 385 (ES).

EXAMPLE 1.64

Production of (RS)-N-(ethoxycarbonyl)-S-(4-{[5-iodo-4-(prop-2-in-1-ylamino)pyrimidin-2-yl]amino}phenyl)-S-methyl sulfoximide

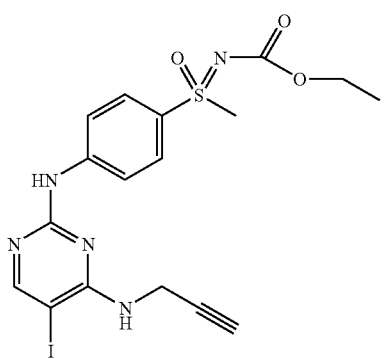

400 mg (1.65 mmol) of (2-chloro-5-iodopyrimidin-4-yl)-prop-2-in-1-yl-amine and 630 mg (2.15 mmol) of (RS)-S-(4-aminophenyl)-N-(ethoxycarbonyl)-S-methyl sulfoximide in 7 ml of acetonitrile are mixed with 0.6 ml of a 4N solution of HCl in dioxane and 1 ml of water. The batch is stirred for 24 hours at 50° C. The solvent is drawn off, and the remaining residue is purified by chromatography (DCM/

EtOH 9:1). 279 mg (0.56 mmol, corresponding to 54% of theory) of the product is obtained.

¹H-NMR (DMSO): 10.19 (s, 1H), 8.30 (s, 11H), 8.05 (m, 2H), 7.81 (m, 2H), 7.59 (br, 1H), 4.17 (d, 2H), 3.88 (q, 2H), 3.43 (s, 3H), 3.18 (br, 1H), 1.10 (tr, 3H). MS: 500 (ES).

EXAMPLE 1.65

Production of (RS)-N-(ethoxycarbonyl)-S-{4-[(4-{(R)-[1-(hydroxymethyl)-2-methylpropyl]amino}-5-iodopyrimidin-2-yl)amino]phenyl}-S-methyl sulfoximide

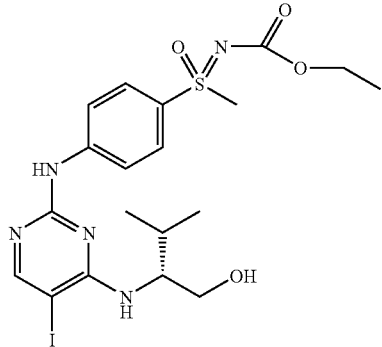

¹H-NMR (DMSO): 9.81 (s, 1H), 8.22 (s, 1H), 7.98 (m, 2H), 7.78 (m, 2H), 5.89 (d, 1H), 4.85 (tr, 1H), 4.04 (m, 1H), 3.92 (q, 2H), 3.65 (m, 1H), 3.56 (m, 1 H), 3.41 (s, 3H), 2.02 (m, 1H), 1.10 (tr, 3H), 0.95 (dd, 6H). MS: 548 (ES)

EXAMPLE 1.66

Production of (RS)-S-{4-[(4-{(R)-[1-(hydroxymethyl)-2-methylpropyl]amino}-5-iodopyrimidin-2-yl)amino]phenyl}-S-methyl sulfoximide

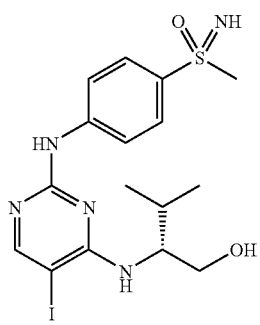

¹H-NMR (DMSO): 9.68 (s, 1H), 8.21 (s, 1H), 7.92 (m, 2H), 7.75 (m, 2H), 5.87 (d, 1H), 4.86 (tr, 1H), 4.01 (m, 2H), 3.66 (m, 1H), 3.55 (m, 1H), 3.01 (s, 3 H), 2.02 (m, 1H), 0.94 (m, 6H).

EXAMPLE 1.67

Production of (RS)-S-[4-({5-bromo-4-[(1R,2R)-(2-hydroxy-1-methylpropyl)amino]pyrimidin-2-yl}amino)-2-fluorophenyl]-N-(ethoxycarbonyl)-S-methyl sulfoximide

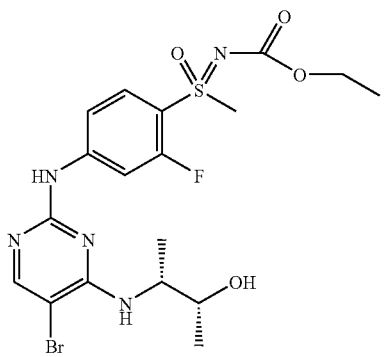

¹H-NMR (DMSO): 10.08 (s, 1H), 8.18 (s, 1H), 8.02 (m, 1H), 7.68 (m, 2H), 6.27 (d, 1H), 5.03 (br, 1H), 4.08 (m, 1H), 3.88 (m, 2H), 3.79 (m, 1H), 3.48 (s, 3H), 1.21 (d, 3H), 1.09 (m, 6H). MS: 504 (ES).

EXAMPLE 1.68

Production of (RS)-S-[4-({5-bromo-4-[(R)-(2-hydroxy-1,2-dimethylpropyl)amino]pyrimidin-2-yl}amino)-2-fluorophenyl]-N-(ethoxycarbonyl)-S-methyl sulfoximide

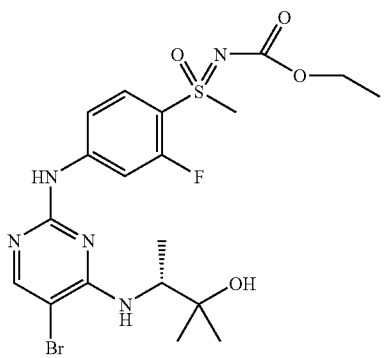

¹H-NMR (DMSO): 10.12 (s, 1H), 8.17 (s, 1H), 8.02 (m, 1H), 7.73 (m, 1H), 7.63 (m, 1H), 6.26 (d, 1H), 4.08 (m, 1H), 3.85 (m, 2H), 3.42 (s, 3H), 1.11 (m, 12H). MS: 518 (ES).

EXAMPLE 1.69

Production of (RS)-S-[4-({5-bromo-4-[(R)-(2-hydroxy-1,2-dimethylpropyl)amino]pyrimidin-2-yl}amino)-2-trifluoromethylphenyl]-N-(ethoxycarbonyl)-S-methyl sulfoximide

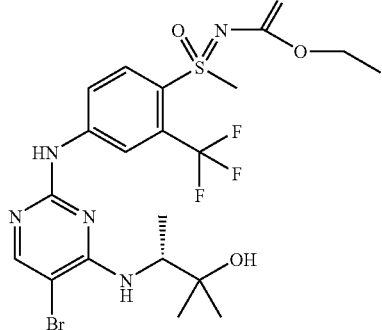

¹H-NMR (DMSO): 10.21 (s, 1H), 8.65 (s, 1H), 8.19 (s, 1H), 8.05 (s, 2H), 6.18 (d, 1H), 4.90 (br, 1H), 4.05 (m, 1H), 3.89 (q, 2H), 3.40 (s, 3H), 1.12 (m, 12 H). MS: 568 (ES).

Process Variant 2

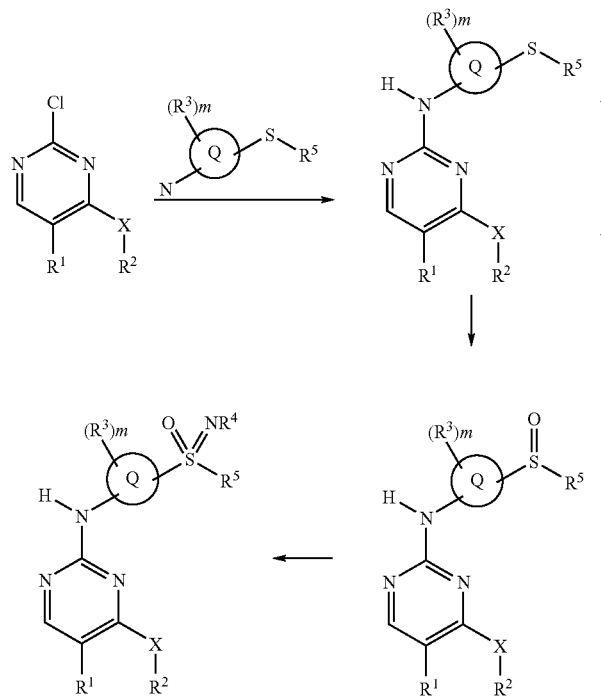

Substituents $R^1$, $R^2$, $R^3$, $R^4$, $R^5$, Q, and m have the meaning that is indicated in general formula (I).

Method A

EXAMPLE 2.0

Production of (RS)-S-(4-{[5-bromo-4-(isopropylamino)pyrimidin-2-yl]amino}phenyl)-S-methyl sulfoximide

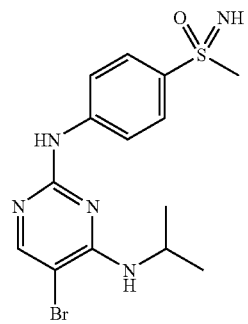

185 mg (0.50 mmol) of (RS)-5-bromo-N-4-isopropyl-$N^2$-[4-(methyl sulfinyl)phenyl]-pyrimidine-2,4-diamine in 1 ml of DCM is mixed with 40 mg (0.55 mmol) of sodium azide. The batch is slowly mixed with 0.13 ml of concentrated sulfuric acid at 0° C. and then heated to 45° C. After 16 hours, the batch is cooled to room temperature, mixed with 2 ml of 1N NaOH solution and extracted from ethyl acetate. The combined organic phases are dried ($Na_2SO_4$), filtered and concentrated by evaporation. The remaining residue is purified by chromatography (DCM/EtOH 9:1). 38 mg (0.10 mmol, corresponding to 20% of theory) of the product is obtained.

¹H-NMR (DMSO): 9.70 (s, 1H), 8.08 (s, 1H), 7.90 (d, 2H), 7.77 (d, 2H), 6.62 (d, 1H), 4.35 (m, 1H), 3.99 (s, 1H), 3.03 (s, 3H), 1.29 (d, 6H). MS: 384 (ES).

Method B

EXAMPLE 2.1

Production of (RS)-S-[4-({5-bromo-4-[(R)-(2-hydroxy-1-methylethyl)amino]pyrimidin-2-yl}amino)phenyl]-S-methyl-N-[2-(trimethylsilyl)ethylsulfonyl] sulfoximide

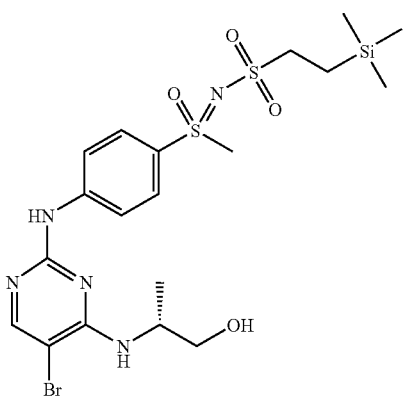

50 mg (0.13 mmol) of (R)-2-[5-bromo-2-{(RS)-4-methylsulfinyl-phenylamino}-pyrimidin-4-ylamino]-propan-1-ol in 3 ml of acetonitrile is mixed with a spatula tip full of $CuPF_6[CH_3CN]_4$ (about 0.05 equivalent) and stirred for 30 minutes at room temperature. The mixture is cooled in an ice bath, mixed with 55 mg (0.13 mmol) of [N-(2-(trimethylsilyl)ethanesulfonyl)imino]phenyliodinane, and stirred for 4 hours at room temperature. It is cooled again in the ice bath, mixed with a spatula tip full of CuPF₆[CH₃CN]₄ and with 22 mg (0.06 mmol) of [N-(2-(trimethylsilyl)ethanesulfonyl) imino]phenyliodinane and stirred for another 3 hours at room temperature. The mixture is evaporated to the dry state, and the remaining residue is purified by chromatography. 20 mg of (RS)-S-[4-({5-bromo-4-[(R)-(2-hydroxy-1-methylethyl)amino]pyrimidin-2-yl}amino)phenyl]-S-methyl-N-[2-(trimethylsilyl)ethylsulfonyl]sulfoximide with a melting point of 194-197° C. is obtained.

¹H-NMR (DMSO): 9.92 (s, 1H), 8.14 (s, 1H), 8.02 (d, 2H), 7.87 (d, 2H), 6.48 (d, 1H), 4.90 (t, 1H), 4.27 (m, 1H), 3.53 (s, 3H), 3.52 (m, 2H), 2.95 (m, 2H), 1.22 (d, 3H), 0.95 (m, 2H), 0.01 (s, 9H). MS: 564/566 (100%, ES).

EXAMPLE 1.0

Production of (RS)-S-[4-({5-bromo-4-[(R)-(2-hydroxy-1-methylethyl)amino]pyrimidin-2-yl}amino) phenyl]-S-methyl sulfoximide

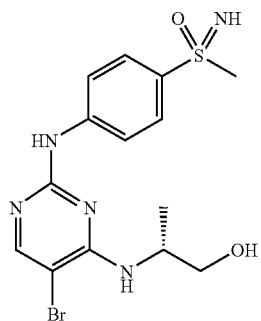

After the Ses-protective group is cleaved with tetrabutylammonium fluoride analogously to Example 1.6 (as described in *Tetrahedron Lett.* 2002, 43, 2751), 10 mg (0.02 mmol, corresponding to 70% of theory) of the product is obtained.

Produced in a way that is similar to the above-mentioned methods A and B of Process Variant 2 are the following compounds:

EXAMPLE 2.2

Production of (RS)-S-(4-{1[5-bromo-4-(phenylamino)pyrimidin-2-yl]amino}phenyl)-S-methyl-N-[2-(trimethylsilyl)ethylsulfonyl]sulfoximide

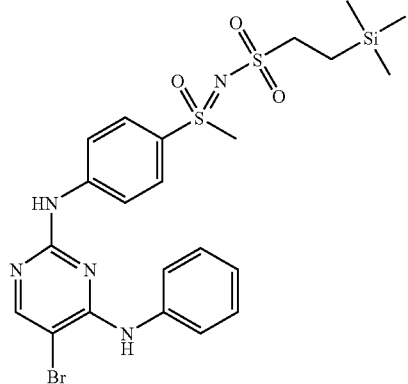

¹H-NMR (DMSO): 9.98 (s, 1H), 8.83 (s, 1H), 8.32 (s, 1H), 7.88 (d, 2H), 7.71 (d, 2H), 7.59 (d, 2H), 7.44 (t, 2H), 7.23 (t, 1H), 3.53 (s, 3H), 2.86-3.03 (m, 2H), 0.82-1.01 (m, 2H), 0.00 (s, 9H). MS: 582/584 (100%, ES).

EXAMPLE 2.3

Production of (RS)-S-(4-{[5-bromo-4-(phenylamino)pyrimidin-2-yl]amino}phenyl)-S-methyl sulfoximide

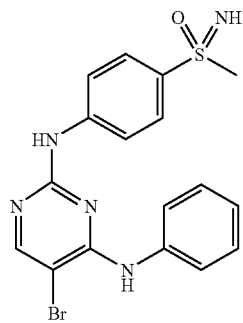

¹H-NMR (DMSO): 9.82 (s, 1H), 8.79 (s, 1H), 8.30 (s, 1H), 7.78 (d, 2H), 7.65 (d, 2H), 7.60 (d, 2H), 7.42 (t, 2H), 7.23 (t, 1H), 3.96 (s, 1H), 3.00 (s, 3H). MS: 418/420 (20%, ES).

EXAMPLE 2.4

Production of (RS)-S-[4-({4-[(2-fluoro-5-methylphenyl)amino]-pyrimidin-2-yl}amino)phenyl]-S-methyl-N-[2-(trimethylsilyl)ethylsulfonyl]-sulfoximide

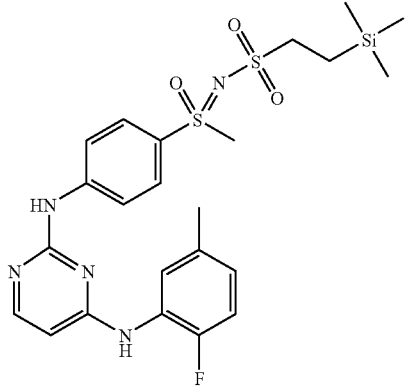

¹H-NMR (DMSO): 9.85 (s, 1H), 9.22 (s, 1H), 7.98 (d, 2H), 7.88 (d, 1H), 7.76 (d, 2H), 7.63 (d, 1H), 7.21 (m, 1H), 7.02 (m, 1H), 6.40 (m, 1H), 3.53 (s, 3H), 2.81-2.90 (m, 2H), 0.87-1.00 (m, 2H), 0.00 (s, 9H). MS: 536 (100%, ES).

EXAMPLE 2.5

Production of (RS)-S-[4-({4-[(2-fluoro-5-methylphenyl)amino]-pyrimidin-2-yl}amino)phenyl]-S-methyl sulfoximide

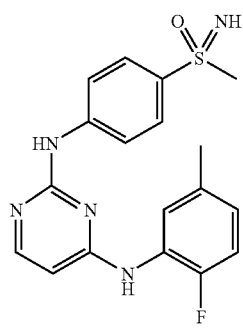

¹H-NMR (DMSO): 9.65 (s, 1H), 9.18 (s, 1H), 8.09 (d, 1H), 7.87 (d, 2H), 7.69 (d, 2H), 7.65 (d, 1H), 7.19 (m, 1H), 7.02 (m, 1H), 6.37 (m, 1H), 3.02 (s, 3H). MS: 372 (10%, ES).

Process Variant 3

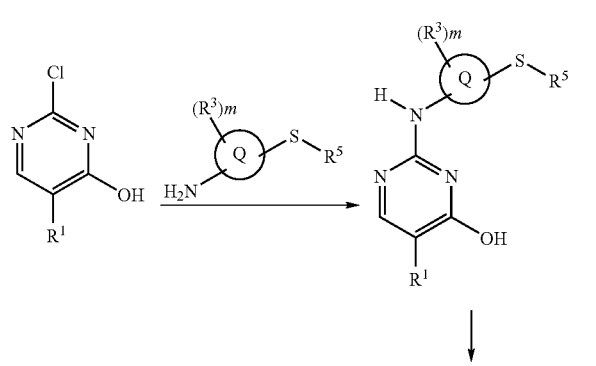

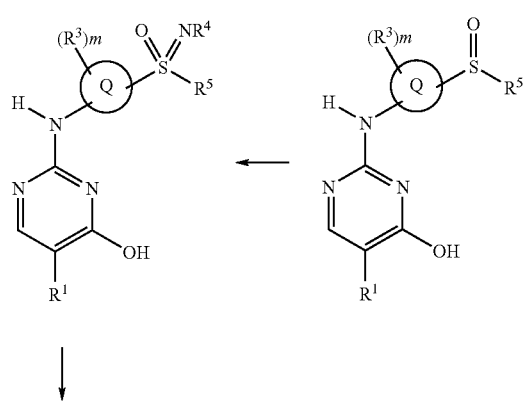

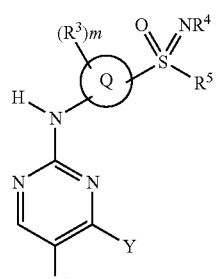

The substituents $R^1$, $R^2$, $R^3$, $R^4$, $R^5$, Q, and m have the meaning that is indicated in general formula (I). Y has the meaning of halogen.

EXAMPLE 3.0

Production of (RS)-S-[4-({5-bromo-4-[(RS)-(1-hydroxymethyl-propyl)sulfanyl]pyrimidin-2-yl}amino)phenyl]-S-methyl sulfoximide

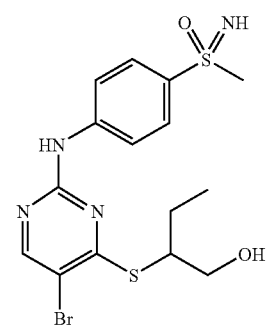

362 mg of (RS)-S-{4-[(5-bromo-4-chloropyrimidin-2-yl)amino]phenyl}-S-methyl sulfoximide is dissolved in 1.5 ml of dimethylformamide, mixed with 0.5 ml of triethylamine and 320 mg of (RS)-2-mercapto-butan-1-ol and stirred for 18 hours at room temperature. The mixture is evaporated to the dry state in a vacuum and purified by flash chromatography (dichloromethane/ethanol). 255 mg of the product with a melting point of 175-180° C. is obtained.

¹H-NMR (DMSO): 10.18 (s, 1H), 8.39 (s, 1H), 7.91 (d, 2H), 7.83 (d, 2H), 5.13 (t, 1H), 4.05 (s, 1H), 4.00 (m, 1H), 3.74 (m, 1H), 3.63 (m, 1H), 3.03 (s, 3H), 1.93 (m, 1H), 1.69 (m, 1H), 1.00 (t, 3H). MS: 431/433 (95/100%, ES).

Produced in a similar way are the following examples:

EXAMPLE 3.1

Production of (RS)-S-[4-({5-bromo-4-[(RS)-(1-methyl-propyl)sulfanyl]pyrimidin-2-yl}amino)phenyl]-S-methyl sulfoximide

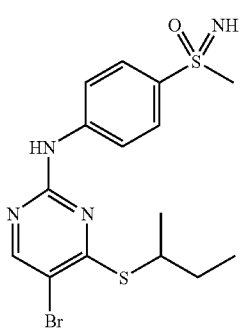

Melting point: 175-183° C.
¹H-NMR (DMSO): 10.19 (s, 1H), 8.40 (s, 1H), 7.95 (d, 2H), 7.85 (d, 2H), 4.04 (s, 1H), 3.97 (m, 1H), 3.03 (s, 3H), 1.76 (m, 2H), 1.42 (d, 2H), 1.01 (t, 3H). MS: 415/417 (90/100%, ES).

EXAMPLE 3.2

Production of (RS)-S-[4-({5-bromo-4-[(RS)-(1-methyl-2-oxo-propyl)sulfanyl]pyrimidin-2-yl}amino)phenyl]-S-methyl sulfoximide

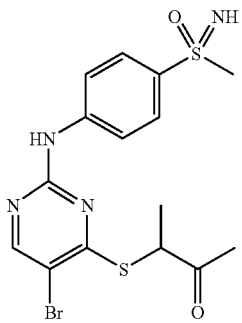

¹H-NMR (DMSO): 10.18 (s, 1H), 8.44 (s, 1H), 7.87 (s, 4H), 4.82 (q, 1H), 3.06 (s, 3H), 2.26 (s, 3H), 1.52 (d, 3H). MS: 429/431 (90/100%, ES).

EXAMPLE 3.3

Production of (RS)-S-[4-({4-[(RS)-(1-acetylpropyl)sulfanyl]-5-bromopyrimidin-2-yl}amino)phenyl]-S-methyl sulfoximide

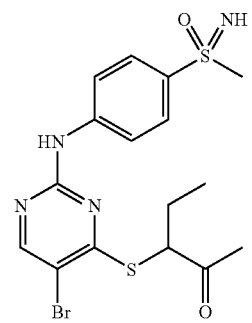

¹H-NMR (DMSO): 10.16 (s, 1H), 8.44 (s, 1H), 7.86 (s, 4H), 4.79 (t, 1H), 3.04 (s, 3H), 2.25 (s, 3H), 2.04 (m, 1H), 1.89 (m, 1H), 1.18 (t, 1.5H), 0.96 (t, 1.5 H). MS: 443/445 (90/100%, ES).

EXAMPLE 3.4

Production of (RS)-S-[4-({5-bromo-4-[(RS)-(2-hydroxy-propyl)sulfanyl]pyrimidin-2-yl}amino)phenyl]-S-methyl sulfoximide

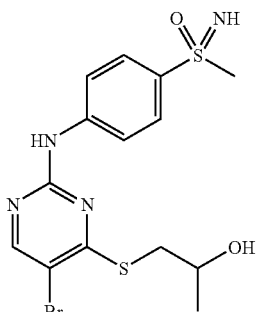

¹H-NMR (DMSO): 10.17 (s, 1H), 8.39 (s, 1H), 7.90 (d, 2H), 7.84 (d, 2H), 5.04 (d, 1H), 4.04 (s, 1H), 3.93 (m, 1H), 3.26 (d, 1H), 3.03 (s, 3H), 1.21 (d, 3H). MS: 417/419 (90/100%, ES).

EXAMPLE 3.5

Production of (RS)-S-[4-({5-bromo-4-[(RS,RS)-(2-hydroxy-1-methylpropyl)sulfanyl]pyrimidin-2-yl}amino)phenyl]-S-methyl sulfoximide

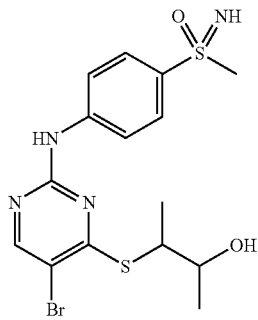

$^1$H-NMR (DMSO): 10.17 (s, 1H), 8.38 (s, 1H), 7.93-7.81 (m, 4H), 5.13+5.06 (d, 1H), 4.06 (m, 1H), 4.04 (s, 1H), 3.95 (m, 1H), 3.03 (s, 3H), 1.42+1.36 (d, 3H), 1.18 (m, 3H). MS: 431/433 (94/100%, ES).

EXAMPLE 3.6

Production of (RS)-S-[4-({5-bromo-4-[(RS,RS)-(1-ethyl-2-hydroxypropyl)sulfanyl]pyrimidin-2-yl}amino)phenyl]-S-methyl sulfoximide

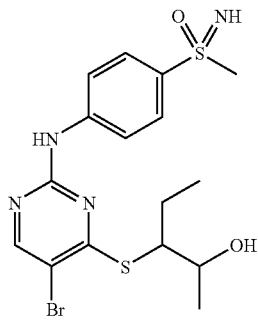

is obtained by reaction of (RS)-S-[4-({4-[(RS)-(1-acetylpropyl)sulfanyl]-5-bromopyrimidin-2-yl}amino)phenyl]-S-methyl sulfoximide with 1 equivalent of sodium borohydride in tetrahydrofuran/methanol (1:1).

Melting point: 192-194° C. $^1$H-NMR (DMSO): 10.14 (s, 1H), 8.38 (s, 1H), 7.90 (d, 2H), 7.83 (d, 2H), 5.06+4.98 (d, 1H), 4.08 (s, 1H), 4.00 (m, 2H), 3.03 (s, 3H), 1.93 (m, 1H), 1.66 (m, 1H), 1.16 (d, 3H), 0.99 (t, 3H). MS: 445/447 (96/100%, ES).

EXAMPLE 3.7

Production of (RS)-S-[4-({5-bromo-4-[(RS)-(2-hydroxy-1,2-dimethylpropyl)sulfanyl]pyrimidin-2-yl}amino)phenyl]-S-methyl sulfoximide

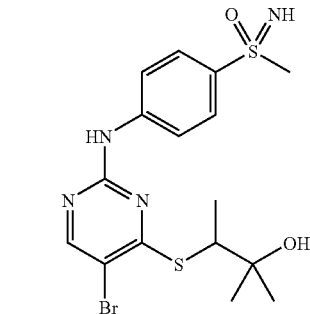

is obtained by reaction of (RS)-S-[4-({5-bromo-4-[(RS)-(1-methyl-2-oxo-propyl)sulfanyl]pyrimidin-2-yl}amino)phenyl]-S-methyl sulfoximide with 6 equivalents of methylmagnesium bromide in tetrahydrofuran.

Melting point: 201-202° C. $^1$H-NMR (DMSO): 10.18 (s, 1H), 8.38 (s, 1H), 7.92 (d, 2H), 7.83 (d, 2H), 4.89 (s, 1H), 4.09 (m, 1H), 4.05 (s, 1H), 3.03 (s, 3H), 1.43 (d, 3H), 1.27 (s, 6H). MS: 445/447 (93/100%, ES).

EXAMPLE 3.8

Production of (RS)-S-[4-({5-bromo-4-[(RS)-(1-ethyl-2-hydroxy-2-methylpropyl)sulfanyl]pyrimidin-2-yl}amino)phenyl]-S-methyl sulfoximide

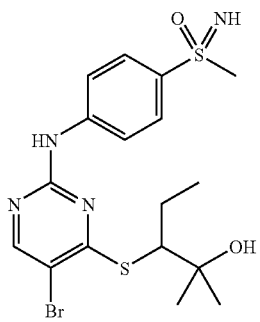

is obtained by reaction of (RS)-S-[4-({4-[(RS)$_7$(1-acetylpropyl)sulfanyl]-5-bromopyrimidin-2-yl}amino)phenyl]-S-methyl sulfoximide with 6 equivalents of methylmagnesium bromide in tetrahydrofuran.

Melting point: 218° C. (decomposition) $^1$H-NMR (DMSO): 10.17 (s, 1H), 8.38 (s, 1H), 7.92 (d, 2H), 7.83 (d, 2H), 4.78 (s, 1H), 4.12 (dd, 1H), 4.05 (s, 1H), 3.03 (s, 3H), 2.10 (m, 1H), 1.48 (m, 1 H), 1.24 (s, 6H), 0.95 (dd, 3H). MS: 459/461 (93/100%, ES).

EXAMPLE 3.9

Production of (RS)-S-[4-({5-bromo-4-[(2-hydroxy-2-methyl-propyl)sulfanyl]pyrimidin-2-yl}amino)phenyl]-S-methyl sulfoximide

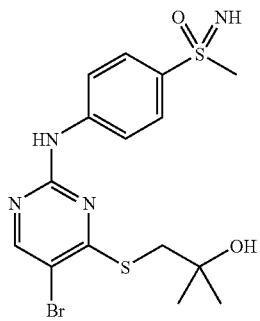

is obtained by reaction of (RS)-S-[4-({5-bromo-4-[(4-methoxycarbonylmethyl)sulfanyl]pyrimidin-2-yl}amino)phenyl]-S-methyl sulfoximide with 6 equivalents of methylmagnesium bromide in tetrahydrofuran.

$^1$H-NMR (DMSO): 10.17 (s, 1H), 8.39 (s, 1H), 7.92 (d, 2H), 7.83 (d, 2H), 4.84 (s, 1H), 4.05 (s, 1H), 3.41 (s, 2H), 3.03 (s, 3H), 1.26 (s, 6H). MS: 431/433 (94/100%, ES).

EXAMPLE 3.10

Production of (RS)-S-[4-({5-bromo-4-[(RS)-(2-hydroxy-1-methyl-ethyl)sulfanyl]pyrimidin-2-yl}amino)phenyl]-S-methyl sulfoximide

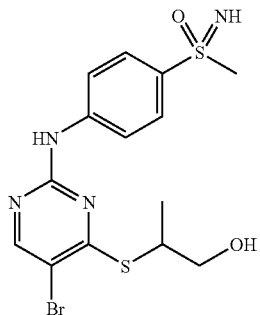

Melting point: 218-220° C. $^1$H-NMR (DMSO): 10.19 (s, 1H), 8.40 (s, 1H), 7.92 (d, 2H), 7.84 (d, 2H), 5.18 (t, 1H), 4.07 (m, 2H), 3.69 (m, 1H), 3.61 (m, 1H), 3.04 (s, 3H), 1.42 (d, 3H). MS: 417/419 (92/100%, ES).

EXAMPLE 3.11

Production of (RS)-S-[4-({5-bromo-4-[(4-methoxycarbonylmethyl)sulfanyl]pyrimidin-2-yl}amino)phenyl]-S-methyl sulfoximide

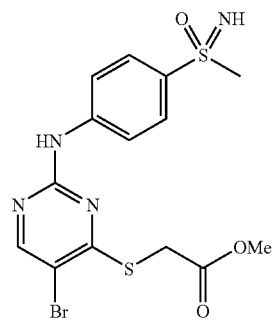

$^1$H-NMR (DMSO): 10.22 (s, 1H), 8.44 (s, 1H), 7.82 (s, 4H), 4.22 (s, 2H), 4.16 (s (br), 1H), 3.58 (s, 3H), 3.05 (s, 3H). MS: 431/433 (91/100%, ES).

EXAMPLES 3.12/3.13

Production and Separation into the Diastereomers of (RS)-S-[4-({5-bromo-4-[(1R,2R)-2-hydroxy-1-methylpropoxy]pyrimidin-2-yl}amino)phenyl]-S-methyl sulfoximide (Example 1.4)

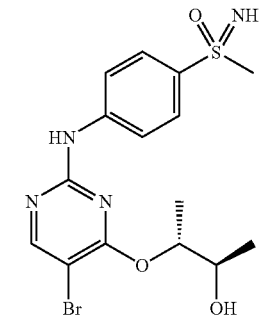

A solution of 674 mg (7.5 mmol) of (R,R)-(−)-2,3-butanediol in 6 ml of DMSO is mixed while being cooled with water in portions with 330 mg of sodium hydride (55-60%), and then stirred for 45 minutes at room temperature. The batch is mixed with 196 mg (0.54 mmol) of (RS)-S-{4-[(5-bromo-4-chloropyrimidin-2-yl)amino]phenyl}-S-methyl sulfoximide in 0.5 ml of DMSO and stirred overnight. It is mixed again with 191 mg (0.53 mmol) of (RS)-S-{4-[(5-bromo-4-chloropyrimidin-2-yl)amino]phenyl}-S-methyl sulfoximide in 0.5 ml of DMSO and stirred for another two hours. Finally, it is mixed with 190 mg of (RS)-S-{4-[(5-bromo-4-chloropyrimidin-2-yl)amino]phenyl}-S-methyl sulfoximide (0.53 mmol) in 0.5 ml of DMSO and stirred for one hour. The batch is added to ice water and extracted from ethyl acetate (4×). The combined organic phases are washed with NaCl solution, filtered through a Whatman filter and concentrated by evaporation. The remaining residue is purified by chromatography (DCM/EtOH 9:1). 166 mg (0.41 mmol, corresponding to 25% of theory) of the product is obtained.

The analytical data are consistent with those from the preparation according to Process Variant 1.

The diastereomer mixture is cleaved into the diastereomers by means of preparatory HPLC:

| | |
|---|---|
| Column: | Chiracel OJ 20μ |
| Length × ID: | 290 × 50.8 mm |
| Eluants: | A: Hexane, B: Ethanol |
| Flow: | 80 ml/mm |
| Gradient: | Isocratic 15% B |
| Detector: | UV 300 nm |
| Temperature: | Room temperature |
| RT in min: | 32.8: Diastereomer 1 (Example 3.12) |
| | 39.2: Diastereomer 2 (Example 3.13) |

Production of the Intermediate Products a) Production of (RS)-S-(4-aminophenyl)-S-methyl sulfoximide

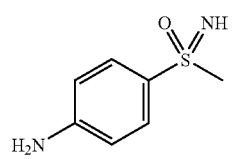

A solution of 2.45 g (12.2 mmol) of (RS)-S-(4-nitrophenyl)-S-methyl sulfoximide in 150 ml of ethanol is hydrogenated at room temperature with use of 0.80 g of Pd/C (10%×50% $H_2O$) under a hydrogen atmosphere at normal pressure over 4 hours. The hydrogen absorption is 920 ml. The batch is filtered and concentrated by evaporation. The residue that is obtained is digested with diisopropyl ether. 1.90 g (11.2 mmol, corresponding to 92% of theory) is obtained.

$^1$H-NMR (DMSO): 7.53 (d, 2H), 6.64 (d, 2H), 5.91 (s, 2H), 3.68 (s, 1H), 2.93 (s, 3H). ES: 171 (ES).

b) Production of (RS)-S-(4-nitrophenyl)-S-methyl sulfoximide

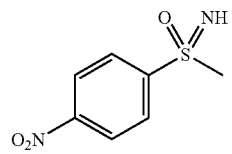

1.56 g (8.5 mmol) of 1-(methylsulfinyl)-4-nitrobenzene in 20 ml of DCM is mixed with 0.70 g (9.5 mmol) of sodium azide. The batch is slowly mixed at 0° C. with 2.3 ml of concentrated sulfuric acid and then heated to 45° C. After 16 hours, the batch is cooled to room temperature, mixed with water and extracted from DCM. The aqueous phase is set at pH 11 with 15% NaOH solution and extracted from DCM. The combined organic phases are dried ($Na_2SO_4$), filtered and concentrated by evaporation. 1.08 g (5.4 mmol, corresponding to 63% of theory) of the product is obtained.

$^1$H-NMR (DMSO): 8.43 (d, 2H), 8.17 (d, 2H), 4.62 (s, 1H), 3.18 (s, 3H). ES: 201 (ES).

c) Production of 1-(Methylsulfinyl)-4-nitrobenzene

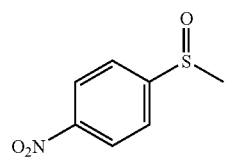

A solution of 16.0 g (95 mmol) of 1-methylsulfanyl-4-nitro-benzene in 400 ml of DCM is mixed at room temperature with 24.6 g (100 mmol) of 3-chloroperoxybenzoic acid (about 70%). After 1 hour, the batch is diluted with DCM and washed with saturated $NaHCO_3$ solution. The organic phase is dried ($Na_2SO_4$), filtered and concentrated by evaporation. The remaining residue is purified by chromatography (DCM/EtOH 8:2). 7.6 g (41 mmol, corresponding to 43% of theory) of the product is obtained.

H-NMR (DMSO): 8.41 (d, 2H), 7.97 (d, 2H), 2.86 (s, 3H). ES: 186 (ES).

d) Production of (RS)-S-(3-aminophenyl)-S-methyl sulfoximide

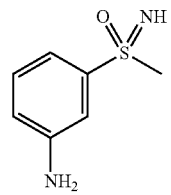

A solution of 200 mg (1.00 mmol) of (RS)-S-methyl-S-(3-nitrophenyl)sulfoximide in 20 ml of THF is mixed at room temperature with 8 ml of an approximately 10% solution of Ti(III)Cl in 20-30% hydrochloric acid. After 3 hours, another 2 ml of the approximately 10% solution of Ti(III)Cl in 20-30% hydrochloric acid is added and stirred overnight at room temperature. The batch is made basic with 1N NaOH solution and mixed with ethyl acetate. It is filtered, and the filter cakes are washed with ethyl acetate/MeoH (3:2). The organic solvent is drawn off in a rotary evaporator, and the residue is extracted from ethyl acetate. The combined organic phases are dried ($Na_2SO_4$), filtered and concentrated by evaporation. The residue that is obtained is purified by chromatography (DCM/EtOH 95:5). 0.82 mg (0.48 mmol, corresponding to 48% of theory) of the product is obtained.

$^1$H-NMR (DMSO): 7.19 (m, 1H), 7.11 (m, 1H), 7.00 (m, 1H), 6.75 (m, 1H), 5.56 (s, 2H), 3.96 (s, 1H), 2.98 (s, 3H). ES: 171 (ES).

e) Production of (RS)-S-(3-aminophenyl)-S-methyl-N-nitrosulfoximide

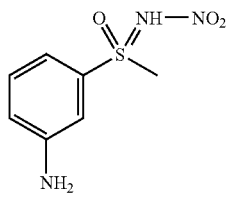

A solution of 100 mg (0.41 mmol) of (RS)-S-methyl-N-nitro-S-(3-nitrophenyl)sulfoximide in 8 ml of THF is mixed at room temperature with 3.1 ml of an approximately 10% solution of Ti(III)Cl in 20-30% hydrochloric acid. After 1 hour, another 1.0 ml of the approximately 10% solution of Ti(III)Cl in 20-30% hydrochloric acid is added, and it is stirred for another 45 minutes at room temperature. The batch is made basic with 1N NaOH solution and extracted with ethyl acetate. The combined organic phases are dried (Na$_2$SO$_4$), filtered and concentrated by evaporation. The residue that is obtained is purified by chromatography (DCM/EtOH 95:5). 40 mg (0.19 mmol, corresponding to 45% of theory) of the product is obtained.

$^1$H-NMR (DMSO): 7.33 (m, 1H), 7.13 (m, 1H), 7.03 (m, 1H), 6.90 (m, 1H), 5.88 (s, 2H), 3.59 (s, 3H). ES: 216 (ES).

f) Production of (RS)-S-methyl-N-nitro-S-(3-nitrophenyl)sulfoximide (A) and (RS)—S-methyl-S-(3-nitrophenyl)sulfoximide (B)

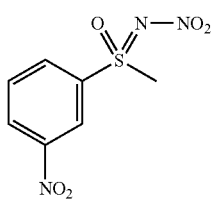
A

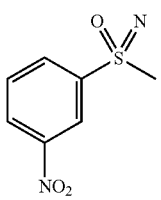
B 1.0 g (6.45 mmol) of (RS)-S-phenyl-S-methyl sulfoximide is carefully mixed with 3 ml of concentrated sulfuric acid. While being stirred at 0° C., the batch is carefully mixed drop by drop with 1 ml of fuming nitric acid and slowly heated overnight to room temperature. The reaction solution is carefully added to ice-cooled 1N NaOH solution. The basic batch is extracted from ethyl acetate. The combined organic phases are dried (Na$_2$SO$_4$) and concentrated by evaporation. The residue that is obtained is mixed with 15 ml of MeOH. The precipitate that is formed is suctioned off and washed with diisopropyl ether. After drying, 485 mg (1.98 mmol, corresponding to 31% of theory) of product A is obtained. The filtrate is spun in, and the precipitate that is formed is purified by chromatography (DCM/EtOH 97:3). 200 mg (1.00 mmol, corresponding to 16% of theory) of product B is obtained.

(A):
$^1$H-NMR (DMSO): 8.79 (m, 1H), 8.64 (m, 1H), 8.49 (m, 1H), 8.05 (m, 1H), 3.88 (s, 3H).

(B):
$^1$H-NMR (DMSO): 8.65 (1,1H), 8.48 (m, 1H), 8.35 (m, 1H), 7.90 (m, 1H), 4.62 (s, 1H), 3.17 (s, 3H). MS: 201 (ES).

g) Production of 5-bromo-N$^4$-isopropyl-N$^2$-[4-(methylsulfinyl)phenyl]-pyrimidine-2,4-diamine

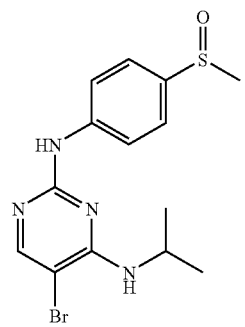

1.77 g (4.6 mmol) of 5-bromo-N$^4$-isopropyl-N$^2$-[4-(methylsulfanyl)phenyl]-pyrimidine-2,4-diamine hydrochloride is taken up in 40 ml of DCM and mixed with 1.73 g (5.5 mmol) of 3-chloroperoxybenzoic acid (55%). The batch is stirred for 90 minutes at room temperature and then diluted with DCM. It is washed with saturated NaHCO$_3$ solution and saturated NaCl solution. The organic phase is dried (Na$_2$SO$_4$), filtered and concentrated by evaporation. The remaining residue is purified by chromatography (DCM/EtOH 9:1). 553 mg (1.5 mmol, corresponding to 33% of theory) of the product is obtained.

$^1$H-NMR (DMSO): 9.55 (s, 1H), 8.08 (s, 1H), 7.90 (d, 2H), 7.53 (d, 2H), 6.53 (d, 1H), 4.35 (m, 1H), 2.70 (s, 3H), 1.25 (d, 6H). MS: 369 (ES).

h) Production of 5-Bromo-N$^4$-isopropyl-N$^2$-[4-(methylsulfanyl)phenyl]-pyrimidine-2,4-diamine

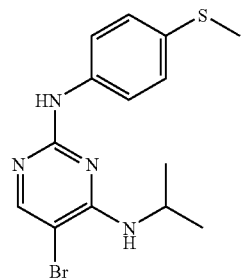

A solution of 4.08 g (16.3 mmol) of (5-bromo-2-chloropyrimidin-4-yl)-isopropyl-amine in 20 ml of acetonitrile is mixed at room temperature with a solution of 2 ml (16.3 mmol) of 4-methylsulfanyl-phenylamine in 10 ml of acetonitrile. The batch is mixed with 4.1 ml of a 4 molar solution of hydrochloric acid in dioxane and 4.1 ml of water, and then it is stirred under reflux for 16 hours. After cooling, the precipitate that is formed is suctioned off, washed with water and dried. 4.94 g (12.7 mmol, corresponding to 78% of theory) of the product is obtained in the form of hydrochloride.

¹H-NMR (DMSO): 10.39 (s, 1H), 8.18 (s, 1H), 7.88 (br, 1H), 7.49 (d, 2H), 7.29 (d, 2H), 4.30 (m, 1H), 2.5 (s, 3H), 1.21 (d, 6H). MS: 353 (ES).

Additional Intermediate Products

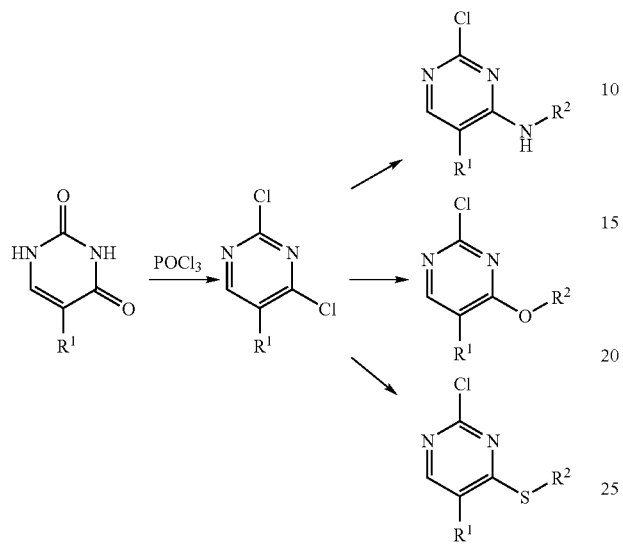

Substituents R¹ and R² have the meaning that is indicated in general formula (I).

i) Production of (R)-2-[(5-Bromo-2-chloropyrimidin-4-yl)amino]propan-1-ol

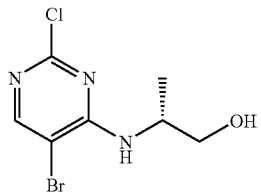

A solution of 22.8 g (100 mmol) of 5-bromo-2,4-dichloropyrimidine in 100 ml of acetonitrile is mixed at 0° C. first with 17.0 ml (125 mmol) of triethylamine and then with 9.4 g (125 mmol) of D-alaninol. The batch is stirred overnight at room temperature. The precipitate that is formed is suctioned off, washed with water, and completely dried. 21.5 g (81 mmol, corresponding to 81% of theory) of the product is obtained.

¹H-NMR (DMSO): 8.21 (s, 1H), 7.05 (d, 1H), 4.86 (t, 1H), 4.16 (m, 1H), 3.41 (m, 2H), 1.17 (d, 3H).

j) Production of (2R,3R)-3-[(5-bromo-2-chloropyrimidin-4-yl)oxy]-butan-2-ol

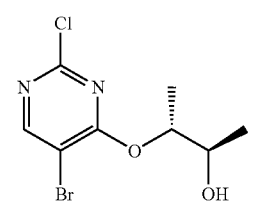

A solution of 1.35 g (15.0 mmol) of (R,R)-(−)-2,3-butanediol in 50 ml of THF is mixed at 0° C. in portions with 480 mg (11.0 mmol) of sodium hydride (55% dispersion) and then stirred for 10 minutes at room temperature. The solution that is produced is added at 0° C. to 2.27 g (10.0 mmol) of 5-bromo-2,4-dichloropyrimidine in 25 ml of THF. The batch is slowly heated to room temperature and stirred for 12 hours. The solvent is drawn off, and the residue that is obtained is purified by chromatography (hexane/ethyl acetate 1:1). 2.29 g (8.1 mmol, corresponding to 81% of theory) of the product is obtained.

¹H-NMR (DMSO): 8.44 (s, 1H), 5.18 (q, 1H), 3.96 (q, 1H), 2.02 (d, 1H), 1.4 (d, 3H), 1.28 (d, 3H). MS: 281 (ES).

k) Production of (R)-3-[(5-bromo-2-chloropyrimidin-4-yl)amino]-2-methyl-butan-2-ol

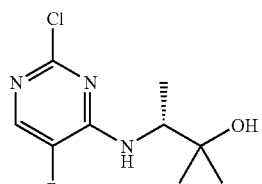

An ice-cooled solution of 2.95 g (10.0 mmol) of methyl-N-(5-bromo-2-chloropyrimidin-4-yl)-D-alaninate in 150 ml of THF is mixed drop by drop with 30 ml (90 mmol) of a 3 molar solution of methylmagnesium bromide in diethyl ether. After 2.5 hours at room temperature, the batch is mixed with 30 ml of saturated ammonium chloride solution. It is diluted with water and extracted from ethyl acetate (3×). The combined organic phases are dried (Na₂SO₄), filtered and concentrated by evaporation. The remaining residue is purified by chromatography (hexane/ethyl acetate: 4: 1-1:1). 2.81 g (9.5 mmol, corresponding to 95% of theory) of the product is obtained.

¹H-NMR (CDCl₃): 8.1 (s, 1H), 5.9 (d, 1H), 4.2 (m, 1H), 1.8 (br, 1H), 1.2 (m, 9H).

ka) Production of methyl-N-(5-bromo-2-chloropyrimidin-4-yl)-D-alaninate

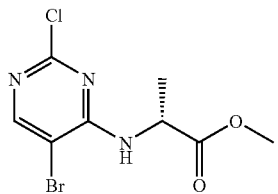

22.8 g (100 mmol) of 5-bromo-2,4-dichloropyrimidine and 14.0 g (100 mmol) of D-alanic acid methyl ester hydrochloride are dissolved in 300 ml of THF and 75 nil of DMF. The ice-cooled batch is mixed with 33.5 ml (240 mmol) of triethylamine and then slowly heated to room temperature. After 48 hours, the solvent is drawn off in a rotary evaporator, and the remaining residue is purified by chromatography (hexane/ethyl acetate: 4:1-2:1). 25.5 g (86.1 mmol, corresponding to 86% of theory) of the product is obtained.

¹H-NMR (CDCl₃): 8.2 (s, 1H), 6.1 (d, 1H), 4.8 (m, 1H), 3.8 (s, 3H), 1.6 (d, 3H).

l) Production of (2R,3R)-3-[(5-bromo-2-chloropyrimidin-4-yl)amino]butan-2-ol

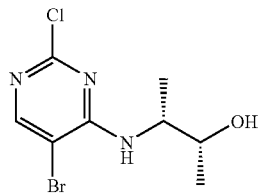

32.7 g (159 mmol) of copper(I)bromide dimethyl sulfide complex is introduced under nitrogen atmosphere into 1000 ml of diethyl ether and cooled to −78° C. Over a period of about 25 minutes, 200 ml of a 1.6 molar solution of methyllithium in diethyl ether is added in drops, and then the cooling bath is removed. The batch is stirred for 40 minutes, and the temperature increases to −35° C. It is cooled to −55° C., and 18.9 g (71.5 mmol) of (R)-2-[(5-bromo-2-chloropyrimidin-4-yl)amino]propanal is added over a period of 20 minutes. It is stirred for 6 hours at −55° C., then the cooling bath is filled with dry ice again, covered with aluminum foil, and the batch is stirred overnight. 200 ml of a saturated ammonium chloride solution is added in drops, and the batch is heated to room temperature. It is diluted with 500 ml of diethyl ether, the organic phase is separated, and the aqueous phase is extracted with diethyl ether. The combined organic phases are washed with saturated ammonium chloride solution and saturated NaCl solution, dried ($Na_2SO_4$), filtered and concentrated by evaporation. The remaining residue is purified by chromatography (hexane/ethyl acetate: 4:1-1:1). 8.4 g (30.0 mmol, corresponding to 42% of theory) of the product is obtained.

$^1$H-NMR ($CDCl_3$): 8.1 (s, 1H), 5.8 (d, 1H), 4.2 (m, 1H), 3.9 (m, 1H), 2.0 (d, 1H), 1.3 (d, 3H), 1.2 (d, 3H).

HPLC Analysis:

| Column: | Chiralpak AD-H 5µ |
|---|---|
| Length × ID: | 150 × 4.6 mm |
| Eluants: | A = Hexane, C = Ethanol |
| Flow: | 1.0 ml/min |
| Gradient: | Isocratic 5% C |
| Detector: | UV 254 nm |
| Temperature: | 25° C. |
| RT in min: | 6.04 | la) Production of (R)-2-[(5-bromo-2-chloropyrimidin-4-yl)amino]propanal

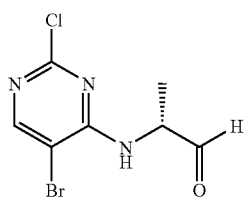

A solution of 40.0 g (135.8 mmol) of methyl-N-(5-bromo-2-chloropyrimidin-4-yl)-D-alaninate in 800 ml of toluene is mixed at −78° C. with 310 ml of a 1.2 molar solution of diisobutyl aluminum hydride. After 30 minutes, it is carefully quenched with methanol. The batch is heated to room temperature and diluted with 1000 ml of tert-butyl methyl ether. It is washed successively with 1N HCl (3×100 ml), saturated sodium bicarbonate solution (3×) and saturated NaCl solution (3×). The organic phase is dried ($MgSO_4$), filtered and concentrated by evaporation. The remaining residue is purified by chromatography (hexane/ethyl acetate: 4:1-1:1). 22.5 g (83.9 mmol, corresponding to 62% of theory) of the product is obtained.

$^1$H-NMR ($CDCl_3$): 9.6 (s, 1H), 8.2 (s, 1H), 6.3 (d, 1H), 4.8 (m, 1H), 1.5 (d, 3H).

lb) Production of (2R,3R)-3-[(5-bromo-2-chloropyrimidin-4-yl)amino]4-methoxybutan-2-ol

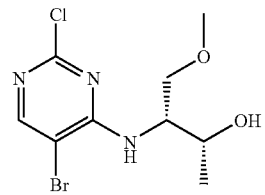

311 mg (2.6 mmol) of (2R,3R)-3-amino-4-methoxy-butan-2-ol hydrochloride (production according to A. I. Meyers, D. Hoyer, Tet. Lett. 1985, 26, 4687) in 2 ml of acetonitrile is mixed with 0.28 ml of triethylamine and shaken. It is filtered, and the filter cakes are washed with 2 ml of acetonitrile. The filtrate is added in drops to a solution of 455 mg (2.0 mmol) of 5-bromo-2,4dichloro-pyrimidine in 26 ml of acetonitrile at −30° C. By removal of the cooling bath, it is slowly heated to room temperature while being stirred. After 16 hours, the solvent is drawn off in a rotary evaporator, and the remaining residue is purified by chromatography (hexane/ethyl acetate: 4:1-1:1). 509 mg (1.6 mmol, corresponding to 80% of theory) of the product is obtained.

$^1$H-NMR ($CDCl_3$): 8.1 (s, 1H), 6.3 (d, 1H), 4.3 (m, 1H), 4.2 (m, 1H), 3.8 (d, 2H), 3.4 (s, 3H), 3.1 (d, 3H), 1.2 (d, 3H).

lc) Production of 5-bromo-2-chloropyrimidin-4-ol

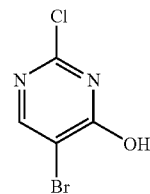

50.5 g of 5-bromo-2,4-dichloropyrimidine is mixed with 133 ml of 2N sodium hydroxide solution and stirred for 50 minutes at 45-50° C. After cooling, it is acidified with 21 ml of concentrated hydrochloric acid while being cooled with ice. The precipitate is suctioned off, washed with water and a little methylene chloride and dried at 25-35° C. 17.12 g (36.9% of theory) of the product with a melting point of 136-145° C. (decomposition) is obtained.

Produced in a way that is similar to the above-described process variants in each case are also the compounds below:

| Example | m | ma | mb |
|---|---|---|---|
| MS | 250 (CI) | 293 (EI) | 341 (EI) | n) Production of 5-bromo-2-[4-(methylsulfanyl)phenylamino]pyrimidin-4-ol

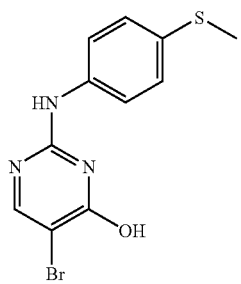

9.8 g of 5-bromo-2-chloropyrimidin-4-ol is suspended in 200 ml of acetonitrile. After 7.2 g of 4-methylsulfanyl-phenylamine is added, 12 ml of a 4N solution of HCl in dioxane is added in drops while being stirred vigorously. After drop-by-drop addition of 5 ml of water, the mixture is stirred for 3 hours at 78° C. and for 2 days at room temperature. The mixture is cooled in an ice bath and suctioned off. The filter cake is washed twice with acetonitrile and dried. 15.2 g (92.7% of theory) of the product with a melting point of 238° C. (decomposition) is obtained.

o) Production of (RS)-5-bromo-2-[4-(methylsulfinyl)phenylamino]pyrimidin-4-ol

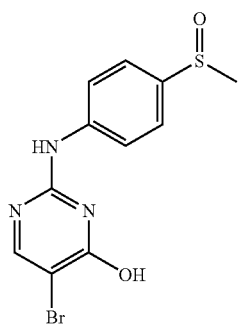

11 g of 5-bromo-2-[4-(methylsulfanyl)phenylamino]pyrimidin-4-ol is suspended in 110 ml of glacial acetic acid. While being cooled with ice water, 4.6 ml of a 30% solution of hydrogen superoxide is added in drops. The mixture is stirred for 18 hours at room temperature and then suctioned off. The filter cake is washed twice with water and once with ethanol and dried at 60° C. in a vacuum. 8.75 g (75.7% of theory) of the product with a melting point of 240° C. (decomposition) is obtained.

p) Production of (RS)-S-{4-[(5-bromo-4-hydroxy-pyrimidin-2-yl)amino]phenyl}-S-methyl sulfoximide

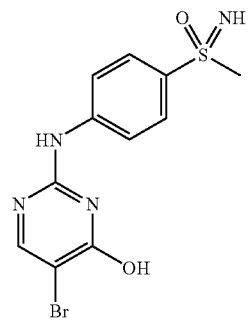

324 mg of (RS)-5-bromo-2-[4-(methylsulfinyl)phenylamino]pyrimidin-4-ol and 128 mg of sodium azide are suspended in 6 ml of methylene chloride and mixed drop by drop with 0.3 ml of concentrated sulfuric acid while being cooled with ice. The mixture is stirred for 36 hours at 40° C. The organic phase is decanted off, and the residue is stirred with ice water. The solid is suctioned off, washed twice with water and once with ethanol and dried. 266 mg (78.2% of theory) of the product with a melting point of 230° C. (decomposition) is obtained.- q) Production of (RS)-S-{4-[(5-bromo-4-chloropyrimidin-2-yl)amino]phenyl}-S-methyl sulfoximide

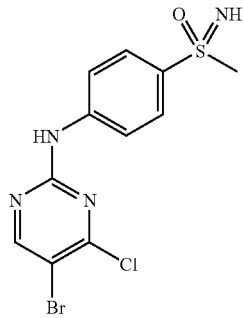

255 mg of (RS)-S-{4-[(5-bromo-4-hydroxypyrimidin-2-yl)amino]phenyl}-S-methyl sulfoximide is suspended in 1.5 ml of phosphorus oxychloride and stirred for 3 hours at 106° C. and for 16 hours at room temperature. The mixture is poured into ice water, made alkaline with 25% ammonia solution while being cooled intensely (temperature <5° C.) and stirred for 1 hour in an ice bath. The precipitate is suctioned off, washed with water and dried at 60° C. 220 mg (81.8% of theory) of the product with a melting point of 170-173° C. is obtained.

r) Production of (RS)-S-(4-aminophenyl)-S-cyclopropyl-N-[2-(trimethylsilyl)ethylsulfonyl]sulfoximide

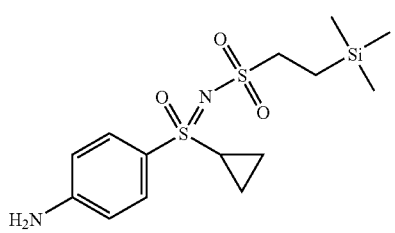

320 mg of (RS)-S-cyclopropyl-S-(4-nitrophenyl)-N-[2-(trimethylsilyl)ethyl-sulfonyl]sulfoximide is dissolved in 5 ml of tetrahydrofuran. While being cooled with ice, 7.2 ml of an approximately 10% by weight solution of titanium(III) chloride in 20-30% by weight of hydrochloric acid is added in drops. The solution is stirred for 16 hours at room temperature and poured onto ice. The pH is set at 8-9 with 15% sodium hydroxide solution. After ethyl acetate is added, the mixture is vigorously stirred. The precipitate is suctioned off and washed with 100 ml of ethyl acetate. The filtrates are combined, dried and concentrated by evaporation. After purification by flash chromatography, 215 mg of (RS)-S-(4-aminophenyl)-S-cyclopropyl-N-[2-(trimethylsilyl)ethylsulfonyl]sulfoximide is obtained.

Melting point: 137-138° C.

Produced in a similar way are also (RS)-S-(4-aminophenyl)-S-cyclopropyl-methyl-N-[2-(trimethylsilyl)ethylsulfonyl]sulfoximide (melting point: 138-140° C.) and (RS)-S-(4-aminophenyl)-S-cyclopentyl-N-[2-(trimethylsilyl)ethylsulfonyl]sulfoximide (melting point: 146-147° C.).

s) Production of (RS)-S-cyclopropyl-S-(4-nitrophenyl)-N-[2-(trimethylsilyl)ethyl-sulfonyl]sulfoximide

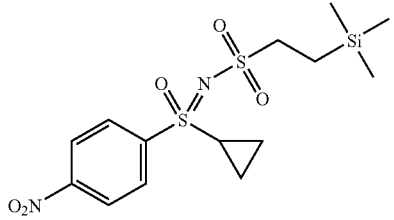

260 mg of (RS)-1-(cyclopropylsulfinyl)-4-nitrobenzene is dissolved in 10 ml of acetonitrile, mixed with 100 mg of tetrakis-(acetonitrile)-copper(I)-hexafluorophosphate and stirred for 45 minutes at room temperature. The solution is cooled in an ice bath and mixed with 613 mg of [N-(2-(trimethylsilyl)ethanosulfonyl)imino]phenyliodinane (PhI=NSes: J. Org. Chem., 64(14), 5304-5307 (1999)). After 30 minutes of stirring at 0° C., another 232 mg of PhI=NSes is added. After 2 hours of stirring at 0° C., another 60 mg of PhI=NSes and 10 mg of tetrakis-(acetonitrile)-copper(I)-hexafluorophosphate is added. After 30 minutes of stirring at 0° C., the mixture is concentrated by evaporation. The oily residue is mixed with hexane, whereby the product crystallizes. The solution is decanted off, and the solid is purified by flash chromatography (hexane/ethyl acetate). 325 mg of (RS)-S-cyclopropyl-S-(4-nitrophenyl)-N-[2-(trimethylsilyl)ethylsulfonyl]-sulfoximide is obtained.

Melting point: 111-114° C.

t) Production of (RS)-1-(cyclopropylsulfinyl)4-nitrobenzene

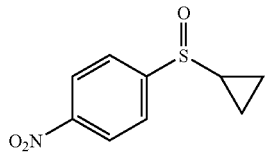

350 mg of 1-(cyclopropylsulfanyl)-4-nitrobenzene is dissolved in 5 ml of acetonitrile and mixed with 10 mg of iron(III)-chloride hexahydrate. After 10 minutes of stirring at room temperature, 450 mg of periodic acid is added thereto while being cooled. The mixture is stirred for 30 minutes at room temperature, cooled in an ice bath and mixed drop by drop with semi-saturated sodium disulfite solution. It is diluted with methylene chloride, washed with water, sodium bicarbonate solution and saturated sodium chloride solution, and concentrated by evaporation. After purification by flash chromatography, 270 mg of (RS)-1-(cyclopropylsulfinyl)-4-nitrobenzene is obtained.

Melting point: 104-106° C.

Produced in a similar way are:

ta) Production of (RS)-1-(ethylsulfinyl)-4-nitrobenzene

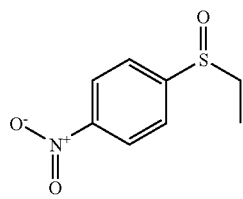

$^1$H-NMR (DMSO): 8.39 (m, 2H), 7.91 (m, 2H), 3.18 (m, 1H), 2.88 (m, 1H), 1.06 (tr, 3H).

tb) Production of (RS)-2-[(4-nitrophenyl)sulfinyl]ethanol

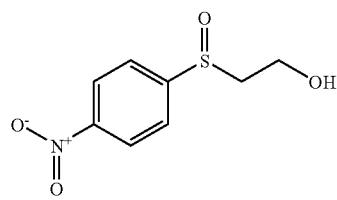

$^1$H-NMR (DMSO): 8.41 (m, 2H), 7.93 (m, 2H), 5.13 (tr, 1H), 3.84 (m, 1H), 3.78 (m, 1H), 3.16 (m, 1H), 2.95 (m, 1H). MS: 216 (ES).

tc) Production of (RS)-1-(isopropylsulfinyl)-4-nitrobenzene

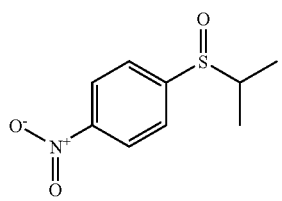

$^1$H-NMR (DMSO): 8.39 (m, 2H), 7.88 (m, 2H), 3.10 (m, 1H), 1.25 (d, 3H), 0.88 (d, 3H).

td) Production of (RS)-2-methyl-1-(methylsulfinyl)-4-nitrobenzene

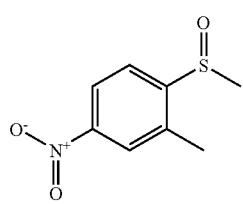

$^1$H-NMR (DMSO): 8.31 (m, 1H), 8.19 (m, 1H), 8.04 (m, 1H), 2.78 (s, 3H), 2.45 (s, 3H). MS: 200 (ES).

te) Production of (RS)-1-(methylsulfinyl)-4-nitro-2-(trifluoromethyl)benzene

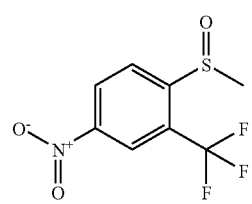

$^1$H-NMR (DMSO): 8.78 (m, 1H), 8.50 (m, 2H), 2.83 (s, 3H). MS: 270 (ES).

tf) Production of (RS)-2-fluoro-1-(methylsulfinyl)-4-nitrobenzene

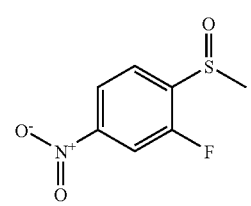

$^1$H-NMR (DMSO): 8.33 (m, 2H), 7.99 (m, 1H), 2.90 (s, 3H). MS: 204 (ES).

u) Production of 1-(cyclopropylsulfanyl)-4-nitrobenzene

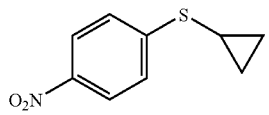

The cyclization of 1-(3-chloro-propylsulfanyl)-4-nitrobenzene was performed as described in J. Org. Chem., 33(1), 43-47 (1968).

$^1$H-NMR (DMSO): 8.18 (d, 2H), 7.60 (d, 2H), 2.40 (m, 1H), 1.21 (m, 2H), 0.66 (m, 2H). MS (CI): 195 (M$^+$, 12%), 213 (M$^+$+1+NH$_3$, 100%), 230 (M$^+$+1+2 NH$_3$, 44%).

v) Production of 1-[(3-chloropropyl)sulfanyl]4-nitrobenzene

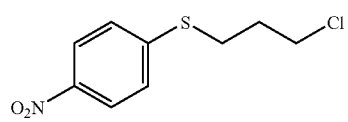

1 g of potassium hydroxide is dissolved in 40 ml of methanol and mixed with 2.3 g of 4-nitrothiophenol. The suspension is stirred for one hour at room temperature and mixed drop by drop with 1.48 ml of 1-bromo-3-chloropropane. After 4 hours of stirring at room temperature, another 0.15 ml of 1-bromo-3-chloropropane is added in drops. The mixture is stirred for 65 hours at room temperature, concentrated by evaporation in a vacuum and taken up in ethyl acetate. It is extracted with water and saturated common salt solution, dried on sodium sulfate and concentrated by evaporation. After purification by flash chromatography, 2.54 g of 1-(3-chloro-propylsulfanyl)-4-nitro-benzene is obtained.

$^1$H-NMR (DMSO): 8.16 (d, 2H), 7.55 (d, 2H), 3.77 (t, 2H), 3.25 (t, 2H), 2.08 (q, 2H). MS (ES): 232 (100%), 234 (38%).

Produced in a similar way are also 1-cyclopropylmethylsulfanyl-4-nitro-benzene (from (chloromethyl)-cyclopropane) and 1-cyclopentylsulfanyl-4-nitro-benzene (from bromocyclopentane).

w) Production of (RS)-S-(2-hydroxyethyl)-S-(4-nitrophenyl)-N-[2-(trimethylsilyl)ethylsulfonyl]sulfoximide

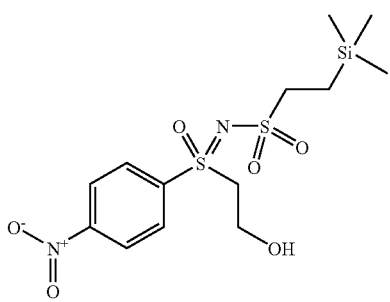

$^1$H-NMR (DMSO): 8.48 (m, 2H), 8.24 (m, 2H), 4.97 (tr, 1H), 3.99 (tr, 2H), 3.79 (m, 2H), 3.00 (dd, 2H), 0.96 (m, 2H), 0.05 (s, 9H).

x) Production of (RS)-S-(4-amino-2-methoxyphenyl)-S-methylsulfoximide

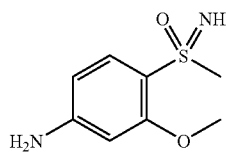

1.5 g (6.5 mmol) of (RS)-S-(2-methoxy-4-nitrophenyl)-S-methylsulfoximide in 100 ml of ethanol is mixed with 300 mg of palladium on carbon (10%×50% H$_2$O) and hydrogenated for 45 minutes at room temperature and normal pressure. The batch is filtered and concentrated by evaporation. 1.0 g (5.1 mmol, corresponding to 79% of theory) of the product is obtained.

$^1$H-NMR (DMSO-D6): 7.10 (m, 1H), 6.92 (m, 1H), 6.73 (m, 1H), 4.70 (br, 3H), 3.76 (s, 3H), 3.13 (s, 3H). MS: 201 (ES).

y) Production of (RS)-S-(2-methoxy-4-nitrophenyl)-S-methyl sulfoximide

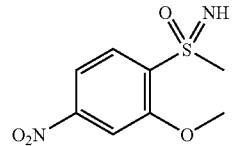

7.5 g of fuming nitric acid is cooled to −10° C. and slowly mixed with 5.0 g (32.4 mmol) of 1-methoxy-2-methylsulfanyl-benzene. The batch is slowly heated to room temperature while being stirred, diluted with 100 ml of water and neutralized with sodium bicarbonate. It is extracted with diethyl ether and ethyl acetate. The combined organic phases are dried (Na$_2$SO$_4$), filtered and concentrated by evaporation.

5.3 g of the intermediate product that is obtained is mixed with 1.8 g (27.7 mmol) of sodium azide and 25 ml of CHCl$_3$. The batch is cooled to 0° C. and carefully mixed with 6.3 ml of concentrated sulfuric acid. It is heated first to room temperature and then to 45° C. The batch is stirred overnight at this temperature. After cooling, it is mixed with 75 ml of ice water and 20 ml of CHCl$_3$. The organic phase is separated, and the aqueous phase is extracted again with 100 ml of CHCl$_3$. The aqueous phase is made basic with 1N NaOH solution and then extracted from CHCl$_3$ (2×). The organic phases of the last extraction are combined, dried (Na$_2$SO$_4$), filtered and concentrated by evaporation. 3.8 g (16.5 mmol) of the product is obtained.

$^1$H-NMR (DMSO-D6): 8.66 (m, 1H), 8.48 (m, 1H), 7.45 (m, 1H), 4.70 (s, 1H), 4.08 (s, 3H), 3.21 (s, 3H). MS: 231 (ES).

z) Production of (RS)-S-(2-methyl-4-nitrophenyl)-S-methyl sulfoximide

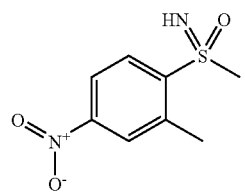

1.5 g (7.5 mmol) of (RS)-2-methyl-1-(methylsulfinyl)-4-nitrobenzene and 1.1 g (17.1 mmol) of sodium azide in 10.0 ml of CHCl$_3$ are carefully mixed at 0° C. with 2.2 ml of concentrated sulfuric acid. The batch is heated first to room temperature and then to 45° C. while being stirred vigorously. It is stirred for 116 hours at this temperature. After cooling, it is mixed with water and extracted from DCM (2×). The aqueous phase is made basic with 2N NaOH solution and extracted from DCM. The combined organic phases are filtered through a Whatman filter and concentrated by evaporation. The crude product that is obtained is recrystallized from ethyl acetate. 1.3 g (6.1 mmol, corresponding to 81% of theory) of the product is obtained.

$^1$H-NMR (DMSO): 8.28 (m, 1H), 8.22 (m, 2H), 4.67 (s, 1H), 3.17 (s, 3H), 2.81 (s, 3H). MS: 215 (ES).

za) Production of (RS)-S-methyl-S-[4-nitro-2-(trifluoromethyl)phenyl]sulfoximide

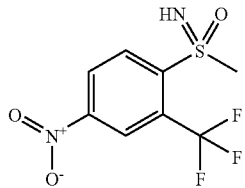

¹H-NMR (DMSO): 8.73 (m, 1H), 8.52 (m, 2H), 5.00 (s, 1H), 3.17 (s, 3H). MS: 269 (ES).

zb) Production of (RS)-S-(2-fluoro-4-nitrophenyl)-S-methyl sulfoximide

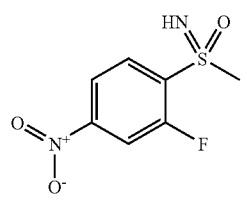

¹H-NMR (DMSO): 8.34 (m, 1H), 8.24 (m, 1H), 8.10 (m, 1H), 5.08 (s, 1H), 3.21 (s, 3H). MS: 219 (ES).

zc) Production of (RS)—N,S-dimethyl-S-(4-nitrophenyl)sulfoximide

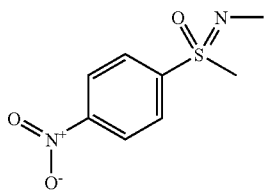

500 mg (2.5 mmol) of (RS)-S-(4-nitrophenyl)-S-methyl sulfoximide in 4 ml of formaldehyde (aqueous, 37%) and 20 ml of formic acid (98-100%) are stirred in an open flask at 100° C. After 22 hours, the solvent is evaporated, mixed again with 4 ml of formaldehyde (aqueous, 37%) and 20 ml of formic acid (98-100%) and stirred for another 22 hours at 100° C. Residue from the solvent is drawn off in a rotary evaporator. The remaining residue is dissolved with 2N HCl and extracted from DCM. The aqueous phase is made basic with NaHCO₃ and extracted from DCM. The combined organic phases are dried (Na₂SO₄), filtered and concentrated by evaporation. 448 mg (2.1 mmol, corresponding to 85% of theory) of the product is obtained.

¹H-NMR (DMSO-D6): 8.43 (m, 2H), 8.08 (m, 2H), 3.24 (s, 3H), 2.48 (s, 3H). MS: 214 (ES).

zd) Production of (RS)-N-(ethoxycarbonyl)-S-methyl-S-(4-nitrophenyl)sulfoximide

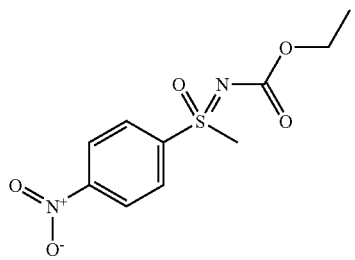

8.50 g (42.5 mmol) of (RS)-S-(4-nitrophenyl)-S-methyl sulfoximide in 400 ml of pyridine is mixed drop by drop at room temperature with 18.8 ml (197.2 mmol) of ethyl chloroformate. The batch is stirred for 4 hours at room temperature and then added in dilute NaCl solution. It is extracted from ethyl acetate. The combined organic phases are dried (Na₂SO₄), filtered and concentrated by evaporation. The remaining residue is purified by chromatography (hexane/ethyl acetate 1:1). 8.94 g (32.8 mmol, corresponding to 77% of theory) of the product is obtained.

¹H-NMR (DMSO-D6): 8.49 (m, 2H), 8.22 (m, 2H), 3.90 (m, 2H), 3.56 (s, 3H), 1.10 (tr, 3H).

ze) Production of (RS)-S-ethyl-N-({[(1R,2S,5R)-2-isopropyl-5-methyl-cyclohexyl]oxy}carbonyl)-S-(4-nitrophenyl)sulfoximide

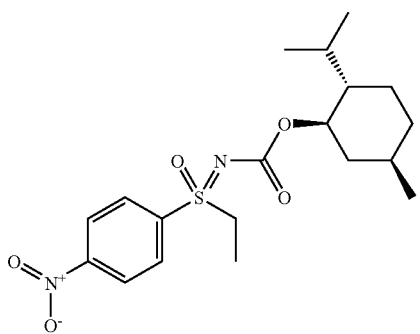

100 mg (0.47 mmol) of (RS)-S-(4-nitrophenyl)-S-ethyl sulfoximide in 4.40 ml of pyridine is mixed drop by drop at room temperature with 0.46 ml (2.17 mmol) of (+) menthyl chloroformate. The batch is stirred for 4 hours at room temperature and then added to dilute NaCl solution. It is extracted from ethyl acetate. The combined organic phases are dried (Na₂SO₄), filtered and concentrated by evaporation. The remaining residue is purified by chromatography (hexane/ethyl acetate 1:1). 161 mg (0.41 mmol, corresponding to 87% of theory) of the product is obtained.

¹H-NMR (DMSO-D6): 8.49 (m, 2H), 8.13 (m, 2H), 4.28 (m, 1H), 3.67 (m, 2H), 1.77 (m, 1H), 1.55 (m, 2H), 1.25 (m, 6H), 0.75 (m, 12H).

zf) Production of (RS)-N-(ethoxycarbonyl)-S-ethyl-S-(4-nitrophenyl)sulfoximide

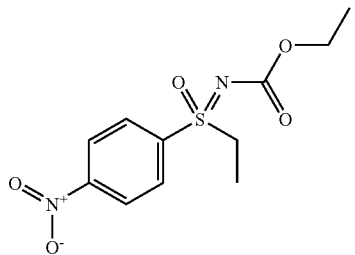

$^1$H-NMR (DMSO-D6): 8.48 (m, 2H), 8.15 (m, 2H), 3.92 (m, 2H), 3.69 (m, 2H), 1.12 (m, 6H).

zg) Production of (RS)-N-(ethoxycarbonyl)-S-methyl-S-(2-methyl-4-nitrophenyl)sulfoximide

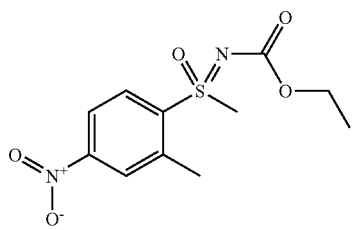

$^1$H-NMR (DMSO): 8.33 (m, 2H), 8.17 (m, 1H), 3.90 (q, 2H), 3.55 (s, 3H), 2.73 (s, 3H), 1.08 (tr, 3H). MS: 287 (ES).

zh) Production of (RS)-N-(ethoxycarbonyl)-S-(2-fluoro-4-nitrophenyl)-S-methyl sulfoximide

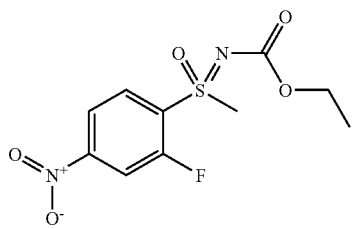

$^1$H-NMR (DMSO): 8.45 (m, 1H), 8.33 (m, 1H), 8.19 (m, 1H), 3.40 (m, 2H), 3.60 (s, 3H), 1.04 (tr, 3H).

zi) Production of (RS)-N-(ethoxycarbonyl)-S-methyl-S-[4-nitro-2-(trifluoromethyl)phenyl]sulfoximide

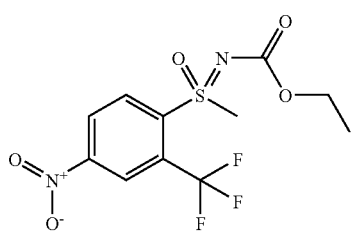

$^1$H-NMR (DMSO): 8;78 (m, 1H), 8.65 (m, 1H), 8.49 (m, 1H), 3.90 (q, 2H), 3.58 (s, 3H), 1.07 (tr, 3H).

zj) Production of (RS)-S-(4-aminophenyl)-N-(ethoxycarbonyl)-S-methyl sulfoximide

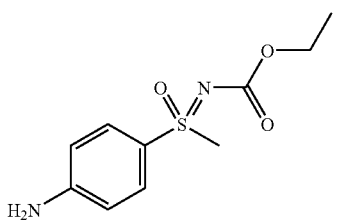

A solution of 8.70 g (32.0 mmol) of (RS)-N-(ethoxycarbonyl)-S-methyl-S-(4-nitrophenyl)sulfoximide in 650 ml of THF is slowly mixed at room temperature with 435 ml of a 10% solution of Ti(III)Cl in approximately 10% hydrochloric acid (Aldrich). The batch is stirred for 4 hours at room temperature and then cooled to 0° C. 450 ml of a 32% NaOH solution is added in drops. In this case, the reaction mixture is now diluted by the addition of water and ethyl acetate. It is mixed with 500 ml of ethyl acetate, and the organic phase is separated. The pulpy, aqueous phase is extracted from ethyl acetate. The combined organic phases are washed with dilute NaCl solution, dried ($Na_2SO_4$), filtered and concentrated by evaporation. 8.05 g (about 32.0 mmol) of the product is obtained, and said product is used without further purification.

$^1$H-NMR (DMSO-D6): 7.52 (m, 2H), 6.66 (m, 2H), 6.17 (m, 2H), 3.91 (q, 2H), 3.30 (s, 3H), 1.12 (tr, 3H).

zk) Production of (RS)-S-(4-aminophenyl)-N-(ethoxycarbonyl)-S-ethyl sulfoximide

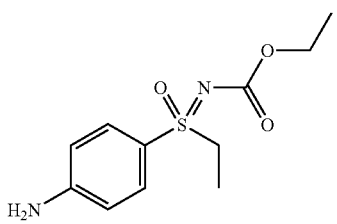

$^1$H-NMR (DMSO-D6): 7.47 (m, 2H), 6.67 (m, 2H), 6.20 (s, 2H), 3.90 (m, 2H), 3.42 (q, 2H), 1.10 (m, 6H).

zl) Production of (RS)-S-(4-aminophenyl)-S-(2-hydroxyethyl)-N-[2-trimethylsilyl)-ethylsulfonyl]sulfoximide

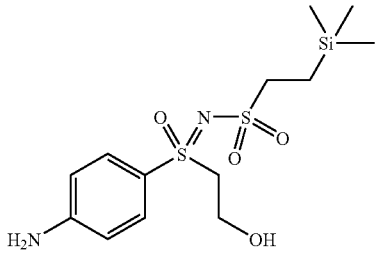

$^1$H-NMR (DMSO-D6): 7.54 (m, 2H), 6.68 (m, 2H), 6.30 (s, 2H), 4.90 (tr, 1H), 3.68 (m, 4H), 2.95 (m, 2H), 0.95 (m, 2H), 0.01 (s, 9H).

zm) Production of (RS)-S-(4-amino-2-methylphenyl)-N-(ethoxycarbonyl)-S-methyl sulfoximide

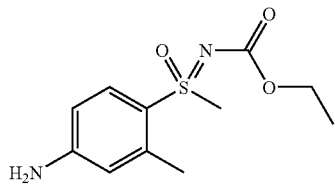

$^1$H-NMR (DMSO-D6): 7.53 (m, 1H), 6.48 (m, 2H), 6.04 (s, 2H), 3.90 (q, 2H), 3.30 (s, 3H), 2.42 (s, 3H), 1.13 (tr, 3H).

zn) Production of (RS)-S-(4-aminophenyl)-N,S-dimethyl sulfoximide

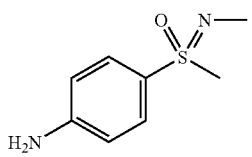

$^1$H-NMR (DMSO-D6): 7.48 (d, 2H), 6.62 (d, 2H), 5.95 (s, 2H), 2.95 (s, 3H), 2.41 (s, 3H).

zo) Production of (RS)-S-(4-amino-2-fluorophenyl)-N-(ethoxycarbonyl)-S-methyl sulfoximide

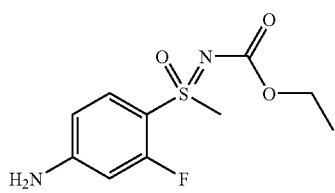

$^1$H-NMR (DMSO): 7.45 (m, 1H), 6.48 (m, 4H), 3.88 (m, 2H), 3.30 (s, 3H), 1.10 (tr, 3H).

zp) Production of (RS)-S-[4-amino-2-(trifluoromethyl)phenyl]-N-(ethoxycarbonyl)-S-methyl sulfoximide

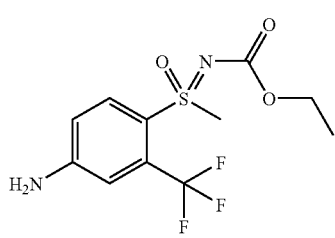

$^1$H-NMR (DMSO): 7.78 (m, 1H), 7.12 (m, 1H), 6.84 (m, 1H), 6.63 (s, 2H), 3.89 (q, 2H), 3.30 (s, 3H), 1.08 (tr, 3H). MS: 311 (ES).

The examples below describe the biological action of the compounds according to the invention without the invention being limited to these examples.

EXAMPLE 1

CDK1/CycB Kinase Assay

Recombinant CDK1- and CycB-GST-fusion proteins, purified from baculovirus-infected insect cells (Sf9), were purchased from ProQinase GmbH, Freiburg. Histone IIIS, used as a kinase substrate, is available commercially from the Sigma Company.

CDK1/CycB (200 ng/measuring point) was incubated for 15 minutes at 22° C. in the presence of various concentrations of test substances (0 μm, as well as within the range of 0.01-100 μm) in assay buffer [50 mmol of tris/HCl, pH 8.0, 10 mmol of MgCl$_2$, 0.1 mmol of Na ortho-vanadate, 1.0 mmol of dithiothreitol, 0.5 μm of adenosine triphosphate (ATP), 10 μg/measuring point of histone IIIS, 0.2 μCi/measuring point of $^{33}$P-gamma ATP, 0.05% NP40, 12.5% dimethyl sulfoxide]. The reaction was stopped by adding EDTA solution (250 mmol, pH 8.0, 14 μl/measuring point).

From each reaction batch, 10 μl was applied to P30 filter strips (Wallac Company), and non-incorporated 33P-ATP was removed by subjecting the filter strips to three washing cycles for 10 minutes each in 0.5% phosphoric acid. After the filter strips were dried for one hour at 70° C., the filter strips were covered with scintillator strips (MeltiLex™ A, Wallac Company) and baked for one hour at 90° C. The amount of incorporated 33P (substrate phosphorylation) was determined by scintillation measurement in a gamma-radiation measuring device (Wallac).

EXAMPLE 2

CDK2/CycE Kinase Assay

Recombinant CDK2- and CycE-GST-fusion proteins, purified from baculovirus-infected insect cells (Sf9), were purchased by ProQinase GmbH, Freiburg. Histone IIIs, which was used as a kinase substrate, was purchased by the Sigma Company.

CDK2/CycE (50 ng/measuring point) was incubated for 15 minutes at 22° C. in the presence of various concentrations of test substances (0 μm, as well as within the range of 0.01-100 μm) in assay buffer [50 mmol of tris/HCl, pH 8.0, 10 mmol of MgCl$_2$, 0.1 mmol of Na ortho-vanadate, 1.0 mmol of dithiothreitol, 0.5 μm of adenosine triphosphate (ATP), 10 μg/measuring point of histone IIIS, 0.2 μCi/measuring point of $^{33}$P-gamma ATP, 0.05% NP40, 12.5% dimethyl sulfoxide]. The reaction was stopped by adding EDTA solution (250 mmol, pH 8.0, 14 μl/measuring point).

From each reaction batch, 10 μl was applied to P30 filter strips (Wallac Company), and non-incorporated $^{33}$P-ATP was removed by subjecting the filter strips to three washing cycles for 10 minutes each in 0.5% phosphoric acid. After the filter strips were dried for one hour at 70° C., the filter strips were covered with scintillator strips (MeltiLex™ A, Wallac Company) and baked for one hour at 90° C. The amount of incorporated $^{33}$P (substrate phosphorylation) was determined by scintillation measurement in a gamma-radiation measuring device (Wallac).

EXAMPLE 3

VEGF Receptor-2 Kinase Assay

Recombinant VEGF receptor tyrosine kinase-2 was purified as a GST fusion protein from baculovirus-infected insect cells (Sf9). Poly-(Glu4Tyr), which was used as a kinase substrate, was purchased by the Sigma Company.

VEGF receptor tyrosine kinase (90 ng/measuring point) was incubated for 10 minutes at 22° C. in the presence of various concentrations of test substances (0 µm, as well as within the range of 0.001-30 µm) in 30 µl of assay buffer [40 mmol of Tris/HCl, pH 5.5, 10 mmol of MgCl2, 1 mmol of MnCl2, 3 µmol of Na ortho-vanadate, 1.0 mmol of dithiothreitol, 8 µmol of adenosine trisphosphate (ATP), 27 µg/measuring point of poly-(Glu4Tyr), 0.2 µCi/measuring point of 33P-gamma ATP, 1% dimethyl sulfoxide]. The reaction was stopped by adding EDTA solution (250 mmol, pH 7.0, 10 µl/measuring point).

From each reaction batch, 10 µl was applied to P30 filter strips (Wallac Company), and non-incorporated 33P-ATP was removed by subjecting the filter strips to three washing cycles for 10 minutes each in 0.5% phosphoric acid. After the filter strips were dried for one hour at 70° C., the filter strips were covered with scintillator strips (MeltiLex™ A, Wallac Company) and baked for one hour at 90° C. The amount of incorporated 33P (substrate phosphorylation) was determined by scintillation measurement in a gamma-radiation measuring device (Wallac). The IC50 values are determined from the inhibitor concentration, which is necessary to inhibit the phosphate incorporation to 50% of the uninhibited incorporation after removal of the blank reading (EDTA-stopped reaction).

EXAMPLE 4

Proliferation Assay

Cultivated human tumor cells (MCF7, hormone-independent human breast cancer cells, related to ATCC HTB22; NCI-H460, human non-small-cell lung cancer cells, ATCC HTB-177, HCT 116, human colon cancer cells, ATCC CCL-247; DU 145, hormone-independent human prostate cancer cells, ATCC HTB-81; MaTu-MDR, hormone-independent, multiple pharmaceutical agent-resistant human breast cancer cells, EPO-GmbH, Berlin) were flattened out at a density of about 5000 cells/measuring point, depending on the growth rate of the respective cells, in a 96-well multititer plate in 200 µl of the corresponding growth medium. After 24 hours, the cells of one plate (zero-point plate) were colored with crystal violet (see below), while the medium of the other plates was replaced by fresh culture medium (200 µl), to which the test substances were added in various concentrations (0 µm, as well as in the range of 0.01-30 µm; the final concentration of the solvent dimethyl sulfoxide was 0.5%). The cells were incubated for 4 days in the presence of test substances. The cell proliferation was determined by coloring the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were colored by adding 100 µl/measuring point of a 0.1% crystal violet solution (the pH was set at 3 by adding acetic acid). After three washing cycles of the colored cells with water, the plates were dried at room temperature. The dye was dissolved by adding 100 µl/measuring point of a 10% acetic acid solution. The extinction was determined by photometry at a wavelength of 595 nm. The change of cell growth, in percent, was calculated by normalization of the measured values to the extinction values of the zero-point plate (=0%) and the extinction of the untreated (0 µm) cells (=100%).

EXAMPLE 5

Carboanhydrase Assay

The principle of the assay is based on the hydrolysis of 4-nitrophenyl acetate by carboanhydrases (Pocker & Stone, *Biochemistry*, 1967, 6, 668), with subsequent photometric determination of the dye 4-nitrophenolate that is produced at 400 nm by means of a 96-channel spectral photometer.

2 µl of the test compounds, dissolved in DMSO (100× the final concentration), in a concentration range of 0.03-10 µm (final), was pipetted as 4× determinations into the holes of a 96-hole microtiter plate. Holes that contained the solvent without test compounds were used as reference values (1. Holes without carboanhydrase for correction of the non-enzymatic hydrolysis of the substrate, and 2. Holes with carboanhydrase for determining the activity of the non-inhibited enzyme).

188 µl of assay buffer (10 mmol of Tris/HCl, pH 7.4, 80 mmol of NaCl), with or without 3 units/hole on carboanhydrase I or II, was pipetted into the holes of the microtiter plate. The enzymatic reaction was started by the addition of 10 µl of the substrate solution (1 mmol of 4-nitrophenyl acetate (Fluka #4602), dissolved in anhydrous acetonitrile (final substrate concentration: 50 µm). The plate was incubated at room temperature for 15 minutes. The extinctions were measured by photometry at a wavelength of 400 nm. The enzyme inhibition was calculated after the measured values were normalized to the extinction of the reactions in the holes without enzyme (=100% inhibition) and to the extinction of reactions in the holes with non-inhibited enzyme (=0% inhibition).

The results from the examples and the comparison data are indicated in Tables 1 to 3 below. To demonstrate the superiority of the compounds according to the invention compared to the known compounds, the compounds according to the invention were compared to known reference compounds and a structurally similar known compound of Example 10 from WO 00/096888 in the enzyme test. The result is indicated in Tables 1 and 2 below. In Table 3, the improved data on the compounds according to the invention are shown in comparison to the compound of Example 10 from WO 00/12486 and acetazolamide.

TABLE 1

| | Proliferation IC$_{50}$ [µM] | | | | |
|---|---|---|---|---|---|
| Example No. | MCF7 | H460 | HCT116 | DU145 | MaTu-ADR |
| 1.0 | 0.3 | 1.2 | 0.4 | 1.5 | 1.6 |
| 2.0 | 1.5 | 0.3 | 0.3 | 1.7 | 0.4 |
| 1.3 | <0.1 | 0.14 | 0.10 | 0.2 | 0.17 |
| 1.4 | 0.06 | 0.06 | 0.05 | 0.10 | 0.08 |
| 1.2 | 0.11 | 0.03 | 0.02 | 0.04 | 0.04 |
| 2.1 | 0.9 | | | | |
| 2.3 | 0.3 | 0.4 | | 0.19 | 0.12 |
| 1.23 | 0.13 | <0.1 | | 0.1 | <0.1 |
| 1.24 | <0.1 | 0.07 | | 0.13 | 0.08 |
| 1.25 | <0.1 | | | | |
| 1.31 | 0.2 | 0.18 | | 0.3 | 0.7 |
| 1.41 | 0.08 | 0.07 | | 0.09 | 0.07 |
| 1.42 | 0.15 | <0.1 | | 0.17 | <0.1 |
| 1.7 | 1.1 | | | | |
| 1.26 | 0.06 | 0.03 | | 0.07 | 0.04 |

TABLE 1-continued

| Example No. | Proliferation IC$_{50}$ [μM] | | | | |
|---|---|---|---|---|---|
| | MCF7 | H460 | HCT116 | DU145 | MaTu-ADR |
| 1.27 | 0.06 | 0.02 | | 0.13 | 0.03 |
| 1.10 | 0.5 | 0.7 | | 0.8 | 0.8 |
| 1.39 | 0.3 | 0.3 | | 0.3 | 0.9 |
| 1.33 | 1 | | | | |
| 1.35 | 0.11 | 0.12 | | 0.12 | 0.3 |
| 1.34 | 0.8 | | | | |
| 1.40 | 0.11 | 0.17 | | 0.18 | 0.3 |
| 1.63 | 0.9 | | | | |
| 1.48 | 0.3 | 0.3 | | 0.4 | 0.6 |
| 1.54 | 0.11 | 0.12 | | 0.19 | 0.07 |
| 1.11 | 0.1 | <0.1 | | <0.1 | 0.1 |
| 1.9 | 0.1 | 0.11 | | 0.1 | 0.1 |
| 1.12 | 0.2 | 0.4 | | 0.3 | 2.8 |
| 1.6 | 0.14 | <0.1 | | <0.1 | <0.1 |
| 1.37 | 0.17 | <0.1 | | 0.16 | 0.3 |
| 1.57 | <0.1 | 0.12 | | 0.11 | 0.09 |
| 1.49 | 0.3 | 0.4 | | 0.3 | 0.6 |
| 1.50 | 1.2 | | | | |
| 1.55 | 0.3 | 0.3 | | 0.3 | 0.15 |
| 1.56 | 0.02 | 0.1 | | 0.07 | 0.05 |
| 1.46 | 0.2 | 0.11 | | 0.17 | 0.2 |
| 1.47 | 0.6 | 0.6 | | 0.6 | 0.8 |
| 1.16 | 0.18 | 0.2 | | 0.19 | 4.0 |
| 1.20 | 0.2 | 0.4 | | 0.4 | 2.1 |
| 1.38 | 0.12 | 0.06 | | 0.13 | 0.4 |
| 1.36 | 0.14 | 0.12 | | 0.17 | 1.2 |
| 1.51 | 0.08 | 0.05 | | 0.05 | 0.06 |
| 1.60 | 0.06 | 0.04 | | 0.04 | 0.04 |
| 1.14 | 0.09 | 0.10 | | 0.09 | 0.11 |
| 1.15 | 0.18 | 0.2 | | 0.3 | 0.3 |
| 1.32 | 0.19 | 0.18 | | 0.3 | 0.6 |
| 1.28 | 0.17 | 0.12 | | 0.2 | 0.2 |
| 3.4 | 1.0 | | | | |
| 3.5 | 0.12 | 0.05 | | 0.06 | 0.03 |
| 1.58 | 0.06 | 0.03 | | 0.03 | 0.04 |
| 1.59 | 0.11 | <0.1 | | <0.1 | <0.1 |
| 3.0 | 0.5 | | | | |
| 3.6 | 0.08 | 0.02 | | 0.02 | 0.02 |
| 3.7 | 0.1 | <0.1 | | <0.1 | <0.1 |
| 3.8 | 0.4 | 0.3 | | 0.3 | 0.19 |
| 3.1 | 0.4 | | | | |
| 1.29 | 0.17 | | | | |
| 1.30 | 0.17 | | | | |
| 3.10 | 0.4 | | | | |
| 3.9 | 1.0 | | | | |
| 1.18 | <0.1 | | | | |
| 1.21 | <0.1 | | | | |
| 1.52 | <0.1 | | | | |
| 1.53 | 0.3 | | | | |
| 1.19 | <0.1 | | | | |
| 1.43 | <0.1 | | | | |
| 1.44 | 0.13 | | | | |
| Example 10 from WO 02/096888 | 0.4 | 0.6 | 0.4 | 0.7 | 0.8 |

TABLE 2

| Example No. | CDK2/CycE IC$_{50}$ [nM] | CDK1/CycB IC$_{50}$ [nM] | VEGF-R2 IC$_{50}$ [nM] |
|---|---|---|---|
| 2.0 | 16 | 110 | 70 |
| 1.0 | <10 | 79 | 40 |
| 1.3 | 6 | 10 | 140 |
| 1.4 | 10 | 13 | 340 |
| 1.2 | 20 | 130 | 48 |
| 2.1 | 390 | >1000 | 74 |
| 2.3 | 33 | 160 | 61 |
| 1.23 | 6 | 8 | 75 |
| 1.24 | 8 | 5 | 150 |
| 1.25 | 3 | 2 | 70 |
| 1.31 | 9 | 27 | 140 |
| 1.41 | 2 | 2 | 76 |

TABLE 2-continued

| Example No. | CDK2/CycE IC$_{50}$ [nM] | CDK1/CycB IC$_{50}$ [nM] | VEGF-R2 IC$_{50}$ [nM] |
|---|---|---|---|
| 1.42 | 2 | 5 | 64 |
| 1.7 | >1000 | >1000 | 240 |
| 1.26 | 4 | 2 | 31 |
| 1.27 | 4 | 3 | 97 |
| 1.10 | >1000 | >1000 | 910 |
| 1.39 | 19 | 49 | 150 |
| 1.33 | 51 | 200 | 450 |
| 1.35 | 42 | 96 | 94 |
| 1.34 | 28 | 110 | 530 |
| 1.40 | 14 | 21 | 110 |
| 1.63 | 63 | 200 | 89 |
| 1.48 | 7 | 16 | 270 |
| 1.54 | 5 | 8 | 69 |
| 1.11 | 25 | 44 | 83 |
| 1.9 | 4 | 5 | 49 |
| 1.12 | 49 | 160 | 160 |
| 1.6 | 8 | 14 | 29 |
| 1.37 | 48 | 63 | 57 |
| 1.57 | 4 | 8 | 66 |
| 1.49 | 9 | 15 | 470 |
| 1.50 | 9 | 44 | 230 |
| 1.55 | 27 | 45 | 79 |
| 1.56 | 24 | 68 | 32 |
| 1.46 | 4 | 11 | 340 |
| 1.47 | 6 | 27 | 300 |
| 1.16 | 130 | 170 | 130 |
| 1.20 | 54 | 160 | 820 |
| 1.38 | 78 | 75 | 59 |
| 1.36 | 11 | 43 | 92 |
| 1.51 | 4 | 5 | 26 |
| 1.60 | 4 | 4 | 39 |
| 1.14 | 4 | 7 | 69 |
| 1.15 | 4 | 25 | 59 |
| 1.32 | 12 | 16 | 56 |
| 1.28 | 7 | 14 | 37 |
| 3.4 | 41 | 72 | 250 |
| 3.5 | 8 | 17 | 150 |
| 1.58 | 7 | 4 | 45 |
| 1.59 | 7 | 9 | 48 |
| 3.0 | 16 | 49 | 170 |
| 3.6 | 18 | 22 | 200 |
| 3.7 | 11 | 19 | 110 |
| 3.8 | 27 | 91 | >1000 |
| 3.1 | 33 | 97 | 120 |
| 1.29 | 4 | 7 | 16 |
| 1.30 | 6 | 15 | 29 |
| 3.10 | 4 | 18 | |
| 3.9 | 8 | 55 | |
| 1.18 | 3 | 3 | |
| 1.21 | 6 | 5 | |
| 1.53 | 4 | 11 | |
| 1.19 | 3 | 7 | |
| 1.44 | 2 | 5 | |
| Example 10 from WO 02/096888 | <10 | 90 | 200 |

TABLE 3

| Example No. | Inhibition of Human Carboanhydrase-2 IC$_{50}$ [nM] |
|---|---|
| Example 1.0 | >10000 |
| Example 2.0 | >10000 |
| Acetazolamide | 51 |
| Example 10 from WO 02/096888 | 190 |

Tables 1 and 2 show that the compounds according to the invention inhibit cyclin-dependent kinases and/or VEGF receptor tyrosine kinases in the nanomolar range and thus can inhibit the proliferation of tumor cells and/or the tumor angiogenesis.

Table 3 shows that substances according to the invention, in contrast to compounds from the prior art, such as, e.g., acetazolamide or Example 10 from WO02/096888, which represents the closest prior art, do not have any measurable carboanhydrase inhibition and thus no longer exhibit a possible side effect that could be attributed to the carboanhydrase inhibition.

In this respect, the above-mentioned tables confirm that the substances according to the invention are superior in comparison to the prior art.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10349423.5-44, filed Oct. 16, 2003, and U.S. Provisional Application Ser. No. 60/512,921, filed Oct. 22, 2003, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

Figure 1:
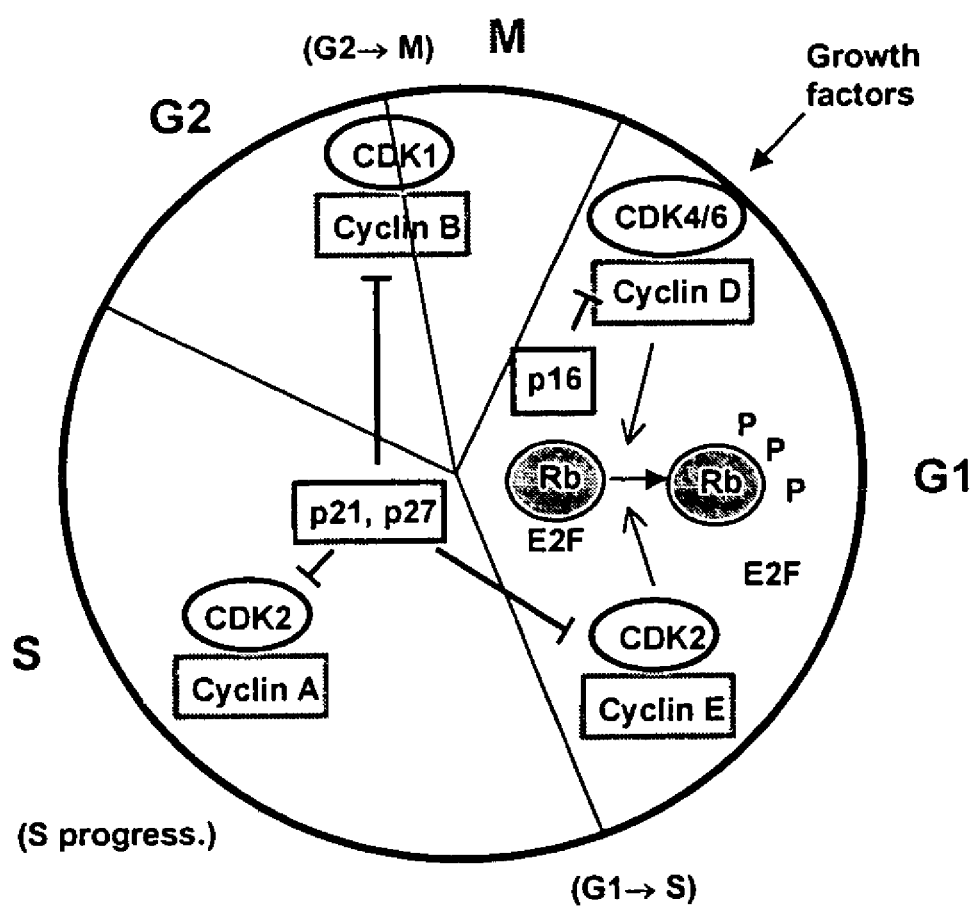
FIG. 1 illustrates the cell-division cycle.

The invention claimed is:

1. A compound of formula (I)

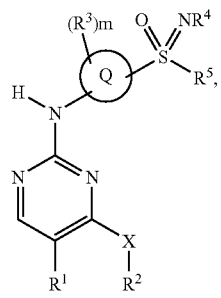

in which
Q is phenyl,
$R^1$ is hydrogen or halogen,
$R^2$ is $C_1$-$C_{10}$-alkyl, $C_2$-$C_{10}$-alkinyl, or aryl that is optionally substituted in one or more places, in the same way or differently, with hydroxy, halogen, $C_1$-$C_6$-alkyl, $C_1$-$C_6$-alkoxy, $C_2$-$C_6$-alkinyl, or —$COR^7$,
X is oxygen, sulfur, or —NH—,
$R^3$ is halogen, or $C_1$-$C_6$-alkyl, or $C_1$-$C_6$-alkoxy that is optionally substituted in one or more places with halogen,
m stands for 0-4,
$R^4$ is hydrogen, $NO_2$, —CO—$R^6$, —$SO_2R^7$ or $C_1$-$C_{10}$-alkyl,
$R^5$ is $C_1$-$C_{10}$-alkyl or $C_3$-$C_{10}$-cycloalkyl that is optionally substituted in one or more places, in the same way or differently, with hydroxy or $C_3$-$C_{10}$-cycloalkyl,
$R^6$ is hydrogen, $C_1$-$C_6$-alkyl, $C_1$-$C_6$-alkoxy or $C_3$-$C_6$-cycloalkyl, which is optionally substituted in one or more places, in the same way or differently, with $C_1$-$C_6$-alkyl, and
$R^7$ is $C_1$-$C_{10}$-alkyl that is optionally substituted in one or more places, in the same way or differently, with trimethyisilanyl.

2. A compound according to claim 1, in which
Q is phenyl,
$R^1$ is hydrogen or halogen,
$R^2$ is $C_1$-$C_{10}$-alkyl, $C_2C_{10}$-alkinyl or aryl that is optionally substituted in one or more places, in the way or differently, with hydroxy, halogen, $C_1$-$C_6$-alkyl, $C_1$-$C_6$-alkoxy, $C_2$-$C_6$-alkinyl or —$COR^{16}$,
X is oxygen, sulfur or —NH—,
$R^3$ is halogen or $C_1$-$C_6$-alkyl or $C_1$-$C_6$-alkoxy that is optionally substituted in one or more places with halogen,
m stands for 0-2,
$R^4$ is hydrogen, $NO_2$, —CO—$R^6$, —$SO_2R^7$ or $C_1$-$C_{10}$-alkyl,
$R^5$ is $C_1$-$C_{10}$-alkyl or $C_3$-$C_{10}$-cycloalkyl that is optionally substituted in one or more places, in the same way or differently, with hydroxy or $C_3$-$C_{10}$-cycloalkyl,
$R^6$ is hydrogen, $C_1$-$C_6$-alkyl, $C_1$-$C_6$-alkoxy or $C_3$-$C_6$-cycloalkyl, which is optionally substituted in one or more places, in the way or differently, with $C_1$-$C_6$-alkyl,
$R^7$ is $C_1$-$C_{10}$-alkyl that is optionally substituted in one or more places, in the way or differently, with trimethylsilanyl.

3. A compound according to claim 1, in which
Q is phenyl,
$R^1$ is hydrogen or halogen,
$R^2$ is methyl, ethyl, propyl, isopropyl, butyl, isobutyl, pentyl, isopentyl, isohexyl, propargyl or phenyl that is optionally substituted in one or more places, in the same way or differently, with hydroxy, halogen, methyl, methoxy, ethinyl, —COH or —$COCH_3$,
X is oxygen, sulfur or —NH—,
$R^3$ is halogen, methyl, methoxy or —$CF_3$,
m stands for 0-1,
$R^4$ is hydrogen, methyl, $NO_2$, —$COOC_2H_5$ or —$SO_2$—$C_2H_4$—$Si(CH_3)_3$,
$R^5$ is methyl, ethyl, cyclopropyl, cyclopentyl, —($CH_2$)-cyclopropyl or hydroxyethyl.

4. In a method of preparing a compound of claim 1, the improvement comprising preparing said compound via an intermediate compound of formula (IIa) or (IIb)

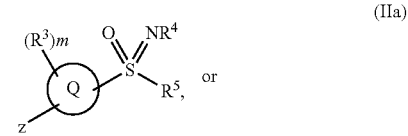

-continued

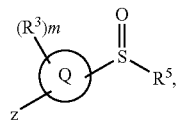
(IIb)

in which

Q is phenyl,

Z is —$NH_2$ or $NO_2$, m stands for 0-4, $R^3$ is halogen, or $C_1$-$C_6$-alkyl, or $C_1$-$C_6$-alkoxy that is optionally substituted in one or more places with halogen, $R^4$ is hydrogen, $NO_2$, —CO—$R^6$, —$SO_2R^6$, —$SO_2R^7$ or $C_1$-$C_{10}$-alkyl, $R^5$ is $C_1$-$C_{10}$-alkyl or $C_3$-$C_{10}$-cycloalkyl that is optionally substituted in one or more places, in the same way or differently, with hydroxyl or $C_3$-$C_{10}$-cycloalkyl, $R^6$ is hydrogen, $C_1$-$C_6$-alkyl, $C_1$-$C_6$-alkoxy or $C_3$-$C_6$-cycloalkyl, which is optionally substituted in one or more places, in the same way or differently, with $C_1$-$C_6$-alkyl, and $R^7$ is $C_1$-$C_{10}$-alkyl that is optionally substituted in one or more places, in the same way or differently, with trimethylsilanyl.

5. A method according to claim 4, wherein m stands for 0-2, $R^3$ is halogen, or $C_1$-$C_{10}$-alkyl or $C_1$-$C_{10}$-alkoxy that is optionally substituted in one or more places with halogen, $R^4$ is hydrogen, $NO_2$, —$SO_2$—$R^7$, —CO—$R^6$ or $C_1$-$C_{10}$-alkyl, $R^5$ is $C_1$-$C_{10}$-alkyl or $C_3$-$C_6$-cycloalkyl that is optionally substituted in one or more places with halogen or hydroxyl, $R^6$ is hydrogen, $C_1$-$C_6$-alkyl, $C_1$-$C_6$-alkoxy or $C_3$-$C_6$-cycloalkyl, which is optionally substituted in one or more places, in the same way or differently, with $C_1$-$C_6$-alkyl, and $R^7$ is $C_1$-$C_{10}$-alkyl that is optionally substituted in one or more places, in the same way or differently, with trimethylsilanyl.

6. In a method of preparing a compound of claim 1, the improvement comprising preparing said compound via an intermediate compound of formula (IV),

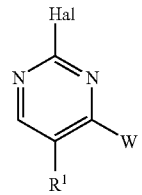
(IV)

in which

Hal is halogen,

W is halogen, hydroxy or X—$R^2$, $R^1$ is hydrogen or halogen, $R^2$ is $C_1$-$C_{10}$-alkyl, $C_2$-$C_{10}$-alkinyl, or aryl that is optionally substituted in one or more places, in the same way or differently, with hydroxy, halogen, $C_1$-$C_6$-alkyl, $C_1$-$C_6$-alkoxy, $C_2$-$C_6$-alkinyl, or —$COR^7$, $R^7$ is $C_1$-$C_{10}$-alkyl that is optionally substituted in one or more places, in the same way or differently, with trimethylsilanyl, and X is oxygen, sulfur, or —NH—.

7. A method according to claim 6, in which

X is oxygen, sulfur or —NH—, $R^1$ is halogen, $R^2$ is $C_1$-$C_{10}$-alkyl or $C_2$-$C_{10}$-alkinyl that is optionally substituted with hydroxy, $C_1$-$C_6$-alkoxy or —CO—$R^7$, and $R^7$ is $C_1$-$C_{10}$-alkyl that is optionally substituted in one or more places, in the same way or differently, with trimethylsilanyl.

8. A pharmaceutical composition comprising a compound according to claim 1 and a pharmaceutically acceptable carrier.

9. A pharmaceutical composition according to claim 8, which is suitable for enteral, parenteral or oral administration.

10. A method for inhibiting the growth of MCF7 cells, NCI-H460 cells, HCT 116 cells, DU 145 cells, or MaTu-MDR cells comprising administering to a patient in need thereof a pharmaceutical composition comprising pharmaceutically acceptable carrier and a compound according to claim 2.

11. A method for inhibiting the growth of MCF7 cells, NCI-H460 cells, HCT 116 cells, DU 145 cells, or MaTu-MDR cells comprising administering to a patient in need thereof a pharmaceutical composition comprising pharmaceutically acceptable carrier and a compound according to claim 3.

12. A method for inhibiting the growth of MCF7 cells, NCI-H460 cells, HCT 116 cells, DU 145 cells, or MaTu-MDR cells comprising administering to a patient in need thereof a pharmaceutical composition according to claim 8.

13. A compound according to claim 1, wherein said compound is in the form of a diastereomer or enantiomer.

* * * * *